United States Patent
Peerce

(12) 
(10) Patent No.: US 6,355,823 B1
(45) Date of Patent: Mar. 12, 2002

(54) INHIBITORS OF INTESTINAL APICAL MEMBRANE NA/PHOSHATE CO-TRANSPORTATION

(75) Inventor: Brian E. Peerce, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/646,654
(22) PCT Filed: Jan. 21, 2000
(86) PCT No.: PCT/US00/01681
  § 371 Date: Sep. 20, 2000
  § 102(e) Date: Sep. 20, 2000
(87) PCT Pub. No.: WO00/43402
  PCT Pub. Date: Jul. 27, 2000

Related U.S. Application Data
(60) Provisional application No. 60/126,417, filed on Jan. 21, 1999.

(51) Int. Cl.[7] .................................................. C07F 9/02
(52) U.S. Cl. ....................... 558/157; 558/158; 558/161; 558/162; 558/163
(58) Field of Search ................................ 558/157, 158, 558/161, 162, 163

(56) References Cited

U.S. PATENT DOCUMENTS

| | | |
|---|---|---|
| 3,851,019 A | 11/1974 | Hogberg et al. |
| 3,862,270 A | 1/1975 | Hogberg et al. |
| 3,869,527 A | 3/1975 | Hogberg et al. |
| 3,897,519 A | 7/1975 | Hogberg et al. |
| 3,937,823 A | 2/1976 | Dea et al. |
| 3,984,501 A | 10/1976 | Rajadhyksha et al. |
| 3,989,825 A | 11/1976 | Hogberg et al. |
| 3,991,187 A | 11/1976 | Hogberg et al. |
| 3,995,033 A | 11/1976 | Hogberg et al. |
| 4,016,223 A | 4/1977 | Rajadhyaksha et al. |
| 4,049,799 A | 9/1977 | Hogberg et al. |
| 4,049,800 A | 9/1977 | Hogberg et al. |
| 4,055,638 A | 10/1977 | Hogberg et al. |
| 4,148,878 A | 4/1979 | Nelson |
| 4,302,448 A | 11/1981 | Bickel et al. |
| 4,327,088 A | 4/1982 | Shinma et al. |

FOREIGN PATENT DOCUMENTS

| | | |
|---|---|---|
| DE | 2 209 595 | 9/1972 |
| EP | 0 051 819 B1 | 2/1985 |
| EP | 0 167 204 | 1/1986 |
| GB | 1 406 611 | 9/1975 |

OTHER PUBLICATIONS

Eakins et al., "On the Prostaglandin Inhibitory Action of Polyphloretin Phosphate," *Advan. Biosci.*, vol. Date 1972, 9:135–138 (1973).

(List continued on next page.)

Primary Examiner—Floyd D. Higel
Assistant Examiner—Ebenezer Sackey
(74) Attorney, Agent, or Firm—Braman & Rogalskyj, LLP

(57) ABSTRACT

The compounds of formula (I) are hydrophilic aryl phosphate, thiophosphate, and aminophosphate intestinal apical membrane Na-mediated phosphate co-transportation inhibitors. The compounds can be administered orally, where they act to inhibit Na-dependent phosphate uptake in the intestines, or internally, where they interact with the phosphate control functions of the kidneys and parathyroid. They are therefore useful for inhibiting sodium-mediated phosphate uptake, reducing serum PTH, calcium, calcitriol, and phosphate, and treating renal disease in an animal, including a human.

57 Claims, 9 Drawing Sheets

OTHER PUBLICATIONS

Crutchley et al., "Prostagladin Inactivation in Guinea–pig Lung and Its Inhibition," *Br. J. Pharmacol.*, 52(2):197–203 (1974).

Piper, "Release and Metabolism of Prostaglandins in Lung Tissue," *Pol. J. Pharmacol. Pharm.*, 26(1–2):61–72 (1974).

Crutchley et al., "Inhibition of the Pulmonary Inactivation of Prostaglandins in vivo by Di–4–phloretin Phosphate," *Br. J. Pharmacol.*, 54(3):301–307 (1975).

Gross et al., "Metabolism of Prostaglandins A1 and E1 in the Perfused Rabbit Lung and the Effects of Selected Inhibitors," *J. Pharmacol. Exp. Ther.*, 198(3):716–724 (1976).

Ishizawa et al., "Inhibitory Actions of Polyphloretin Phosphate and Related Compounds on the Response to Prostaglandin in the Smooth Muscle of Guinea–pig Stomach," *Prostaglandins*, 11(5):829–840 (1976).

Eling et al., "Structural Requirements For, and the Effects of Chemicals On, the Rat Pulmonary Inactivation of Prostaglandins," *Prostaglandins*, 14(1):51–60 (1977).

Fujimoto et al., "Poly– and Di–phloretin Phosphate–induced Alterations on Diuresis and Antidiuresis in Response to Intracerebroventricular Prostagladin A2," *Japan J. Pharmacol.*, 27(4):583–585 (1977).

Bito et al., "Comparison of Renal Prostaglandin and p–Aminohippuric Acid Transport Processes," *Am. J. Physiol.*, 234(1):F80–F88 (1978).

Ortmann et al., "Phosphorylated Derivatives of Phloretin Inhibit Cyclic AMP Accumulation in Neuronal and Glial Tumor Cells in Culture," *Naunyn–Schmiedeberg's Arch. Pharmacol.*, 305(3):233–240 (1978).

Westwick et al., "Selective Antagonism of Prostaglandin (PG) E1, PGD2 and Prostacyclin (PG12) on Human and Rabbit Platelets by Di–4–phloretin Phosphate (DPP)," *Thrombosis Research*, 12(6):973–978 (1978).

Moore et al., "Selective Actions of Aspirin– and Sulfasalazine–like Drugs Against Prostaglandin Synthesis and Breakdown," *Biochem. Pharmacol.*, 31(6):969–971 (1982).

Phillpotts et al., "Evaluation of the Antirhinovirus Chalcone Ro 09–0415 Given Orally to Volunteers," *J. Antimicrob. Chemother.*, 14(4):403–409 (1984).

Rakovska et al., "Antagonistic Effect of Polyphloretin Phosphate and Di–4–phloretin Phosphate on the Contractile Responses of Guinea–pig Gastric Muscles to Prostaglandin E2," *Meth and Find. Exptl. Clin. Pharmacol.*, 6(12):747–750 (1984).

Toda, "Responses of Human, Monkey and Dog Coronary Arteries in vitro to Carbocyclic Thromboxane A2 and Vasodilatiors," *Br. J. Pharmacol.*, 83(2):399–408 (1984).

Kohrle et al., "Flavoniods Inhibit Enzymic Thyroid Hormone Deiodination," *Stud. Org. Chem.*, (Amsterdam) 23 (*Flavonoids and Bioflavonoids*, 1985), 411–421 (1986).

Gabor et al., "Benzopiron–szarmazekok Hasata Patkanyokon, az Egyidejuleg Eloidezett Krotonalaj Ful– es Karragenin Talpodemara" ("Effect on Benzopyrone Derivatives on Simultaneouly–Induced Croton Oil Ear Edema and Carrageenan Paw Edema, in Rats,") *Kiserletes Orvostudomany*, 42(1):57–66 (1990).

Gabor et al., "Effect of Benzopyrone Derivatives on Simultaneously Induced Croton Oil Ear Oedema and Carrageenan Paw Oedema in Rats," *Acta Physiologica Hungarica*, 77(3–4):197–207 (1991).

Gabor et al., "Development and Inhibition of Mouse Ear Oedema Induced with Capsaicin," *Agents Actions*, 36(1–2):83–86 (1992).

Ratnasooriya, "Antireproductive Effect of a Prostonoid Receptor Antagonist (Di–4–phloretin Phosphate) in the Male Rat," *Med. Sci. Res.*, 20(12):445–447 (1992).

Ratnasooriya et al., Effects of the Prostanoid Receptor Antagonist, Di–4–phloretin Phostphate, Upon Human Sperm Motility, *Contraception*, 45(3):239–248 (1992).

Vasilev et al., "Contractile Effects of Prostaglandin E2 in Rat Rectum: Sensitivity to the Prostaglandin Antagonists Diphloretin Phosphate and SC 19220," *Prostaglandins*, 44(5):471–484 (1992).

Blazso et al., "Effects of Prostaglandin Antagonist Phloretin Derivatives on Mouse Ear Edema Induced with Different Skin Irritants," *Prostaglandins*, 50(3):161–168 (1995).

Abstract No. 78:43050u, *Chem. Abstracts*, 78:452 (1973).

Abstract No. 94:174663z, *Chem. Abstracts*, 94:686 (1981).

Abstract No. 97:181953j, *Chem. Abstracts*, 97:782 (1982).

Abstract No. 102:39521v, *Chem. Abstracts*, 102:15–16 (1985).

Abstract No. 113:126200k, *Chem. Abstracts*, 113:__(1990).

INHIBITORS OF INTESTINAL APICAL MEMBRANE NA/PHOSHATE CO-TRANSPORTATION

The present application is a 371 of PCT/US00/01681, which claims priority of U.S. Provisional Patent Application No. 60/126,417, filed Jan. 21, 1999.

BACKGROUND OF THE INVENTION

1. Field of the Invention

This invention relates to compounds that are inhibitors of intestinal apical membrane Na/phosphate co-transportation, medications containing these compounds, and methods for inhibiting sodium-mediated phosphate uptake, reducing serum PTH, calcium, calcitriol, and phosphate, and treating renal disease with these compounds and medications containing them.

2. Description of the Related Art

In 1995, 260,000 people with end-stage renal disease were being treated in this country at a Medicare cost of $9 billion. Another 500,000 people were diagnosed with chronic renal failure. Increasing the time for progression from chronic renal failure to end-stage renal failure by control of serum PTH, calcium, calcitriol, and phosphate, while improving patient nutritional status, would drastically reduce the projected cost of the 500,000 patients progressing to end-stage renal failure and improve the survival of those undergoing dialysis.

However, the medications currently available are less than adequate to address these problems. It would be desirable to develop medications capable of controlling serum PTH, calcium, calcitriol, and phosphate.

BRIEF SUMMARY OF THE INVENTION

In a first aspect, this invention provides compounds of formula (I):

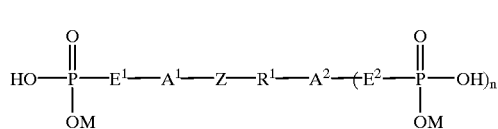

(I)

where:
- $A^1$ and $A^2$ are the same or different aryl groups collectively bearing at least one hydrophilic substituent;
- $E^1$ and $E^2$ are the same or different and are O, S, or $NR^2$ (where $R^2$ is a linear or branched $C_1$–$C_{20}$ carbon containing group);
- M is H or a pharmaceutically acceptable monovalent cation;
- $R^1$ is a linear or branched, saturated or unsaturated, $C_1$–$C_{20}$ carbon containing group;
- Z is a single bond, a carbonyl, $CE^3E^4$, or $CR^3E^3$, where $E^3$ and $E^4$ are the same or different and are $OR^4$, $SR^4$, or $NR^4_2$, where
  - $R^3$ is a linear or branched $C_1$–$C_{20}$ carbon containing group, and
  - $R^4$ is H or a linear or branched $C_1$–$C_{20}$ carbon containing group; and
- n is 0 or 1, or a pharmaceutically acceptable salt thereof, provided that the compound is not 4'-phosphophloretin or a pharmaceutically acceptable salt thereof.

These compounds are hydrophilic aryl phosphate, thiophosphate, and aminophosphate intestinal apical membrane Na-mediated phosphate co-transportation inhibitors; and are useful for inhibiting sodium-mediated phosphate uptake, reducing serum PTH, calcium, calcitriol, and phosphate, and treating renal disease.

In a second aspect, this invention provides a medication including a therapeutically effective amount of at least one compound of formula (I) or 4'-phosphophloretin in a suitable carrier.

In a third aspect, this invention provides a method of inhibiting sodium-mediated phosphate uptake, reducing serum PTH, calcium, calcitriol, and phosphate, and treating renal disease in an animal, including a human, by administering to that animal a therapeutically effective amount of at least one compound of formula (I) or 4'-phosphophloretin, or a medication containing it.

DETAILED DESCRIPTION OF THE INVENTION

Figure 1:
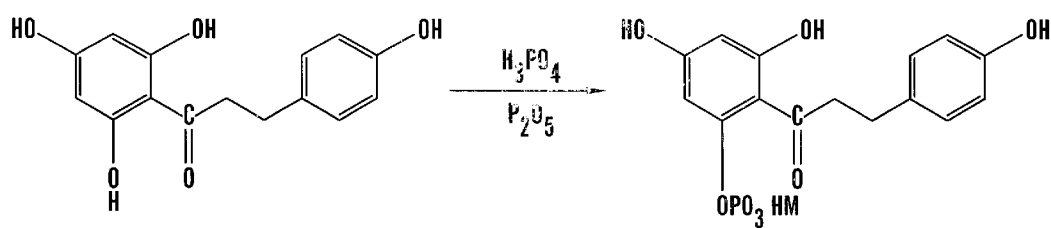
FIG. 1 shows a synthetic scheme for 2'-phosphophloretin (2'-PP).

Na-mediated co-transportation of inorganic phosphate through the apical membrane of the intestines can be inhibited by the oral ingestion of certain hydrophilic aryl phosphates, thiophosphates or aminophosphates. These compounds are thought to competitively bind to a phosphate receptor on the apical membrane, but are incapable of being transported across the membrane. These compounds can be introduced directly into the body of an animal including a human to affect reduction in phosphate content in bodily fluids such as blood, thus reducing the symptoms of hyperphosphatemia and treating renal disease.

Compounds of this Invention

The compounds of this invention are hydrophilic aryl phosphate, thiophosphate, and aminophosphate intestinal apical membrane Na-mediated phosphate co-transportation inhibitors of formula (I):

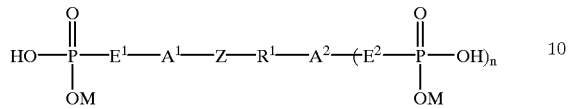

(I)

where:
- $A^1$ and $A^2$ are the same or different aryl groups collectively bearing at least one hydrophilic substituent;
- $E^1$ and $E^2$ are the same or different and are O, S, or $NR^2$ (where $R^2$ is a linear or branched $C_1$–$C_{20}$ carbon containing group);
- M is H or a pharmaceutically acceptable monovalent cation; $R^1$
- is a linear or branched, saturated or unsaturated, $C_1$–$C_{20}$ carbon containing group;
- Z is a single bond, a carbonyl, $CE^3B^4$, or $CR^3E^3$, where $E^3$ and $E^4$ are the same or different and are $OR^4$, $SR^4$, or $NR^4{}_2$, where
    - $R^3$ is a linear or branched $C_1$–$C_{20}$ carbon containing group, and
    - $R^4$ is H or a linear or branched $C_1$–$C_{20}$ carbon containing group; and
- n is 0 or 1, or a pharmaceutically acceptable salt thereof, provided that the compound is not 4'-phosphophloretin or a pharmaceutically acceptable salt thereof.

"Aryl" refers to an aromatic moiety of $C_6$–$_{20}$, preferably $C_6$–$_{16}$, having a single ring (e.g., phenyl), or two or more condensed rings, preferably 2 to 3 condensed rings (e.g., naphthyl), or two or more aromatic rings, preferably 2 to 3 aromatic rings, which are linked by a single bond (e.g., biphenyl). A preferred aryl group is phenyl, collectively substituted with at least one hydrophilic group, especially hydroxy or amino.

Preferred $A^1$ groups include phenyl rings bearing at least one hydrophilic group at the 2, 3, 4, or 5 positions of the phenyl ring, where the hydrophilic group is —OH, —$OR^5$ (where $R^5$ is a carbon containing group having between 1 and 4 carbon atoms), —COOH, —$COOR^6$ (where $R^6$ in a carbon containing group having between 1 and 4 carbon atoms), —$CONR^7$ (where $R^7$ is a carbon containing group having between 1 and 4 carbon atoms), —$SR^1$ (where $R^8$ is a carbon containing group having between 1 and 4 carbon atoms), '—$NR^9R^{10}$ (where $R^9$ and $R^0$ are the same or different and are each a carbon containing group having between 1 and 4 carbon atoms), or the like. Particularly preferred $A^1$ groups include phenyl rings bearing hydrophilic groups at the 4- and 6-positions. Preferred $A^2$ groups include phenyl rings bearing at least one hydrophilic group at the 2-, 3-, 4-, 5-, or 6-positions of the phenyl ring where the hydrophilic groups are as described above for $A^1$. Particularly preferred $A^2$ groups include phenyl rings bearing a hydrophilic group at the 4-position of the phenyl ring. The sites on each phenyl ring that are not occupied by a hydrophilic group may be occupied by non-hydrophilic group(s), provided that such group(s) do not make the molecule hydrophobic. Pharmaceutically acceptable salts of these preferred compounds are also preferred.

Preferred compounds of formula (I) are compounds where $A^1$ and $A^2$ are substituted phenyl, $E^1$ is O, S, or NH; M is potassium; Z is a single bond, a hydroxymethylene group, a dihydroxymethylene group or a carbonyl group, and n is 0. Within these, preferred compounds are those where $E^1$ is at the 2-position of the phenyl group $A^1$.

A preferred class of compounds of formula (I) is compounds of formula (Ia):

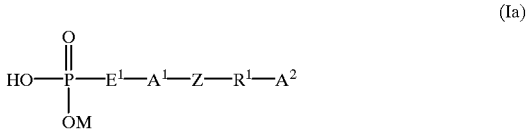

(Ia)

where:
$A^1$, $A^2$, $E^1$, M, $R^1$ and Z are as previously defined for formula (I), or a pharmaceutically acceptable salt thereof.

Preferred compounds of formula (Ia) include compounds where $A^1$ and $A^2$ are phenyl; $E^1$ is O, S, or NH; M is potassium; and Z is a single bond, a hydroxymethylene group, a dihydroxymethylene group, or a carbonyl group, or a pharmaceutically acceptable salt thereof.

Another preferred class of compounds of formula (I) is aryl phosphates of formula (Ib):

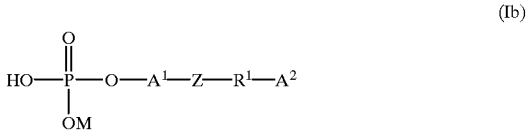

(Ib)

where:
$A^1$, $A^2$, M, $R^1$ and Z are as previously defined for formula (I), or a pharmaceutically acceptable salt thereof.

Another preferred class of compounds of formula (I) is aryl aminophosphates of formula (Ic):

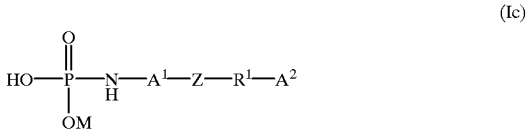

(Ic)

where:
$A^1$, $A^2$, M, $R^1$, and Z are as previously defined for formula (I); and the preferred and particularly preferred substituents are as described for compounds of formula (Ib). Pharmaceutically acceptable salts of these preferred compounds are also preferred.

Another preferred class of compounds of formula (I) is aryl thiophosphates of formula (Id):

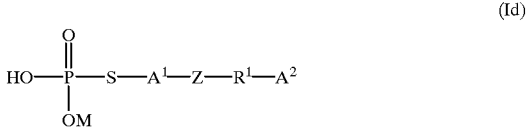

(Id)

where $A^1$, $A^2$, M, $R^1$, and Z are as previously defined for formula (I); and the preferred and particularly preferred substituents are as described for compounds of formula (Ib). Pharmaceutically acceptable salts of these preferred compounds are also preferred.

A particularly preferred class of compounds of formula (I) is aryl phosphates of formula (Ie):

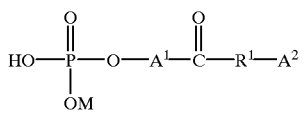

(Ie)

where:
A$^1$, A$^2$, M and R$^1$ are as previously defined for formula (I); and the preferred and particularly preferred substituents are as described for compounds of formula (Ib). Pharmaceutically acceptable salts of these preferred compounds are also preferred.

Another preferred class of compounds of formula (I) is aryl aminophosphates of formula (If):

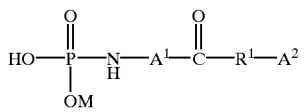

(If)

where:
A$^1$, A$^2$, M and R$^1$ are as previously defined for formula (I); and the preferred and particularly preferred substituents are as described for compounds of formula (Ib). Pharmaceutically acceptable salts of these preferred compounds are also preferred.

Another preferred class of compounds of formula (I) is aryl thiophosphates of formula (Ig):

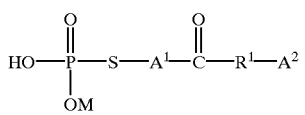

(Ig)

where:
A$^1$, A$^2$, M and R$^1$ are as previously defined for formula (I); and the preferred and particularly preferred substituents are as described for compounds of formula (Ib). Pharmaceutically acceptable salts of these preferred compounds are also preferred.

Particularly preferred examples of compounds of formulas (I) and (Ia) through (Ig) include, without limitation, 2'-phosphophloretin(2'-PP)[CAS name: 1-[2,6-dihydroxy-4-(phosphonooxy)phenyl]-3-(4-hydroxyphenyl)-1-propanone], 3-azido-2'-phosphophloretin (AZPP)[1-[2,6-dihydroxy-4-(phosphonooxy)phenyl]-3-(3-azido-4-hydroxyphenyl)-1-propanone], 4-azido-2'-phosphophloretin [1-[2,6-dihydroxy-4-(phosphonooxy)phenyl]-3-(4-azidophenyl)-1-propanone], 2'-thiophosphophloretin[1-[2,6-dihydroxy-4-(phosphonothio)phenyl]-3-(4-hydroxyphenyl)-1-propanone], 2'-aminophosphophloretin (NHPP)[1-[2,6-dihydroxy-4-(phosphonoimino)phenyl]-3-4-hydroxyphenyl)-1-propanone], and the pharmaceutically acceptable salts thereof, especially the potassium salts.

Illustrative preferred examples of ethane-based compounds of formulas (I) and (Ia) through (Ig) (i.e. those compounds where —Z—R$^1$— is a 2-carbon chain) include, without limitation, 1-(2-phosphonooxy-4-hydroxyphenyl)-2-(3-hydroxyphenyl)ethane,
1-(2-phosphonoimino-4-hydroxyphenyl)-2-(3-hydroxyphenyl)ethane,
1-(2-phosphonothio-4-hydroxyphenyl)-2-(3-hydroxyphenyl)ethane,
1-(2-phosphonooxy-5-hydroxyphenyl)-2-(3-hydroxyphenyl)ethane,
1-(2-phosphonoimino-5-hydroxyphenyl)-2-(3-hydroxyphenyl)ethane,
1-(2-phosphonothio-5-dihydroxyphenyl)-2-(3-hydroxyphenyl)ethane,
1-(2-phosphonooxy-6-hydroxyphenyl)-2-(3-hydroxyphenyl)ethane,
1-(2-phosphonoimino-6-hydroxyphenyl)-2-(3-hydroxyphenyl)ethane,
1-(2-phosphonothio-6-hydroxyphenyl)-2-(3-hydroxyphenyl)ethane,
1-(2-phosphonooxy-4,6-dihydroxyphenyl)-2-(3-hydroxyphenyl)ethane,
1-(2-phosphonoimino-4,6-dihydroxyphenyl)-2-(3-hydroxyphenyl)ethane,
1-(2-phosphonothio-4,6-dihydroxyphenyl)-2-(3-hydroxyphenyl)ethane,
1-(2-phosphonooxy-4-hydroxyphenyl)-2-(4-hydroxyphenyl)ethane,
1-(2-phosphonoimino-4-hydroxyphenyl)-2-(4-hydroxyphenyl)ethane,
1-(2-phosphonothio-4-dihydroxyphenyl)-2-(4-hydroxyphenyl)ethane,
1-(2-phosphonooxy-5-hydroxyphenyl)-2-(4-hydroxyphenyl)ethane,
1-(2-phosphonoimino-5-hydroxyphenyl)-2-(4-hydroxyphenyl)ethane,
1-(2-phosphonothio-5-dihydroxyphenyl)-2-(4-hydroxyphenyl)ethane,
1-(2-phosphonooxy-6-hydroxyphenyl)-2-(4-hydroxyphenyl)ethane,
1-(2-phosphonoimino-6-hydroxyphenyl)-2-(4-hydroxyphenyl)ethane,
1-(2-phosphonothio-6-hydroxyphenyl)-2-(4-hydroxyphenyl)ethane,
1-(2-phosphonooxy-4,6-dihydroxyphenyl)-2-(4-hydroxyphenyl)ethane,
1-(2-phosphonoimino-4,6-dihydroxyphenyl)-2-(4-hydroxyphenyl)ethane,
1-(2-phosphonothio-4,6-dihydroxyphenyl)-2-(4-hydroxyphenyl)ethane,
1-(2-phosphonooxy-4-hydroxyphenyl)-2-(3-hydroxyphenyl)-1-hydroxyethane,
1-(2-phosphonoimino-4-hydroxyphenyl)-2-(3-hydroxyphenyl)-1-hydroxyethane,
1-(2-phosphonothio-4-hydroxyphenyl)-2-(3-hydroxyphenyl)-1-hydroxyethane,
1-(2-phosphonooxy-5-hydroxyphenyl)-2-(3-hydroxyphenyl)-1-hydroxyethane,
1-(2-phosphonoimino-5-hydroxyphenyl)-2-(3-hydroxyphenyl)-1-hydroxyethane,
1-(2-phosphonothio-5-hydroxyphenyl)-2-(3-hydroxyphenyl)-1-hydroxyethane,
1-(2-phosphonooxy-6-hydroxyphenyl)-2-(3-hydroxyphenyl)-1-hydroxyethane,
1-(2-phosphonoimino-6-hydroxyphenyl)-2-(3-hydroxyphenyl)-1-hydroxyethane, 1-(2-phosphonothio-6-hydroxyphenyl)-2-(3-hydroxyphenyl)-1-hydroxyethane,
1-(2-phosphonooxy-4,6-dihydroxyphenyl)-2-(3-hydroxyphenyl)-1-hydroxyethane,
1-(2-phosphonoimino-4,6-dihydroxyphenyl)-2-(3-hydroxyphenyl)-1-hydroxyethane,
1-(2-phosphonothio-4,6-dihydroxyphenyl)-2-(3-hydroxyphenyl)-1-hydroxyethane,
1-(2-phosphonooxy-4-hydroxyphenyl)-2-(4-hydroxyphenyl)-1-hydroxyethane,
1-(2-phosphonoimino-4-hydroxyphenyl)-2-(4-hydroxyphenyl)-1-hydroxyethane,
1-(2-phosphonothio-4-dihydroxyphenyl)-2-(4-hydroxyphenyl)-1-hydroxyethane,
1-(2-phosphonooxy-5-hydroxyphenyl)-2-(4-hydroxyphenyl)-1-hydroxyethane,
1-(2-phosphonoimino-5-hydroxyphenyl)-2-(4-hydroxyphenyl)-1-hydroxyethane,
1-(2-phosphonothio-5-hydroxyphenyl)-2-(4-hydroxyphenyl)-1-hydroxyethane,
1-(2-phosphonooxy-6-hydroxyphenyl)-2-(4-hydroxyphenyl)-1-hydroxyethane,
1-(2-phosphonoimino-6-hydroxyphenyl)-2-(4-hydroxyphenyl)-1-hydroxyethane,
1-(2-phosphonothio-6-hydroxyphenyl)-2-(4-hydroxyphenyl)-1-hydroxyethane,
1-(2-phosphonooxy-4,6-dihydroxyphenyl)-2-(4-hydroxyphenyl-1-hydroxyethane,
1-(2-phosphonoimino-4,6-dihydroxyphenyl)-2-(4-hydroxyphenyl-1-hydroxyethane,
1-(2-phosphonothio-4,6-dihydroxyphenyl)-2-(4-hydroxyphenyl-1-hydroxyethane,
1-(2-phosphonooxy-4-hydroxyphenyl)-2-(3-hydroxyphenyl)-1,1-dihydroxyethane,
1-(2-phosphonoimino-4-hydroxyphenyl)-2-(3-hydroxyphenyl)-1,1-dihydroxyethane,
1-(2-phosphonothio-4-hydroxyphenyl)-2-(3-hydroxyphenyl)-1,1-dihydroxyethane,
1-(2-phosphonooxy-5-hydroxyphenyl)-2-(3-hydroxyphenyl)-1,1-dihydroxyethane,
1-(2-phosphonoimino-5-hydroxyphenyl)-2-(3-hydroxyphenyl)-1,1-dihydroxyethane,
1-(2-phosphonothio-5-hydroxyphenyl)-2-(3-hydroxyphenyl)-1,1-dihydroxyethane,
1-(2-phosphonooxy-6-hydroxyphenyl)-2-(3-hydroxyphenyl)-1,1-dihydroxyethane,
1-(2-phosphonoimino-6-hydroxyphenyl)-2-(3-hydroxyphenyl)-1,1-dihydroxyethane,
1-(2-phosphonothio-6-hydroxyphenyl)-2-(3-hydroxyphenyl)-1,1-dihydroxyethane,
1-(2-phosphonooxy-4,6-dihydroxyphenyl)-2-(3-hydroxyphenyl)-1,1-dihydroxyethane,
1-(2-phosphonoimino-4,6-dihydroxyphenyl)-2-(3-hydroxyphenyl)-1,1-dihydroxyethane,
1-(2-phosphonothio-4,6-dihydroxyphenyl)-2-(3-hydroxyphenyl)-1,1-dihydroxyethane,
1-(2-phosphonooxy-4-hydroxyphenyl)-2-(4-hydroxyphenyl)-1,1-dihydroxyethane,
1-(2-phosphonoimino-4-hydroxyphenyl)-2-(4-hydroxyphenyl)-1,1-dihydroxyethane,
1-(2-phosphonothio-4-dihydroxyphenyl)-2-(4-hydroxyphenyl)-1,1-dihydroxyethane,
1-(2-phosphonooxy-5-hydroxyphenyl)-2-(4-hydroxyphenyl)-1,1-dihydroxyethane,
1-(2-phosphonoimino-5-hydroxyphenyl)-2-(4-hydroxyphenyl)-1,1-dihydroxyethane,
1-(2-phosphonothio-5-dihydroxyphenyl)-2-(4-hydroxyphenyl)-1,1-dihydroxyethane,
1-(2-phosphonooxy-6-hydroxyphenyl)-2-(4-hydroxyphenyl)-1,1-dihydroxyethane,
1-(2-phosphonoimino-6-hydroxyphenyl)-2-(4-hydroxyphenyl)-1,1-dihydroxyethane,
1-(2-phosphonooxy-6-hydroxyphenyl)-2-(4-hydroxyphenyl)-1,1-dihydroxyethane,
1-(2-phosphononooxy-4,6-dihydroxyphenyl)-2-(4-hydroxyphenyl)-1,1-dihydroxyethane,
1-(2-phosphonoimino-4,6-dihydroxyphenyl)-2-(4-hydroxyphenyl)-1,1-dihydroxyethane,
1-(2-phosphonoimino-4,6-dihydroxyphenyl)-2-(4-hydroxyphenyl)-1,1-dihydroxyethane,
1-(2-phosphononooxy-4-hydroxyphenyl)-2-(3-hydroxyphenyl)ethan-1-one,
1-(2-phosphonoimino-4-hydroxyphenyl)-2-(3-hydroxyphenyl)ethan-1-one,
1-(2-phosphonothio-4-hydroxyphenyl)-2-(3-hydroxyphenyl)ethan-1-one,
1-(2-phosphonooxy-5-hydroxyphenyl)-2-(3-hydroxyphenyl)ethan-1-one,
1-(2-phosphonimino-5-hydroxyphenyl)-2-(3-hydroxyphenyl)ethan-1-one,
1-(2-phosphonothio-5-hydroxyphenyl)-2-(3-hydroxyphenyl)ethan-1-one,
1-(2-phosphonooxy-6-hydroxyphenyl)-2-(3-hydroxyphenyl)ethan-1-one,
1-(2-phosphonimino-6-hydroxyphenyl)-2-(3-hydroxyphenyl)ethan-1-one,
1-(2-phosphonothio-6-hydroxyphenyl)-2-(3-hydroxyphenyl)ethan-1-one,
1-(2-phosphonooxy-4,6-dihydroxyphenyl)-2-(3-hydroxyphenyl)ethan-1-one,
1-(2-phosphonimino-4,6-dihydroxyphenyl)-2-(3-hydroxyphenyl)ethan-1-one,
1-(2-phosphonothio-6-hydroxyphenyl)-2-(3-hydroxyphenyl)ethan-1-one,
1-(2-phosphonothio-4-hydroxyphenyl)-2-(4-hydroxyphenyl)ethan-1-one,
1-(2-phosphonoimino-4-hydroxyphenyl)-2-(4-hydroxyphenyl)ethan-1-one,
1-(2-phosphonothio-4-dihydroxyphenyl)-2-(4-hydroxyphenyl)ethan-1-one,
1-(2-phosphonooxy-5-hydroxyphenyl)-2-(4-hydroxyphenyl)ethan-1-one,
1-(2-phosphonoimino-5-hydroxyphenyl)-2-(4-hydroxyphenyl)ethan-1-one,
1-(2-phosphonothio-5-hydroxyphenyl)-2-(4-hydroxyphenyl)ethan-1-one,
1-(2-phosphonooxy-6-hydroxyphenyl)-2-(4-hydroxyphenyl)ethan-1-one,
1-(2-phosphonoimino-6-hydroxyphenyl)-2-(4-hydroxyphenyl)ethan-1-one,
1-(2-phosphonothio-6-hydroxyphenyl)-2-(4-hydroxyphenyl)ethan-1-one,
1-(2-phosphonooxy4,6-dihydroxyphenyl)-2-(4-hydroxyphenyl)ethan-1-one, 1-(2-phosphonoimino-4,6-dihydroxyphenyl)-2-(4-hydroxyphenyl)ethan-1-one, 1-(2-phosphonothio-4,6-dihydroxyphenyl)-2-(4-hydroxyphenyl)ethan-1-one, alkylated analogs (alkyl groups on the alkylenyl connector or on the two phenyl groups), or amino analogs (hydroxy groups replaced by amino groups), and the like, and the pharmaceutically acceptable salts thereof.

Pharmaceutically acceptable salts and anions of the compounds of formula I are suitable for use in the methods of the present invention. A "pharmaceutically acceptable salt" may be any salt derived from an inorganic or organic acid or base. The term "pharmaceutically acceptable anion" refers to the anion of such acid addition salts. The term "pharmaceutically acceptable cation" refers to the cation of the inorganic or organic base that is pharmaceutically acceptable. The salt and/or the anion and/or cation are chosen not to be biologically or otherwise undesirable.

Typically the parent compound is treated with an excess of an alkaline reagent, such as hydroxide, carbonate or alkoxide, containing the appropriate cation. Cations such as $Na^+$, $K^+$, $Ca^{2+}$, $Al^{3+}$, and $NH_4^+$ are examples of cations present in pharmaceutically acceptable salts. Salts may also be prepared using organic bases, such as diethanolamine, ethanolamine, triethanolamine, diethanolamine, N-methylglucamine, ethanolamine, and triethanolamine. The monovalent cation M of the formula (I) may include, but is not limited to, inorganic monovalent cations such as $Na^+$, $K^+$, $NH_4^+$, or organic monovalent cations as listed above. If the compounds of formula I contain a basic group, an acid addition salt may be prepared. Acid addition salts of the compounds are prepared in a standard manner in a suitable solvent from the parent compound and an excess of acid, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p toluene-sulfonic acid, hexanoic acid, heptanoic acid, cyclopentanepropionic acid, lactic acid, o-(4-hydroxy-benzoyl)benzoic acid, 1,2-ethanedisulfonic acid, 2-hydroxyethanesulfonic acid, benzenesulfonic acid, p-chlorobenzenesulfonic acid, 2-naphthalenesulfonic acid, camphorsulfonic acid, 4-methyl-bicyclo[2.2.2. ]oct-2-ene-1-carboxylic acid, glucoheptonic acid, 4,4'-methylenebis(3-hydroxy-2-naphthoic)acid, 3-phenylpropionic acid, trimethyl-acetic acid, t-butylacetic acid, laurylsulfuric acid, glucuronic acid, glutamic acid, 3-hydroxy-2-naphthoic acid, stearic acid, muconic acid and the like. Certain of the compounds form inner salts or zwitterions, which may also be acceptable.

Illustrative preferred examples of propane-based aryl phosphates of formulas (I) and (Ia) through (Ig) include, without limitation, 1-(2-phosphonooxy-4-hydroxyphenyl)-2-(3-hydroxyphenyl)propane, 1-(2-phosphonoimino-4-hydroxyphenyl)-2-(3-hydroxyphenyl)propane, 1-(2-phosphonothio-4-hydroxyphenyl)-2-(3-hydroxyphenyl)propane, 1-(2-phosphonooxy-5-hydroxyphenyl)-2-(3-hydroxyphenyl)propane, 1-(2-phosphonoimino-5-hydroxyphenyl)-2-(3hydroxyphenyl)propane, 1-(2-phosphonothio-5-dihydroxyphenyl)-2-(3-hydroxyphenyl)propane, 1-(2-phosphonooxy-6-hydroxyphenyl)-2-(3-hydroxyphenyl)propane, 1-(2-phosphonoimino-6-hydroxyphenyl)-2-(3-hydroxyphenyl)propane, 1-(2-phosphonothio-6-hydroxyphenyl)-2-(3-hydroxyphenyl)propane, 1-(2-phosphonooxy-4,6-dihydroxyphenyl)-2-(3-hydroxyphenyl)propane, 1-(2-phosphonoimino-4,6-dihydroxyphenyl)-2-(3-hydroxyphenyl)propane, 1-(2-phosphonothio-4,6-dihydroxyphenyl)-2-(3-hydroxyphenyl)propane, 1-(2-phosphonooxy-4-hydroxyphenyl)-2-(4-hydroxyphenyl)propane, 1-(2-phosphonoimino-4-hydroxyphenyl)-2-(4-hydroxyphenyl)propane, 1-(2-phosphonothio-4-dihydroxyphenyl)-2-(4-hydroxyphenyl)propane, 1-(2-phosphonooxy-5-hydroxyphenyl)-2-(4-hydroxyphenyl)propane, 1-(2-phosphonoimino-5-hydroxyphenyl)-2-(4-hydroxyphenyl)propane, 1-(2-phosphonothio-5-dihydroxyphenyl)-2-(4-hydroxyphenyl)propane, 1-(2-phosphonooxy-6-hydroxyphenyl)-2-(4-hydroxyphenyl)propane, 1-(2-phosphonoimino-6-hydroxyphenyl)-2-(4-hydroxyphenyl)propane, 1-(2-phosphonothio-6-hydroxyphenyl)-2-(4-hydroxyphenyl)propane, 1-(2-phosphonooxy-4,6-dihydroxyphenyl)-2-(4-hydroxyphenyl)propane, 1-(2-phosphonoimino-4,6-dihydroxyphenyl)-2-(4-hydroxyphenyl)propane, 1-(2-phosphonothio-4,6-dihydroxyphenyl)-2-(4-hydroxyphenyl)propane, 1-(2-phosphonooxy-4-hydroxyphenyl)-2-(3-hydroxyphenyl)-1-hydroxypropane, 1-(2-phosphonoimino-4-hydroxyphenyl)-2-(3-hydroxyphenyl)-1-hydroxypropane, 1-(2-phosphonothio-4-hydroxyphenyl)-2-(3-hydroxyphenyl)-1-hydroxypropane, 1-(2-phosphonooxy-5-hydroxyphenyl)-2-(3-hydroxyphenyl)-1-hydroxypropane, 1-(2-phosphonoimino-5-hydroxyphenyl)-2-(3-hydroxyphenyl)-1-hydroxypropane, 1-(2-phosphonothio-5-hydroxyphenyl)-2-(3-hydroxyphenyl)-1-hydroxypropane, 1-(2-phosphonooxy-6-hydroxyphenyl)-2-(3-hydroxyphenyl)-1-hydroxypropane, 1-(2-phosphonoimino-6-hydroxyphenyl)-2-(3-hydroxyphenyl)-1-hydroxypropane, 1-(2-phosphonothio-6-hydroxyphenyl)-2-(3-hydroxyphenyl)-1-hydroxypropane, 1-(2-phosphonooxy-4,6-dihydroxyphenyl)-2-(3-hydroxyphenyl)-1-hydroxypropane, 1-(2-phosphonoimino-4,6-dihydroxyphenyl)-2-(3-hydroxyphenyl)-1-hydroxypropane, 1-(2-phosphonothio-4,6-dihydroxyphenyl)-2-(3-hydroxyphenyl-1-hydroxypropane, 1-(2-phosphonooxy-4-hydroxyphenyl)-2-(4-hydroxyphenyl)-1-hydroxypropane,
1-(2-phosphonoimino-4-hydroxyphenyl)-2-(4-hydroxyphenyl)-1-hydroxypropane,
1-(2-phosphonothio-4-dihydroxyphenyl)-2-(4-hydroxyphenyl)-1-hydroxypropane,
1-(2-phosphonooxy-5-hydroxyphenyl)-2-(4-hydroxyphenyl)-1-hydroxypropane,
1-(2-phosphonoimino-5-hydroxyphenyl)-2-(4-hydroxyphenyl)-1-hydroxypropane,
1-(2-phosphonothio-5-hydroxyphenyl)-2-(4-hydroxyphenyl)-1-hydroxypropane,
1-(2-phosphonooxy-6-hydroxyphenyl)-2-(4-hydroxyphenyl)-1-hydroxypropane,
1-(2-phosphonoimino-6-hydroxyphenyl)-2-(4-hydroxyphenyl)-1-hydroxypropane,
1-(2-phosphonothio-6-hydroxyphenyl)-2-(4-hydroxyphenyl)-1-hydroxypropane,
1-(2-phosphonooxy-4,6-dihydroxyphenyl)-2-(4-hydroxyphenyl)-1-hydroxypropane,
1-(2-phosphonoimino-4,6-dihydroxyphenyl)-2-(4-hydroxyphenyl)-1-hydroxypropane,
1-(2-phosphonothio-4,6-dihydroxyphenyl)-2-(4-hydroxyphenyl)-1-hydroxypropane,
1-(2-phosphonooxy-4-hydroxyphenyl)-2-(3-hydroxyphenyl)-1,1-dihydroxypropane,
1-(2-phosphonoimino-4-hydroxyphenyl)-2-(3-hydroxyphenyl)-1,1-dihydroxypropane,
1-(2-phosphonothio-4-hydroxyphenyl)-2-(3-hydroxyphenyl)-1,1-dihydroxypropane,
1-(2-phosphonooxy-5-hydroxyphenyl)-2-(3-hydroxyphenyl)-1,1-dihydroxypropane,
1-(2-phosphonoimino-5-hydroxyphenyl)-2-(3-hydroxyphenyl)-1,1-dihydroxypropane,
1-(2-phosphonothio-5-hydroxyphenyl)-2-(3-hydroxyphenyl)-1,1-dihydroxypropane,
1-(2-phosphonooxy-6-hydroxyphenyl)-2-(3-hydroxyphenyl)-1,1-dihydroxypropane,
1-(2-phosphonoimino-6-hydroxyphenyl)-2-(3-hydroxyphenyl)-1,1-dihydroxypropane,
1-(2-phosphonothio-6-hydroxyphenyl)-2-(3-hydroxyphenyl)-1,1-dihydroxypropane,
1-(2-phosphonooxy-4,6-dihydroxyphenyl)-2-(3-hydroxyphenyl)-1,1-dihydroxypropane,
1-(2-phosphonoimino-4,6-dihydroxyphenyl)-2-(3-hydroxyphenyl)-1,1-dihydroxypropane,
1-(2-phosphonothio-4,6-dihydroxyphenyl)-2-(3-hydroxyphenyl)-1,1-dihydroxypropane,
1-(2-phosphonooxy-4-hydroxyphenyl)-2-(4-hydroxyphenyl)-1,1-dihydroxypropane,
1-(2-phosphonoimino-4-hydroxyphenyl)-2-(4-hydroxyphenyl)-1,1-dihydroxypropane,
1-(2-phosphonothio-4-dihydroxyphenyl)-2-(4-hydroxyphenyl)-1,1-dihydroxypropane,
1-(2-phosphonooxy-5-hydroxyphenyl)-2-(4-hydroxyphenyl)-1,1-dihydroxypropane,
1-(2-phosphonoimino-5-hydroxyphenyl)-2-(4-hydroxyphenyl)-1,1-dihydroxypropane,
1-(2-phosphonothio-5-dihydroxyphenyl)-2-(4-hydroxyphenyl)-1,1-dihydroxypropane,
1-(2-phosphonooxy-6-hydroxyphenyl)-2-(4-hydroxyphenyl)-1,1-dihydroxypropane,
1-(2-phosphonoimino-6-hydroxyphenyl)-2-(4-hydroxyphenyl)-1,1-dihydroxypropane,
1-(2-phosphonothio-6-hydroxyphenyl)-2-(4-hydroxyphenyl)-1,1-dihydroxypropane,
1-(2-phosphonooxy-4,6-dihydroxyphenyl)-2-(4-hydroxyphenyl)-1,1-dihydroxypropane,
1-(2-phosphonoimino-4,6-dihydroxyphenyl)-2-(4-hydroxyphenyl)-1,1-dihydroxypropane,
1-(2-phosphonothio-4,6-dihydroxyphenyl)-2-(4-hydroxyphenyl)-1,1-dihydroxypropane,
1-(2-phosphonooxy-4-hydroxyphenyl)-2-(3-hydroxyphenyl)propan-1-one,
1-(2-phosphonoimino-4-hydroxyphenyl)-2-(3-hydroxyphenyl)propan-1-one,
1-(2-phosphonothio-4-hydroxyphenyl)-2-(3-hydroxyphenyl)propan-1-one,
1-(2-phosphonooxy-5-hydroxyphenyl)-2-(3-hydroxyphenyl)propan-1-one,
1-(2-phosphonoimino-5-hydroxyphenyl)-2-(3-hydroxyphenyl)propan-1-one,
1-(2-phosphonothio-5-hydroxyphenyl)-2-(3-hydroxyphenyl)propan-1-one,
1-(2-phosphonooxy-6-hydroxyphenyl)-2-(3-hydroxyphenyl)propan-1-one,
1-(2-phosphonoimino-6-hydroxyphenyl)-2-(3-hydroxyphenyl)propan-1-one,
1-(2-phosphonothio-6-hydroxyphenyl)-2-(3-hydroxyphenyl)propan-1-one,
1-(2-phosphonooxy-4,6-dihydroxyphenyl)-2-(3-hydroxyphenyl)propan-1-one,
1-(2-phosphonoimino-4,6-dihydroxyphenyl)-2-(3-hydroxyphenyl)propan-1-one,
1-(2-phosphonothio-4,6-dihydroxyphenyl)-2-(3-hydroxyphenyl)propan-1-one,
1-(2-phosphonooxy-4-hydroxyphenyl)-2-(4-hydroxyphenyl)propan-1-one,
1-(2-phosphonoimino-4-hydroxyphenyl)-2-(4-hydroxyphenyl)propan-1-one,
1-(2-phosphonothio-4-dihydroxyphenyl)-2-(4-hydroxyphenyl)propan-1-one,
1-(2-phosphonooxy-5-hydroxyphenyl)-2-(4-hydroxyphenyl)propan-1-one,
1-(2-phosphonoimino-5-hydroxyphenyl)-2-(4-hydroxyphenyl)propan-1-one,
1-(2-phosphonothio-5-hydroxyphenyl)-2-(4-hydroxyphenyl)propan-1-one,
1-(2-phosphonooxy-6-hydroxyphenyl)-2-(4-hydroxyphenyl)propan-1-one,
1-(2-phosphonoimino-6-hydroxyphenyl)-2-(4-hydroxyphenyl)propan-1-one,
1-(2-phosphonothio-6-hydroxyphenyl)-2-(4-hydroxyphenyl)propan-1-one,
1-(2-phosphonooxy-4,6-dihydroxyphenyl)-2-(4-hydroxyphenyl)propan-1-one, 1-(2-phosphonoimino-4,6-dihydroxyphenyl)-2-(4-hydroxyphenyl)propan-1-one,
1-(2-phosphonothio-4,6-dihydroxyphenyl)-2-(4-hydroxyphenyl)propan-1-one,
1-(2-phosphonooxy-4-hydroxyphenyl)-3-(3-hydroxyphenyl)propane,
1-(2-phosphonoimino-4-hydroxyphenyl)-3-(3-hydroxyphenyl)propane, 1-(2-phosphonothio-4-hydroxyphenyl)-3-(3-hydroxyphenyl)propane,
1-(2-phosphonooxy-5-hydroxyphenyl)-3-(3-hydroxyphenyl)propane,
-1-(2-phosphonoimino-5-hydroxyphenyl)-3-(3-hydroxyphenyl)propane,
1-(2-phosphonothio-5-dihydroxyphenyl)-3-(3-hydroxyphenyl)propane,
1-(2-phosphonooxy-6-hydroxyphenyl)-3-(3-hydroxyphenyl)propane,
1-(2-phosphonoimino-6-hydroxyphenyl)-3-(3-hydroxyphenyl)propane,
1-(2-phosphonothio-6-hydroxyphenyl)-3-(3-hydroxyphenyl)propane,
1-(2-phosphonooxy-4,6-dihydroxyphenyl)-3-(3-hydroxyphenyl)propane,
1-(2-phosphonoimino-4,6-dihydroxyphenyl)-3-(3-hydroxyphenyl)propane,
1-(2-phosphonothio-4,6-dihydroxyphenyl)-3-(3-hydroxyphenyl)propane,
1-(2-phosphonooxy-4-hydroxyphenyl)-3-(4-hydroxyphenyl)propane,
1-(2-phosphonoimino-4-hydroxyphenyl)-3-(4-hydroxyphenyl)propane,
1-(2-phosphonothio-4-dihydroxyphenyl)-3-(4-hydroxyphenyl)propane,
1-(2-phosphonooxy-5-hydroxyphenyl)-3-(4-hydroxyphenyl)propane,
1-(2-phosphonoimino-5-hydroxyphenyl)-3-(4-hydroxyphenyl)propane,
1-(2-phosphonothio-5-dihydroxyphenyl)-3-(4-hydroxyphenyl)propane,
1-(2-phosphonooxy-6-hydroxyphenyl)-3-(4-hydroxyphenyl)propane,
1-(2-phosphonoimino-6-hydroxyphenyl)-3-(4-hydroxyphenyl)propane,
1-(2-phosphonothio-6-hydroxyphenyl)-3-(4-hydroxyphenyl)propane,
1-(2-phosphonooxy-4,6-dihydroxyphenyl)-3-(4-hydroxyphenyl)propane,
1-(2-phosphonoimino-4,6-dihydroxyphenyl)-3-(4-hydroxyphenyl)propane,
1-(2-phosphonothio-4,6-dihydroxyphenyl)-3-(4-hydroxyphenyl)propane,
1-(2-phosphonooxy-4-hydroxyphenyl)-3-(3-hydroxyphenyl)-1-hydroxypropane,
1-(2-phosphonoimino-4-hydroxyphenyl)-3-(3-hydroxyphenyl)-1-hydroxypropane,
1-(2-phosphonothio-4-hydroxyphenyl-3-(3-hydroxyphenyl-1-hydroxypropane,
1-(2-phosphonooxy-5-hydroxyphenyl)-3-(3-hydroxyphenyl)-1-hydroxypropane,
1-(2-phosphonoimino-5-hydroxyphenyl)-3-(3-hydroxyphenyl)-1-hydroxypropane,
1-(2-phosphonothio-5-hydroxyphenyl)-3-(3-hydroxyphenyl)-1-hydroxypropane,
1-(2-phosphonooxy-6-hydroxyphenyl)-3-(3-hydroxyphenyl-1-hydroxypropane,
1-(2-phosphonoimino-6-hydroxyphenyl)-3-(3-hydroxyphenyl)-1-hydroxypropane,
1-(2-phosphonothio-6-hydroxyphenyl)-3-(3-hydroxyphenyl)-1-hydroxypropane,
1-(2-phosphonooxy-4,6-dihydroxyphenyl)-3-(3-hydroxyphenyl)-1-hydroxypropane,
1-(2-phosphonoimino-4,6-dihydroxyphenyl)-3-(3-hydroxyphenyl-1-hydroxypropane,
1-(2-phosphonothio-4,6-dihydroxyphenyl)-3-(3-hydroxyphenyl)-1-hydroxypropane,
1-(2-phosphonooxy-4-hydroxyphenyl)-3-(4-hydroxyphenyl-1-hydroxypropane,
1-(2-phosphonoimino-4-hydroxyphenyl)-3-(4-hydroxyphenyl)-1-hydroxypropane,
1-(2-phosphonothio-4-dibydroxyphenyl)-3-(4-hydroxyphenyl)-1-hydroxypropane,
1-(2-phosphonooxy-5-hydroxyphenyl)-3-(4-hydroxyphenyl)-1-hydroxypropane,
1-(2-phosphonoimino-5-hydroxyphenyl)-3-(4-hydroxyphenyl)-1-hydroxypropane,
1-(2-phosphonothio-5-hydroxyphenyl)-3-(4-hydroxyphenyl)-1-hydroxypropane,
1-(2-phosphonooxy-6-hydroxyphenyl)-3-(4-hydroxyphenyl)-1-hydroxypropane,
1-(2-phosphonoimino-6-hydroxyphenyl)-3-(4-hydroxyphenyl)-1-hydroxypropane,
1-(2-phosphonothio-6-hydroxyphenyl)-3-(4-hydroxyphenyl)-1-hydroxypropane,
1-(2-phosphonooxy-4,6-dihydroxyphenyl)-3-(4-hydroxyphenyl)-1-hydroxypropane,
1-(2-phosphonoimino-4,6-dihydroxyphenyl)-3-(4-hydroxyphenyl)-1-hydroxypropane,
1-(2-phosphonothio-4,6-dihydroxyphenyl)-3-(4-hydroxyphenyl)-1-hydroxypropane,
1-(2-phosphonooxy-4-hydroxyphenyl)-3-(3-hydroxyphenyl)-1,1-dihydroxypropane,
1-(2-phosphonoimino-4-hydroxyphenyl)-3-(3-hydroxyphenyl)-1,1-dihydroxypropane,
1-(2-phosphonothio-4-hydroxyphenyl)-3-(3-hydroxyphenyl)-1,1-dihydroxypropane,
1-(2-phosphonooxy-5-hydroxyphenyl)-3-(3-hydroxyphenyl)-1,1-dihydroxypropane,
1-(2-phosphonoimino-5-hydroxyphenyl)-3-(3-hydroxyphenyl)-1,1-dihydroxypropane,
1-(2-phosphonothio-5-hydroxyphenyl)-3-(3-hydroxyphenyl)-1,1-dihydroxypropane,
1-(2-phosphonooxy-6-hydroxyphenyl)-3-(3-hydroxyphenyl)-1,1-dihydroxypropane,
1-(2-phosphonoimino-6-hydroxyphenyl)-3-(3-hydroxyphenyl)-1,1-dihydroxypropane,
1-(2-phosphonothio-6-hydroxyphenyl)-3-(3-hydroxyphenyl)-1,1-dihydroxypropane,
1-(2-phosphonooxy-4,6-dihydroxyphenyl)-3-(3-hydroxyphenyl)-1,1-dihydroxypropane,
1-(2-phosphonoimino-4,6-dihydroxyphenyl)-3-(3-hydroxyphenyl)-1,1-dihydroxypropane,
1-(2-phosphonothio-4,6-dihydroxyphenyl)-3-(3-hydroxyphenyl)-1,1-dihydroxypropane,
1-(2-phosphonooxy-4-hydroxyphenyl)-3-(4-hydroxyphenyl)-1,1-dihydroxypropane,
1-(2-phosphonoimino-4-hydroxyphenyl)-3-(4-hydroxyphenyl)-1,1-dihydroxypropane,
1-(2-phosphonothio-4-dihydroxyphenyl)-3-(4-hydroxyphenyl)-1,1-dihydroxypropane,
1-(2-phosphonooxy-5-hydroxyphenyl)-3-(4-hydroxyphenyl)-1,1-dihydroxypropane, 1-(2-phosphonoimino-5-hydroxyphenyl)-3-(4-hydroxyphenyl)-1,1-dihydroxypropane,
1-(2-phosphonothio-5-dihydroxyphenyl)-3-(4-hydroxyphenyl)-1,1-dihydroxypropane,
1-(2-phosphonooxy-6-hydroxyphenyl)-3-(4-hydroxyphenyl)-1,1-dihydroxypropane,
1-(2-phosphonoimino-6-hydroxyphenyl)-3-(4-hydroxyphenyl)-1,1-dihydroxypropane,
1-(2-phosphonothio-6-hydroxyphenyl)-3-(4-hydroxyphenyl)-1,1-dihydroxypropane,
1-(2-phosphonooxy-4,6-dihydroxyphenyl)-3-(4-hydroxyphenyl)-1,1-dihydroxypropane,
1-(2-phosphonoimino-4,6-dihydroxyphenyl)-3-(4-hydroxyphenyl)-1,1-dihydroxypropane,
1-(2-phosphonothio-4,6-dihydroxyphenyl)-3-(4-hydroxyphenyl)-1,1-dihydroxypropane,
1-(2-phosphonooxy-4-hydroxyphenyl)-3-(3-hydroxyphenyl)propan-1-one,
1-(2-phosphonoimino-4-hydroxyphenyl)-3-(3-hydroxyphenyl)propan-1-one,
1-(2-phosphonothio-4-hydroxyphenyl)-3-(3-hydroxyphenyl)propan-1-one,
1-(2-phosphonooxy-5-hydroxyphenyl)-3-(3-hydroxyphenyl)propan-1-one,
1-(2-phosphonoimino-5-hydroxyphenyl)-3-(3-hydroxyphenyl)propan-1-one,
1-(2-phosphonothio-5-hydroxyphenyl)-3-(3-hydroxyphenyl)propan-1-one,
1-(2-phosphonooxy-6-hydroxyphenyl)-3-(3-hydroxyphenyl)propan-1-one,
1-(2-phosphonoimino-6-hydroxyphenyl)-3-(3-hydroxyphenyl)propan-1-one,
1-(2-phosphonothio-6-hydroxyphenyl)-3-(3-hydroxyphenyl)propan-1-one,
1-(2-phosphonooxy-4,6-dihydroxyphenyl)-3-(3-hydroxyphenyl)propan-1-one,
1-(2-phosphonoimino-4,6-dihydroxyphenyl)-3-(3-hydroxyphenyl)propan-1-one,
1-(2-phosphonothio-4,6-dihydroxyphenyl)-3-(3-hydroxyphenyl)propan-1-one,
1-(2-phosphonooxy-4-hydroxyphenyl)-3-(4-hydroxyphenyl)propan-1-one,
1-(2-phosphonoimino-4-hydroxyphenyl)-3-(4-hydroxyphenyl)propan-1-one,
1-(2-phosphonothio-4-dihydroxyphenyl)-3-(4-hydroxyphenyl)propan-1-one,
1-(2-phosphonooxy-5-hydroxyphenyl)-3-(4-hydroxyphenyl)propan-1-one,
1-(2-phosphonoimino-5-hydroxyphenyl)-3-(4-hydroxyphenyl)propan-1-one,
1-(2-phosphonothio-5-hydroxyphenyl)-3-(4-hydroxyphenyl)propan-1-one,
1-(2-phosphonooxy-6-hydroxyphenyl)-3-(4-hydroxyphenyl)propan-1-one,
1-(2-phosphonoimino-6-hydroxyphenyl)-3-(4-hydroxyphenyl)propan-1-one,
1-(2-phosphonothio-6-hydroxyphenyl)-3-(4-hydroxyphenyl)propan-1-one,
1-(2-phosphonooxy-4,6-dihydroxyphenyl)-3-(4-hydroxyphenyl)propan-1-one,
1-(2-phosphonoimino-4,6-dihydroxyphenyl)-3-(4-hydroxyphenyl)propan-1-one,
1-(2-phosphonothio-4,6-dihydroxyphenyl)-3-(4-hydroxyphenyl)propan-1-one, alkylated analogs (alkyl groups on the alkylenyl connector or on the two phenyl groups), or amino analogs (hydroxy groups replaced by amino groups), and the like, and the pharmaceutically acceptable salts thereof.

Illustrative preferred examples of butane-based aryl phosphates formulas (I) and (Ia) through (Ig) include, without limitation, 1-(2-phosphonooxy-4-hydroxyphenyl)-2-(3-hydroxyphenyl)butane,
1-(2-phosphonoimino-4-hydroxyphenyl)-2-(3-hydroxyphenyl)butane,
1-(2-phosphonothio-4-hydroxyphenyl)-2-(3-hydroxyphenyl)butane,
1-(2-phosphonooxy-5-hydroxyphenyl)-2-(3-hydroxyphenyl)butane,
1-(2-phosphonoimino-5-hydroxyphenyl)-2-(3-hydroxyphenyl)butane,
1-(2-phosphonothio-5-dihydroxyphenyl)-2-(3-hydroxyphenyl)butane,
1-(2-phosphonooxy-6-hydroxyphenyl)-2(3-hydroxyphenyl)butane,
1-(2-phosphonoimino-6-hydroxyphenyl)-2-(3-hydroxyphenyl)butane,
1-(2-phosphonothio-6-hydroxyphenyl)-2-(3-hydroxyphenyl)butane,
1-(2-phosphonooxy-4,6-dihydroxyphenyl)-2(3hydroxyphenyl)butane,
1-(2-phosphonoimino-4,6-dihydroxyphenyl)-2-(3-hydroxyphenyl)butane,
1-(2-phosphonothio-4,6-dihydroxyphenyl)-2-(3-hydroxyphenyl)butane,
1-(2-phosphonooxy-4-hydroxyphenyl)-2-(4-hydroxyphenyl)butane,
1-(2-phosphonoimino-4-hydroxyphenyl)-2-(4-hydroxyphenyl)butane,
1-(2-phosphonothio-4-hydroxyphenyl)-2-(4-hydroxyphenyl)butane,
1-(2-phosphonooxy-5-hydroxyphenyl)-2-(4-hydroxyphenyl)butane,
1-(2-phosphonoimino-5-hydroxyphenyl)-2-(4-hydroxyphenyl)butane,
1-(2-phosphonothio-5-dihydroxyphenyl)-2-(4-hydroxyphenyl)butane,
1-(2-phosphonooxy-6-hydroxyphenyl)-2-(4-hydroxyphenyl)butane,
1-(2phosphonoimino-6-hydroxyphenyl)-2-(4-hydroxyphenyl)butane,
1-(2-phosphonothio-6-hydroxyphenyl)-2-(4-hydroxyphenyl)butane,
1-(2-phosphonooxy-4,6-dihydroxyphenyl)-2-(4-hydroxyphenyl)butane,
1-(2-phosphonoimino-4,6-dihydroxyphenyl)-2-(4hydroxyphenyl)butane,
1-(2-phosphonothio-4,6-dihydroxyphenyl)-2-(4-hydroxyphenyl)butane,
1-(2-phosphonooxy-4-hydroxyphenyl)-2-(3-hydroxyphenyl)-1-hydroxybutane,
1-(2-phosphonoimino-4-hydroxyphenyl)-2-(3-hydroxyphenyl-1-hydroxybutane,
1-(2-phosphonothio-4-hydroxyphenyl)-2-(3-hydroxyphenyl-1-hydroxybutane, 1-(2-phosphonooxy-5-hydroxyphenyl)-2-(3-hydroxyphenyl)-1-hydroxybutane,
1-(2-phosphonoimino-5-hydroxyphenyl)-2-(3-hydroxyphenyl-1-hydroxybutane,
1-(2-phosphonothio-5-hydroxyphenyl)-2-(3-hydroxyphenyl)-1-hydroxybutane,
1-(2-phosphonooxy-6-hydroxyphenyl)-2-(3-hydroxyphenyl)-1-hydroxybutane,
1-(2-phosphonoimino-6-hydroxyphenyl)-2-(3-hydroxyphenyl)-1-hydroxybutane,
1-(2-phosphonothio-6-hydroxyphenyl)-2-(3-hydroxyphenyl)-1-hydroxybutane,
1-(2-phosphonooxy-4,6-dihydroxyphenyl)-2-(3-hydroxyphenyl)-1-hydroxybutane,
1-(2-phosphonoimino-4,6-dihydroxyphenyl)-2-(3-hydroxyphenyl)-1-hydroxybutane,
1-(2-phosphonothio-4,6-dihydroxyphenyl)-2-(3-hydroxyphenyl)-1-hydroxybutane,
1-(2-phosphonooxy-4-hydroxyphenyl)-2-(4-hydroxyphenyl)-1-hydroxybutane,
1-(2-phosphonoimino-4-hydroxyphenyl)-2-(4-hydroxyphenyl)-1-hydroxybutane,
1-(2-phosphonothio-4-dihydroxyphenyl)-2-(4-hydroxyphenyl)-1-hydroxybutane,
1-(2-phosphonooxy-5-hydroxyphenyl)-2-(4-hydroxyphenyl)-1-hydroxybutane,
1-(2-phosphonoimino-5-hydroxyphenyl)-2-(4-hydroxyphenyl)-1-hydroxybutane,
1-(2-phosphonothio-5-hydroxyphenyl)-2-(4-hydroxyphenyl)-1-hydroxybutane,
1-(2-phosphonooxy-6-hydroxyphenyl)-2-(4-hydroxyphenyl)-1-hydroxybutane,
1-(2-phosphonoimino-6-hydroxyphenyl)-2-(4-hydroxyphenyl)-1-hydroxybutane,
1-(2-phosphonothio-6-hydroxyphenyl)-2-(4-hydroxyphenyl)-1-hydroxybutane,
1-(2-phosphonooxy-4,6-dihydroxyphenyl)-2-(4-hydroxyphenyl)-1-hydroxybutane,
1-(2-phosphonoimino-4,6-dihydroxyphenyl)-2-(4-hydroxyphenyl)-1-hydroxybutane,
1-(2-phosphonothio-4,6-dihydroxyphenyl)-2-(4-hydroxyphenyl)-1-hydroxybutane,
1-(2-phosphonooxy-4-hydroxyphenyl)-2-(3-hydroxyphenyl)-1,1-dihydroxybutane,
1-(2-phosphonoimino-4-hydroxyphenyl)-2-(3-hydroxyphenyl)-1,1-dihydroxybutane,
1-(2-phosphonothio-4-hydroxyphenyl)-2-(3-hydroxyphenyl)-1,1-dihydroxybutane,
1-(2-phosphonooxy-5-hydroxyphenyl)-2-(3-hydroxyphenyl)-1,1-dihydroxybutane,
1-(2-phosphonoimino-5-hydroxyphenyl)-2-(3-hydroxyphenyl)-1,1-dihydroxybutane,
1-(2-phosphonothio-5-hydroxyphenyl)-2-(3-hydroxyphenyl)-1,1-dihydroxybutane,
1-(2-phosphonooxy-6-hydroxyphenyl)-2-(3-hydroxyphenyl)-1,1-dihydroxybutane,
1-(2-phosphonoimino-6-hydroxyphenyl)-2-(3-hydroxyphenyl)-1,1-dihydroxybutane,
1-(2-phosphonothio-6-hydroxyphenyl)-2-(3-hydroxyphenyl)-1,1-dihydroxybutane,
1-(2-phosphonooxy-4,6-dihydroxyphenyl)-2-(3-hydroxyphenyl)-1,1-dihydroxybutane,
1-(2-phosphonoimino-4,6-dihydroxyphenyl)-2-(3-hydroxyphenyl)-1,1-dihydroxybutane,
1-(2-phosphonothio-4,6-dihydroxyphenyl)-2-(3-hydroxyphenyl)-1,1-dihydroxybutane,
1-(2-phosphonooxy-4-hydroxyphenyl)-2-(4-hydroxyphenyl)-1,1-dihydroxybutane,
1-(2-phosphonoimino-4-hydroxyphenyl)-2-(4-hydroxyphenyl)-1,1-dihydroxybutane,
1-(2-phosphonothio-4-dihydroxyphenyl)-2-(4-hydroxyphenyl)-1,1-dihydroxybutane,
1-(2-phosphonooxy-5-hydroxyphenyl)-2-(4-hydroxyphenyl)-1,1-dihydroxybutane,
1-(2-phosphonoimino-5-hydroxyphenyl)-2-(4-hydroxyphenyl)-1,1-dihydroxybutane,
1-(2-phosphonothio-5-dihydroxyphenyl)-2-(4-hydroxyphenyl)-1,1-dihydroxybutane,
1-(2-phosphonooxy-6-hydroxyphenyl)-2-(4-hydroxyphenyl)-1,1-dihydroxybutane,
1-(2-phosphonoimino-6-hydroxyphenyl)-2-(4-hydroxyphenyl)-1,1-dihydroxybutane,
1-(2-phosphonothio-6-hydroxyphenyl)-2-(4-hydroxyphenyl)-1,1-dihydroxybutane,
1-(2-phosphonooxy-4,6-dihydroxyphenyl)-2-(4-hydroxyphenyl)-1,1-dihydroxybutane,
1-(2-phosphonoimino-4,6-dihydroxyphenyl)-2-(4-hydroxyphenyl)-1,1-dihydroxybutane,
1-(2-phosphonothio-4,6-dihydroxyphenyl)-2-(4-hydroxyphenyl)-1,1-dihydroxybutane,
1-(2-phosphonooxy-4-hydroxyphenyl)-2-(3-hydroxyphenyl)butan-1-one,
1-(2-phosphonoimino-4-hydroxyphenyl)-2-(3-hydroxyphenyl)butan-1-one,
1-(2-phosphonothio-4-hydroxyphenyl)-2-(3-hydroxyphenyl)butan-1-one,
1-(2-phosphonooxy-5-hydroxyphenyl)-2-(3-hydroxyphenyl)butan1-one,
1-(2-phosphonoimino-5-hydroxyphenyl)-2-(3-hydroxyphenyl)butan-1-one,
1-(2-phosphonothio-5-hydroxyphenyl)-2-(3-hydroxyphenyl)butan-1-one,
1-(2-phosphonooxy-6-hydroxyphenyl)-2-(3-hydroxyphenyl)butan-1-one,
1-(2-phosphonoimino-6-hydroxyphenyl)-2-(3-hydroxyphenyl)butan-1-one,
1-(2-phosphonothio-6-hydroxyphenyl)-2-(3-hydroxyphenyl)butan-1-one,
1-(2-phosphonooxy-4,6-dihydroxyphenyl)-2-(3-hydroxyphenyl)butan-1-one,
1-(2-phosphonoimino-4,6-dihydroxyphenyl)-2-(3-hydroxyphenyl)butan -one,
1-(2-phosphonothio-4,6-dihydroxyphenyl)-2-(3-hydroxyphenyl)butan-1-one,
1-(2-phosphonooxy-4-hydroxyphenyl)-2-(4-hydroxyphenyl)butan-1-one,
1-(2-phosphonoimino-4-hydroxyphenyl)-2-(4-hydroxyphenyl)butan-1-one,
1-(2-phosphonothio-4-hydroxyphenyl)-2-(4-hydroxyphenyl)butan-1-one,
1-(2-phosphonooxy-5-hydroxyphenyl)-2-(4-hydroxyphenyl)butan-1-one,
1-(2-phosphonoimino-5-hydroxyphenyl)-2-(4-hydroxyphenyl)butan-1-one, 1-(2-phosphonothio-5-hydroxyphenyl)-2-(4-hydroxyphenyl)butan-1-one,
1-(2-phosphonooxy-6-hydroxyphenyl)-2-(4-hydroxyphenyl)butan-1-one,
1-(2-phosphonoimino-6-hydroxyphenyl)-2-(4-hydroxyphenyl)butan-1-one,
1-(2-phosphonothio-6-hydroxyphenyl)-2-(4-hydroxyphenyl)butan-1-one,
1-(2-phosphonooxy-4,6-dihydroxyphenyl)-2-(4-hydroxyphenyl)butan-1-one,
1-(2-phosphonoimino-4,6-dihydroxyphenyl)-2-(4-hydroxyphenyl)butan-1-one,
1-(2-phosphonothio-4,6-dihydroxyphenyl)-2-(4-hydroxyphenyl)butan-1-one,
1-(2-phosphonooxy-4-hydroxyphenyl)-3-(3-hydroxyphenyl)butane,
1-(2-phosphonoimino-4-hydroxyphenyl)-3-(3-hydroxyphenyl)butane,
1-(2-phosphonothio-4-hydroxyphenyl)-3-(3-hydroxyphenyl)butane,
1-(2-phosphonooxy-5-hydroxyphenyl)-3-(3-hydroxyphenyl)butane,
1-(2-phosphonoimino-5-hydroxyphenyl)-3-(3-hydroxyphenyl)butane,
1-(2-phosphonothio-5-dihydroxyphenyl)-3-(3-hydroxyphenyl)butane,
1-(2-phosphonooxy-6-hydroxyphenyl)-3-(3-hydroxyphenyl)butane,
1-(2-phosphonoimino-6-hydroxyphenyl)-3-(3-hydroxyphenyl)butane,
1-(2-phosphonothio-6-hydroxyphenyl)-3-(3-hydroxyphenyl)butane,
1-(2-phosphonooxy-4,6-dihydroxyphenyl)-3-(3-hydroxyphenyl)butane,
1-(2-phosphonoimino-4,6-dihydroxyphenyl)-3-(3hydroxyphenyl)butane,
1-(2-phosphonothio-4,6-dihydroxyphenyl)-3-(3-hydroxyphenyl)butane,
1-(2-phosphonooxy-4-hydroxyphenyl)-3-(4-hydroxyphenyl)butane,
1-(2-phosphonoimino-4-hydroxyphenyl)-3-(4-hydroxyphenyl)butane,
1-(2-phosphonothio-4-dihydroxyphenyl)-3-(4-hydroxyphenyl)butane,
1-(2-phosphonooxy-5-hydroxyphenyl)-3-(4-hydroxyphenyl)butane,
1-(2-phosphonoimino-5-hydroxyphenyl)-3-(4-hydroxyphenyl)butane,
1-(2-phosphonothio-5-dihydroxyphenyl)-3-(4-hydroxyphenyl)butane,
1-(2-phosphonooxy-6-hydroxyphenyl)-3-(4-hydroxyphenyl)butane,
1-(2-phosphonoimino-6-hydroxyphenyl)-3-(4-hydroxyphenyl)butane,
1-(2-phosphonothio-6-hydroxyphenyl)-3-(4-hydroxyphenyl)butane,
1-(2-phosphonooxy-4,6-dihydroxyphenyl)-3-(4-hydroxyphenyl)butane,
1-(2-phosphonoimino-4,6-dihydroxyphenyl)-3-(4-hydroxyphenyl)butane,
1-(2-phosphonothio-4,6-dihydroxyphenyl)-3-(4-hydroxyphenyl)butane,
1-(2-phosphonooxy-4-hydroxyphenyl)-3-(3-hydroxyphenyl)-1-hydroxybutane,
1-(2-phosphonoimino-4-hydroxyphenyl)-3-(3-hydroxyphenyl)-1-hydroxybutane,
1-(2-phosphonothio-4-hydroxyphenyl)-3-(3-hydroxyphenyl)-1-hydroxybutane,
1-(2-phosphonooxy-5-hydroxyphenyl)-3-(3-hydroxyphenyl)-1-hydroxybutane,
1-(2-phosphonoimino-5-hydroxyphenyl)-3-(3-hydroxyphenyl)-1-hydroxybutane,
1-(2-phosphonothio-5-hydroxyphenyl)-3-(3-hydroxyphenyl)-1-hydroxybutane,
1-(2-phosphonooxy-6-hydroxyphenyl)-3-(3-hydroxyphenyl)-1-hydroxybutane,
1-(2-phosphonoimino-6-hydroxyphenyl)-3-(3-hydroxyphenyl)-1-hydroxybutane,
1-(2-phosphonothio-6-hydroxyphenyl)-3-(3-hydroxyphenyl)-1-hydroxybutane,
1-(2-phosphonooxy-4,6-dihydroxyphenyl)-3-(3-hydroxyphenyl)-1-hydroxybutane,
1-(2-phosphonoimino-4,6-dihydroxyphenyl)-3-(3-hydroxyphenyl)-1-hydroxybutane,
1-(2-phosphonothio-4,6-dihydroxyphenyl)-3-(3-hydroxyphenyl)-1-hydroxybutane,
1-(2-phosphonooxy-4-hydroxyphenyl)-3-(4-hydroxyphenyl)-1-hydroxybutane,
1-(2-phosphonoimino-4-dihydroxyphenyl)-3-(4-hydroxyphenyl-1-hydroxybutane,
1-(2-phosphonothio-4-dihydroxyphenyl)-3-(4-hydroxyphenyl)-1-hydroxybutane,
1-(2-phosphonooxy-5-hydroxyphenyl)-3-(4-hydroxyphenyl)-1-hydroxybutane,
1-(2-phosphonoimino-5-hydroxyphenyl)-3-(4-hydroxyphenyl)-1-hydroxybutane,
1-(2-phosphonothio-5-hydroxyphenyl)-3-(4-hydroxyphenyl)-1-hydroxybutane,
1-(2-phosphonooxy-6-hydroxyphenyl)-3-(4-hydroxyphenyl)-1-hydroxybutane,
1-(2-phosphonoimino-6-hydroxyphenyl)-3-(4-hydroxyphenyl)-1-hydroxybutane,
1-(2-phosphonothio-6-hydroxyphenyl)-3-(4-hydroxyphenyl)-1-hydroxybutane,
1-(2-phosphonooxy-4,6-dihydroxyphenyl)-3-(4-hydroxyphenyl)-1-hydroxybutane,
1-(2-phosphonoimino-4,6-dihydroxyphenyl)-3-(4-hydroxyphenyl)-1-hydroxybutane,
1-(2-phosphonothio-4,6-dihydroxyphenyl)-3-(4-hydroxyphenyl)-1-hydroxybutane,
1-(2-phosphonooxy-4-hydroxyphenyl)-3-(3-hydroxyphenyl)-1,1-dihydroxybutane,
1-(2-phosphonoimino-4-hydroxyphenyl)-3-(3-hydroxyphenyl)-1,1-dihydroxybutane,
1-(2-phosphonothio-4-hydroxyphenyl)-3-(3-hydroxyphenyl)-1,1-dihydroxybutane,
1-(2-phosphonooxy-5-hydroxyphenyl)-3-(3-hydroxyphenyl)-1,1-dihydroxybutane,
1-(2-phosphonoimino-5-hydroxyphenyl)-3-(3-hydroxyphenyl)-1,1-dihydroxybutane,
1-(2-phosphonothio-5-hydroxyphenyl)-3-(3-hydroxyphenyl)-1,1-dihydroxybutane,
1-(2-phosphonooxy-6-hydroxyphenyl)-3-(3-hydroxyphenyl)-1,1-dihydroxybutane, 1-(2-phosphonoimino-6-hydroxyphenyl)-3-(3-hydroxyphenyl)-1,1-dihydroxybutane,
1-(2-phosphonothio-6-hydroxyphenyl)-3-(3-hydroxyphenyl)-1,1-dihydroxybutane,
1-(2-phosphonooxy-4,6-dihydroxyphenyl)-3-(3-hydroxyphenyl)-1,1-dihydroxybutane,
1-(2-phosphonoimino-4,6-dihydroxyphenyl)-3-(3-hydroxyphenyl)-1,1-dihydroxybutane,
1-(2-phosphonothio-4,6-dihydroxyphenyl)-3-(3-hydroxyphenyl)-1,1-dihydroxybutane,
1-(2-phosphonooxy-4-hydroxyphenyl)-3-(4-hydroxyphenyl)-1,1-dihydroxybutane,
1-(2-phosphonoimino-4-hydroxyphenyl)-3-(4-hydroxyphenyl)-1,1-dihydroxybutane,
1-(2-phosphonothio-4-dihydroxyphenyl)-3-(4-hydroxyphenyl)-1,1-dihydroxybutane,
1-(2-phosphonooxy-5-hydroxyphenyl)-3-(4-hydroxyphenyl)-1,1-dihydroxybutane,
1-(2-phosphonoimino-5-hydroxyphenyl)-3-(4-hydroxyphenyl)-1,1-dihydroxybutane,
1-(2-phosphonothio-5-dihydroxyphenyl)-3-(4-hydroxyphenyl)-1,1-dihydroxybutane,
1-(2-phosphonooxy-6-hydroxyphenyl)-3-(4-hydroxyphenyl)-1,1-dihydroxybutane,
1-(2-phosphonoimino-6-hydroxyphenyl)-3-(4-hydroxyphenyl)-1,1-dihydroxybutane,
1-(2-phosphonothio-6-hydroxyphenyl)-3-(4-hydroxyphenyl)-1,1-dihydroxybutane,
1-(2-phosphonooxy-4,6-dihydroxyphenyl)-3-(4-hydroxyphenyl)-1,1-dihydroxybutane,
1-(2-phosphonoimino-4,6-dihydroxyphenyl)-3-(4-hydroxyphenyl)-1,1-dihydroxybutane,
1-(2-phosphonothio-4,6-dihydroxyphenyl)-3-(4-hydroxyphenyl)-1,1-dihydroxybutane,
1-(2-phosphonooxy-4-hydroxyphenyl)-3-(3-hydroxyphenyl)butan-1-one,
1-(2-phosphonoimino-4-hydroxyphenyl)-3-(3-hydroxyphenyl)butan-1-one,
1-(2-phosphonothio-4-hydroxyphenyl)-3-(3-hydroxyphenyl)butan-1-one,
1-(2-phosphonooxy-5-hydroxyphenyl)-3-(3-hydroxyphenyl)butan-1-one,
1-(2-phosphonoimino-5-hydroxyphenyl)-3-(3-hydroxyphenyl)butan-1-one,
1-(2-phosphonothio-5-hydroxyphenyl)-3-(3-hydroxyphenyl)butan-1-one,
1-(2-phosphonooxy-6-hydroxyphenyl)-3-(3-hydroxyphenyl)butan-1-one,
1-(2-phosphonoimino-6-hydroxyphenyl)-3-(3-hydroxyphenyl)butan-1-one,
1-(2-phosphonothio-6-hydroxyphenyl)-3-(3-hydroxyphenyl)butan-1-one,
1-(2-phosphonooxy-4,6-dihydroxyphenyl)-3-(3-hydroxyphenyl)butan-1-one,
1-(2-phosphonoimino-4,6-dihydroxyphenyl)-3-(3-hydroxyphenyl)butan-1-one,
1-(2-phosphonothio-4,6-dihydroxyphenyl)-3-(3-hydroxyphenyl)butan-1-one,
1-(2-phosphonooxy-4-hydroxyphenyl)-3-(4-hydroxyphenyl)butan-1-one,
1-(2-phosphonoimino-4-hydroxyphenyl)-3-(4-hydroxyphenyl)butan-1-one,
1-(2-phosphonothio-4-dihydroxyphenyl)-3-(4-hydroxyphenyl)butan-1-one,
1-(2-phosphonooxy-5-hydroxyphenyl)-3-(4-hydroxyphenyl)butan-1-one,
1-(2-phosphonoimino-5-hydroxyphenyl)-3-(4-hydroxyphenyl)butan-1-one,
1-(2-phosphonothio-5-hydroxyphenyl)-3-(4-hydroxyphenyl)butan-1-one,
1-(2-phosphonooxy-6-hydroxyphenyl)-3-(4-hydroxyphenyl)butan-1-one,
1-(2-phosphonoimino-6-hydroxyphenyl)-3-(4-hydroxyphenyl)butan-1-one,
1-(2-phosphonothio-6-hydroxyphenyl)-3-(4-hydroxyphenyl)butan-1-one,
1-(2-phosphonooxy-4,6-dihydroxyphenyl)-3-(4-hydroxyphenyl)butan-1-one,
1-(2-phosphonoimino-4,6-dihydroxyphenyl)-3-(4-hydroxyphenyl)butan-1-one,
1-(2-phosphonothio-4,6-dihydroxyphenyl)-3-(4-hydroxyphenyl)butan-1-one,
1-(2-phosphonooxy-4-hydroxyphenyl)-4-(3-hydroxyphenyl)butane,
1-(2-phosphonoimino-4-hydroxyphenyl)-4-(3-hydroxyphenyl)butane,
1-(2-phosphonothio-4-hydroxyphenyl)-4-(3-hydroxyphenyl)butane,
1-(2-phosphonooxy-5-hydroxyphenyl)-4-(3-hydroxyphenyl)butane,
1-(2-phosphonoimino-5-hydroxyphenyl)-4-(3-hydroxyphenyl)butane,
1-(2-phosphonothio-5-dihydroxyphenyl)-4-(3-hydroxyphenyl)butane,
1-(2-phosphonooxy-6-hydroxyphenyl)-4-(3-hydroxyphenyl)butane,
1-(2-phosphonoimino-6-hydroxyphenyl)-4-(3-hydroxyphenyl)butane,
1-(2-phosphonothio-6-hydroxyphenyl)-4-(3-hydroxyphenyl)butane,
1-(2-phosphonooxy-4,6-dihydroxyphenyl)-4-(3-hydroxyphenyl)butane,
1-(2-phosphonoimino-4,6-dihydroxyphenyl)-4-(3-hydroxyphenyl)butane,
1-(2-phosphonothio-4,6-dihydroxyphenyl)-4-(3-hydroxyphenyl)butane,
1-(2-phosphonooxy-4-hydroxyphenyl)-4-(4-hydroxyphenyl)butane,
1-(2-phosphonoimino-4-hydroxyphenyl)-4-(4-hydroxyphenyl)butane,
1-(2-phosphonothio-4-dihydroxyphenyl)-4-(4-hydroxyphenyl)butane,
1-(2-phosphonooxy-5-hydroxyphenyl)-4-(4-hydroxyphenyl)butane,
1-(2-phosphonoimino-5-hydroxyphenyl)-4-(4-hydroxyphenyl)butane,
1-(2-phosphonothio-5-dihydroxyphenyl)-4-(4-hydroxyphenyl)butane,
1-(2-phosphonooxy-6-hydroxyphenyl)-4-(4-hydroxyphenyl)butane,
1-(2-phosphonoimino-6-hydroxyphenyl)-4-(4-hydroxyphenyl)butane,
1-(2-phosphonothio-6-hydroxyphenyl)-4-(4-hydroxyphenyl)butane, 1-(2-phosphonooxy-4,6-dihydroxyphenyl)-4-(4-hydroxyphenyl)butane,
1-(2-phosphonoimino-4,6-dihydroxyphenyl)-4-(4-hydroxyphenyl)butane,
1-(2-phosphonothio-4,6-dihydroxyphenyl)-4-(4-hydroxyphenyl)butane,
1-(2-phosphonooxy-4-hydroxyphenyl)-4-(3-hydroxyphenyl)-1-hydroxybutane,
1-(2-phosphonoimino-4-hydroxyphenyl)-4-(3-hydroxyphenyl)-1-hydroxybutane,
1-(2-phosphonothio-4-hydroxyphenyl)-4-(3-hydroxyphenyl)-1-hydroxybutane,
1-(2-phosphonooxy-5-hydroxyphenyl)-4-(3-hydroxyphenyl)-1-hydroxybutane,
1-(2-phosphonoimino-5-hydroxyphenyl)-4-(3-hydroxyphenyl)-1-hydroxybutane,
1-(2-phosphonothio-5-hydroxyphenyl)-4-(3-hydroxyphenyl)-1-hydroxybutane,
1-(2-phosphonooxy-6-hydroxyphenyl)-4-(3-hydroxyphenyl)-1-hydroxybutane,
1-(2-phosphonoimino-6-hydroxyphenyl)-4-(3-hydroxyphenyl)-1-hydroxybutane,
1-(2-phosphonothio-6-hydroxyphenyl)-4-(3-hydroxyphenyl)-1-hydroxybutane,
1-(2-phosphonooxy-4,6-dihydroxyphenyl)-4-(3-hydroxyphenyl)-1-hydroxybutane,
1-(2-phosphonoimino-4,6-dihydroxyphenyl)-4-(3-hydroxyphenyl)-1-hydroxybutane,
1-(2-phosphonothio-4,6-dihydroxyphenyl)-4-(3-hydroxyphenyl)-1-hydroxybutane,
1-(2-phosphonooxy-4-hydroxyphenyl)-4-(4-hydroxyphenyl)-1-hydroxybutane,
1-(2-phosphonoimino-4-hydroxyphenyl)-4-(4-hydroxyphenyl)-1-hydroxybutane,
1-(2-phosphonothio-4-dihydroxyphenyl)-4-(4-hydroxyphenyl)-1-hydroxybutane,
1-(2-phosphonooxy-5-hydroxyphenyl)-4-(4-hydroxyphenyl)-1-hydroxybutane,
1-(2-phosphonoimino-5-hydroxyphenyl)-4-(4-hydroxyphenyl)-1-hydroxybutane,
1-(2-phosphonothio-5-hydroxyphenyl)-4-(4-hydroxyphenyl)-1-hydroxybutane,
1-(2-phosphonooxy-6-hydroxyphenyl)-4-(4-hydroxyphenyl)-1-hydroxybutane,
1-(2-phosphonoimino-6-hydroxyphenyl)-4-(4-hydroxyphenyl)-1-hydroxybutane,
1-(2-phosphonothio-6-hydroxyphenyl)-4-(4-hydroxyphenyl-1-hydroxybutane,
1-(2-phosphonooxy-4,6-dihydroxyphenyl)-4-(4-hydroxyphenyl)-1-hydroxybutane,
1-(2-phosphonoimino-4,6-dihydroxyphenyl)-4-(4-hydroxyphenyl)-1-hydroxybutane,
1-(2-phosphonothio-4,6-dihydroxyphenyl)-4-(4-hydroxyphenyl)-1-hydroxybutane,
1-(2-phosphonooxy-4-hydroxyphenyl)-4-(3-hydroxyphenyl)-1,1-dihydroxybutane,
1-(2-phosphonoimino-4-hydroxyphenyl)-4-(3-hydroxyphenyl)-1,1-dihydroxybutane,
1-(2-phosphonothio-4-hydroxyphenyl)-4-(3-hydroxyphenyl)-1,1-dihydroxybutane,
1-(2-phosphonooxy-5-hydroxyphenyl)-4-(3-hydroxyphenyl)-1,1-dihydroxybutane,
1-(2-phosphonoimino-5-hydroxyphenyl)-4-(3-hydroxyphenyl)-1,1-dihydroxybutane,
1-(2-phosphonothio-5-hydroxyphenyl)-4-(3-hydroxyphenyl)-1,1-dihydroxybutane,
1-(2-phosphonooxy-6-hydroxyphenyl)-4-(3-hydroxyphenyl)-1,1-dihydroxybutane,
1-(2-phosphonoimino-6-hydroxyphenyl)-4-(3-hydroxyphenyl)-1,1-dihydroxybutane,
1-(2-phosphonothio-6-hydroxyphenyl)-4-(3-hydroxyphenyl)-1,1-dihydroxybutane,
1-(2-phosphonooxy-4,6-dihydroxyphenyl)-4-(3-hydroxyphenyl)-1,1-dihydroxybutane,
1-(2-phosphonoimino-4,6-dihydroxyphenyl)-4-(3-hydroxyphenyl)-1,1-dihydroxybutane,
1-(2-phosphonothio-4,6-dihydroxyphenyl)-4-(3-hydroxyphenyl)-1,1-dihydroxybutane,
1-(2-phosphonooxy-4-hydroxyphenyl)-4-(4-hydroxyphenyl)-1,1-dihydroxybutane,
1-(2-phosphonoimino-4-hydroxyphenyl)-4-(4-hydroxyphenyl)-1,1-dihydroxybutane,
1-(2-phosphonothio-4-dihydroxyphenyl)-4-(4-hydroxyphenyl)-1,1-dihydroxybutane,
1-(2-phosphonooxy-5-hydroxyphenyl)-4-(4-hydroxyphenyl)-1,1-dihydroxybutane,
1-(2-phosphonoimino-5-hydroxyphenyl)-4-(4-hydroxyphenyl)-1,1-dihydroxybutane,
1-(2-phosphonothio-5-dihydroxyphenyl)-4-(4-hydroxyphenyl)-1,1-dihydroxybutane,
1-(2-phosphonooxy-6-hydroxyphenyl)-4-(4-hydroxyphenyl)-1,1-dihydroxybutane,
1-(2-phosphonoimino-6-hydroxyphenyl)-4-(4-hydroxyphenyl)-1,1-dihydroxybutane,
1-(2-phosphonothio-6-hydroxyphenyl)-4-(4-hydroxyphenyl)-1,1-dihydroxybutane,
1-(2-phosphonooxy-4,6-dihydroxyphenyl)-4-(4-hydroxyphenyl)-1,1-dihydroxybutane,
1-(2-phosphonoimino-4,6-dihydroxyphenyl)-4-(4-hydroxyphenyl)-1,1-dihydroxybutane,
1-(2-phosphonothio-4,6-dihydroxyphenyl)-4-(4-hydroxyphenyl)-1,1-dihydroxybutane,
1-(2-phosphonooxy-4-hydroxyphenyl)-4-(3-hydroxyphenyl)butan1-one,
1-(2-phosphonoimino-4-hydroxyphenyl)-4-(3-hydroxyphenyl)butan-1-one,
1-(2-phosphonothio-4-hydroxyphenyl)-4-(3-hydroxyphenyl)butan-1-one,
1-(2-phosphonooxy-5-hydroxyphenyl)-4-(3-hydroxyphenyl)butan-1-one,
1-(2-phosphonoimino-5-hydroxyphenyl)-4-(3-hydroxyphenyl)butan-1-one,
1-(2-phosphonothio-5-hydroxyphenyl)-4-(3-hydroxyphenyl)butan-1-one,
1-(2-phosphonooxy-6-hydroxyphenyl)-4-(3-hydroxyphenyl)butan-1-one,
1-(2-phosphonoimino-6-hydroxyphenyl)-4-(3-hydroxyphenyl)butan-1-one,
1-(2-phosphonothio-6-hydroxyphenyl)-4-(3-hydroxyphenyl)butan-1-one,
1-(2-phosphonooxy-4,6-dihydroxyphenyl)-4-(3-hydroxyphenyl)butan-1-one,
1-(2-phosphonoimino-4,6-dihydroxyphenyl)-4-(3-hydroxyphenyl)butan-1-one, 1-(2-phosphonothio-4,6-dihydroxyphenyl)-4-(3-hydroxyphenyl)butan-1-one, 1-(2-phosphonooxy-4-hydroxyphenyl)-4-(4-hydroxyphenyl)butan-1-one, 1-(2-phosphonoimino-4-hydroxyphenyl)-4-(4-hydroxyphenyl)butan-1-one, 1-(2-phosphonothio-4-dihydroxyphenyl)-4-(4-hydroxyphenyl)butan-1-one, 1-(2-phosphonooxy-5-hydroxyphenyl)-4-(4-hydroxyphenyl)butan-1-one, 1-(2-phosphonoimino-5-hydroxyphenyl)-4-(4-hydroxyphenyl)butan-1-one, 1-(2-phosphonothio-5-hydroxyphenyl)-4-(4-hydroxyphenyl)butan-1-one, 1-(2-phosphonooxy-6-hydroxyphenyl)-4-(4-hydroxyphenyl)butan-1-one, 1-(2-phosphonoimino-6-hydroxyphenyl)-4-(4-hydroxyphenyl)butan-1-one, 1-(2-phosphonothio-6-hydroxyphenyl)-4-(4-hydroxyphenyl)butan-1-one, 1-(2-phosphonooxy-4,6-dihydroxyphenyl)-4-(4-hydroxyphenyl)butan-1-one, 1-(2-phosphonoimino-4,6-dihydroxyphenyl)-4-(4-hydroxyphenyl)butan-1-one, 1-(2-phosphonothio-4,6-dihydroxyphenyl)-4-(4-hydroxyphenyl)butan-1-one, alkylated analogs (alkyl groups on the alkylenyl connector or on the two phenyl groups), or amino analogs (hydroxy groups replaced by amino groups), and the like, and the pharmaceutically acceptable salts thereof.

The compounds of the present invention can be synthesized using standard organic synthetic procedures. Such procedures comprise: contacting a compound of the formula $E^1—A^1—Z—R^1—A^2—(E)_n$ or a pharmaceutically acceptable salt thereof with an $H_3PO_4$ or $P_2O_5$ source to yield any on of the the compounds (I) through $(I_g)$; or if R1 is an unsaturated group, hydrogenating it with a H or Tritium source; or cleaving any protecting groups in a compound of Formula I to liberate free hydroxyl or phosphate groups; or converting a compound of Formula I to a pharmaceutically acceptable salt; or converting a salt of a compound of Formula I to a compound of Formula I; or converting a salt of a compound of Formula I to a pharmaceutically acceptable salt of a compound of Formula I; or converting a substituent in $A^1$ or $A^2$ to another substituent. More specifically, the compounds of Formula (I) through $(I_g)$ are prepared as follows: an aryl group bearing an amino group, a hydroxy group, or a mercapto group and preferably bearing a separate hydrophilic group is reacted with a $ZR^1$ substituted second aryl group to form a $ZR^1$ linked diaryl compound. The $ZR^1$ linked diaryl compound is then reacted with phosphoric acid or phosphorus pentoxide to generate compounds of formulas (I) and (Ia) through (Id). If Z is a carbonyl group as in formulas (Ie) through (Ig), then Friedel-Crafts acylation can be used to attach the acid chloride of the $ZR^1$ aryl reagent to the aryl group bearing an amino group, a hydroxy group, or a mercapto group. If Z is a single bond, the Friedel-Crafts alkylation can be used to attach the chloro-$ZR^1$ aryl reagent to the aryl group bearing the amino, hydroxy or mercapto group.

Compounds of formula Ie are a particularly preferred class of compounds. When $R^1$ is $—CH_2CH_2—$, the phosphonooxy feature is at the 2'-position and the hydrophilic groups are 4, 4', and 6'-hydroxy, the material is 2'-phosphophloretin.

When $R^1$ is $—CH_2—$, the compound of formula Ie can be prepared from hydrophilically substituted salicylic acids. Substituted salicylic acids are compounds known to a person of ordinary skill in the art, and protected hydrophilically substituted salicylic acids (note that one hydroxy group, for example the salicylic acid hydroxy group itself if a 2'-phosphonooxy compound is desired, is not protected) may readily be prepared by methods known in the art. These compounds they can be transformed to substituted 2-phenyl-2'-hydroxyacetophenones according to Rubottom and Kim, *J. Org. Chem.* 1983, 48, 1550; where a protected hydrophilically substituted benzyllithium or benzylmagnesium compound is reacted with the protected hydrophilically substituted salicylic acid in the presence of trimethylsilyl chloride. A suitable protected hydrophilically substituted benzyllithium is, for example, 4-(benzyloxy)benzyllithium, where the benzyl protecting group can later be removed to yield a 4-hydroxy compound. The resulting 2-phenyl-2'-hydroxyacetophenone compound is reacted with a base, such as sodium or potassium hydride, or an organic amine base such as pyridine or trimethylamine, and a chlorophosphate diester, and then deprotected to yield the compound of formula (Ie). When the chlorophosphate diester is dibenzyl chlorophosphate and the protecting groups are benzyl groups, hydroxyl and phosphate, respectively, are liberated upon exposure to deprotection conditions such as hydrogen gas or ammonium formate in the presence of palladium on carbon, platinum(IV) oxide, or other like heterogeneous catalysts.

Compounds of formula (Ie) where $R^1$ is a linear or branched $C_3–C_{20}$ group of which the two carbons nearest the carbonyl are $—CH_2CH_2—$ can be prepared from hydrophilically substituted salicylic acid esters. These salicylic acid esters may be converted to triphenylphosphoranes by reaction with triphenylphosphonium iodide and a base such as butyllithium according to Zammattio et al. *Synthesis* 1992, 375. These triphenylphosphoranes react predictably with aldehydes as illustrated in Fieser & Fieser *Reagents for Organic Synthesis* 6, 267 and 8, 234, to give unsaturated ketones analogous to those seen in the first step of FIG. 2. Suitable aldehydes are ω-(protected hydrophilically substituted phenyl)-α-alkylaldehydes. The hydroxy group of the product unsaturated ketone can then be treated with a base in an aprotic solvent and a chlorophosphate, as discussed in the previous paragraph (cf. Silverberg et al. *Tetrahedr. Lett.* 1996, 37, 771). The use of the Silverberg procedure allows for hydrogenolysis (treatment with hydrogen gas or ammonium formate in the presence of palladium on carbon, platinum (IV) oxide, or other like heterogeneous catalysts) of the protected hydrophilic groups and well as liberation of the aryl phosphate of formula (Ie). Alternatively, dimethyl or diethyl chlorophosphate can be employed. The product (dimethyl or diethyl) aryl phosphate can then deprotected with trimethylsilyl bromide in a compatible solvent such as dichloromethane or chloroform.

2'-PP may also conveniently be prepared from phlorizin (phloretin-2'-β-glucoside).

Compositions and Administration

The present invention also relates to a medication comprising a therapeutically effective amount of at least one compound of formula (I) in a suitable carrier.

A "therapeutically effective amount" of compound I is defined herein as the amount required to achieve the desired positive effect with respect to progression of renal failure being treated. The effective amount will be determined in part based on the intended goal, for example, (i) inhibition of Na-dependent phosphate uptake or (ii) reducing serum PTH, calcium, calcitriol, and phosphate.

The present invention also relates to a method of reducing the blood phosphate level in an animal, including a human, by administering to that animal a therapeutically effective amount of at least one compound of formula (I) or a medication containing it, where the administration can be continuous or discontinuous, oral or parenteral administration.

Oral administration includes, without limitation, administering the compound within a medication such as a pill, caplet, gel-capsule, capsule, chewable tablet, liquid, drink or other form capable of being swallowed by an animal. Parenteral administration includes, without limitation, administering the compound within a medication intravenously, intra-arterially, intramuscularly, or the like by injection for non-continuous administration or by a stent or the like for continuous administration. Preferably, the compound of the present invention is administered orally.

Thus, pharmaceutical compositions of or medications comprising the compounds of formula I, or derivatives thereof, may be formulated as solutions, crystalline, amorphous or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration. It may be desirable to add excipients such as polyvinylpyrrolidinone, gelatin, hydroxycellulose, acacia, polyethylene glycol, mannitol, sodium chloride or sodium citrate. Alternatively, these compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, soybean oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glycerol monostearate or glyceryl distearate, alone or with a wax. The amount of solid carrier varies but, preferably, will be between about 5 mg to about 500 mg per dosage unit. The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of syrup, elixir, emulsion or an aqueous or non-aqueous suspension. Such a liquid formulation may be administered directly p.o. or filled into a soft gelatin capsule.

The invention compounds may be administered by any route suitable to the subject being treated and the nature of the subject's condition. Alternative routes of administration include administration by injection, including intravenous, intraperitoneal, intramuscular, and subcutaneous injection, by transmucosal or transdermal delivery, through topical applications, nasal spray, suppository and the like or may be administered orally. It also may be desired to perform continuous perfusion over hours or days via a catheter to a disease site like the intestinal region. Suitable formulations for each of these methods of administration may be found, for example, in *Remington's Pharmaceutical Sciences*, latest edition, Mack Publishing Company, Easton, Pa.

Regardless of the route of administration, the compound should be given in an amount sufficient to provide a therapeutic concentration of a compound of formula (I) in the intestinal region including the apical membrane involved in sodium-mediated phosphate transportation across the intestinal membrane. The exact amount will depend on the nature of the medication and the required dosage. If the compound of formula (I) is administered orally so that it is exposed to the digestive processes of the digestive tract, then the amount must be sufficient to account for the loss of compound during digestion. On the other hand, if the compound of formula (I) is not exposed or only minimally exposed to the digestive processes of the digestive tract, then a smaller amount of the compound can be used.

The effective dosages of these compounds were determined in rat studies in mL of a micromolar solution of the phosphate transport inhibitor in an aqueous medium such as water, dextrose-containing solution, or the like. In humans and other larger animals, medications are usually administered in a gram-based dosage per kilogram of body weight. Using the rat dosages as guidelines, the compounds of the present invention will generally be orally administered at a dose of about 0.1 $\mu$g/Kg to about 100 $\mu$g/Kg preferably about 0.5 $\mu$g/Kg to about 50 $\mu$g/Kg, and particularly about 1 $\mu$g/Kg to about 15 $\mu$g/Kg, for 2'-PP or inhibitors having similar efficacy to 2'-PP. For NHPP or other compounds with similar efficacy to NHPP, the oral dose will generally about 0.1 $\mu$g/Kg to about 250 $\mu$g/Kg, preferably about 0.5 $\mu$g/Kg to about 150 $\mu$g/Kg, particularly about 10 $\mu$g/Kg to 100 $\mu$g/Kg. If administered directly into the intestines, the dosages can be reduced somewhat, but they should remain within about 90% of the oral dose. Of course, higher and lower doses can be used, provided one recognizes the medical consequences of low level administration (low efficacy) and high level administration (risk of occurrence of side effects or overdosage). A person of ordinary skill in the art will have no difficulty, having regard to that knowledge and this disclosure, in determining a suitable oral dose.

When administered parenterally, the compounds of the present invention do not inhibit dietary phosphate uptake directly from within the digestive tract, but interact with the phosphate control mechanisms in the body. Phosphate control is generally thought to occur in the kidneys and in the parathyroid gland. The exact method of inhibition of phosphate of these inhibitors when injected is less well understood, and under certain conditions, the compounds of the present invention may be used to increase phosphate levels in the blood and other bodily fluids.

The compounds of this invention can be mixed with carriers, binders and inert materials so that the compounds can be formed into pills, gel-capsule, capsule, chewable tablet, liquid, drink or other form capable of being swallowed by an animal or human. In solid form (pills, gel-caps, etc.), the compounds of the present invention can be formulated into such oral medications as described in U.S. Pat. Nos. 4,824,678, 4,871,546 and 5,292,518, incorporated by reference, or by any other tableting process well known in the art. For parenteral medications, the compounds of the present invention can be combined with any standard IV or injection carrier including saline, dextrose solutions, serum, whole blood, or any other carrier well-known in the manufacture or administration of parenteral medications.

EXAMPLES

The following non-limiting examples are included to illustrate the methods of making the compounds of this invention and to present certain characteristics of the compounds.

Example 1

Synthesis of 2'-phosphophloretin (2'-PP)

The synthesis of 2'-PP, shown schematically in FIG. 1, was performed, with minor modifications, according to the method described in Wilson, A. N., and Harris, S. A. (1951) *J. Am. Chem. Soc.* 73: 4693–694, incorporated herein by reference. The reaction between phloretin and anhydrous phosphoric acid was allowed to proceed over $P_2O_5$ under vacuum for 3 days at 23° C. The products were separated using acid-washed charcoal, neutralized with KOH to form the mono-potassium salt, and resolved by thin layer chromatography. The partially dried product was recrystallized from ethanol 3 times. NMR and mass spectrometry were consistent with the structure shown in FIG. 1.

The 2'-PP was analyzed by thin layer chromatography, IR and NMR. Thin layer chromatography was performed on Kieselguhr using isobutyl alcohol/glacial acetic acid/water (6:2:2) and toluene/chloroform/acetone (5:3:2). Spots were visualized with Paul's reagent for the determination of phenolic groups, and 1% ammonium molybdate and 1% stannous chloride in 10% HCl for the determination of phosphate.

IR spectra were performed on a Beckman instrument. The spectra were compared with the spectrum of the phloretin used in the synthesis and with the spectrum of phloretin in Aldrich's Catalogue of IR Spectra. The following peaks were observed:

aromatic OH and aromatic rings—broad peak from 3500–3000 $cm^{-1}$ weak overtone from 2000–1600 $cm^{-1}$ C═O-strong band at 1680 $cm^{-1}$ C═C-1550$cm^{-1}$ C—O-1220 $cm^{-1}$ P—O(aromatic)-1260 $cm^{-1}$–1160 $cm^{-1}$ P═O-1150 $cm^{-1}$ P—OH -1040 $cm^{-1}$–950 $cm^{-1}$ CH bend -800 $cm^{-1}$.

Example 2

Synthesis of 2'-PP or tritiated 2'-PP from 3,5-dimethoxyphenol 2 g of dry 3,5-dimethoxyphenol, 2.2 g of dry $AlCl_3$ and 2.5 g of 4-hydroxycinnamyl chloride were suspended in 50 mL of DMSO. The mixture was brought to a boil and maintained at reflux for 2 hours. The mixture was cooled, and yellow needles of 1-(2,4-dimethoxy-6-hydroxyphenyl)-3-(4-hydroxyphenyl)-prop-2-en-1-one precipitated out of solution. The yield was approximately 80%. The needles were washed twice with 100 mL of methanol and recrystallized.

0.5 g of the unsaturated ketone, 20 mL methanol, and 1 g of palladium on carbon were mixed, and to the mixture was added 50 µL of sodium borohydride. The reaction mixture was placed under vacuum, and the reaction continued for 30 minutes or until hydrogen evolution ceased. The reaction mixture was diluted with 100 mL of water. Pale yellow to tan crystals of 1-(2,4-dimethoxy-6-hydroxyphenyl)-3-(4-hydroxyphenyl)-propan-1-one formed. The crystals were obtained from the mixture via centrifugation at 1000×g for 10 minutes. The crystals were resuspended in water, and centrifugation was repeated. The use of tritiated sodium borohydride gives analogs of this compound tritiated at the 2 and/or 3-positions of the propanone chain.

The 1-(2,4-dimethoxy-6-hydroxyphenyl)-3-(4-hydroxyphenyl)-propan-1-one was converted to 1-(2-phosphonooxy-4,6-dimethoxyphenyl)-3-(4-hydroxyphenyl)-propan-1-one by the method of Example 1; then deprotected under acidic conditions to yield 2'-PP [or tritium labeled 2'-PP if tritiated sodium borohydride was used].

Example 3

Synthesis of 2'-PP from Phlorizin

This synthetic approach is based on the syntheses reported in Muller, A. and Robertson, A. (1933) *J. Chem. Soc.*, 1170 and Wilson, A. N. and Harris, S. A. (1951) *J. Biol. Chem.*, 73: 4693.

1 g of phlorizin, 10 mL of acetic anhydride, and 0.82 g (0.01 mol) of sodium acetate were reacted at 100° C. for 6 hrs. The reaction mixture was cooled and the triacetate derivative of phlorizin precipitated from the solution in the form of a crystalline solid. The crystalline solid was separated by filtration, dissolved in 50 mL of hot methanol, and re-crystallized twice from hot methanol. The reaction yielded 0.6 g of the triacetate.

0.3 g of the triacetate and 1.3 mL of 0.2 M sulfuric acid in 100 mL of water were heated to reflux and refluxed for 3 hrs. The reaction mixture was cooled yielding the triacetate of phloretin in about a 45% yield.

A phosphorylating solution was made by slowly adding 5 g of phosphorus pentoxide to 8.5 g of 85% phosphoric acid. The reaction is very exothermic, and cooling was used if needed. The addition occurred over approximately 100 minutes (0.5 g per 10 minutes). The phloretin triacetate was added, and the reaction mixture was placed under vacuum for 5 days. As the reaction proceeded, the solution became viscous.

The phosphato-phloretin triacetate of the previous step was diluted with 50 mL of ice water and neutralized with either potassium carbonate or potassium hydroxide until the pH by pH paper was between 8 and 8.5. 10 g of Darco activated charcoal was added, and the solution was centrifuged at 1000×g for 10 minutes. The supernatant was removed. The charcoal was washed once and centrifuged again, and the supernatants were combined and lyophilized, yielding 2'-PP.

Example 4

Synthesis of 2'-PP from phlorizin

An N,N-dimethylformamide (70 mL) suspension of phlorizin (4.2 g, 8.9 mmol) and potassium carbonate (6.2 g, 45 mmol) was treated with benzyl bromide (5.3 mL, 45 mmol) and stirred at ambient temperature (rt). After 3 days, the volatiles were removed by distillation under vacuum. The residue was cooled to rt and partitioned between water (200 mL) and ethyl acetate (4×100 mL). The organic extracts were combined, and the volatiles were removed with a rotary evaporator. The tan solid residue was dissolved in 1,4-dioxane (400 mL) and 1 M aqueous hydrochloric acid (4 mL) and heated to reflux for 2.5 h. Upon cooling, the reaction mixture was diluted with aqueous sodium bicarbonate (250 mL) and extracted with ethyl acetate (4×100 mL). The combined organic layers were washed with fresh water, then with brine, and stored over magnesium sulfate. The mixture was filtered, and the filtrate was reduced to a volume of ca. 50 mL and aged at rt. After 2 days, 4',6',4-tri-O-benzyl-phloretin was obtained as a white solid following vacuum filtration and drying (5.6 g): mp 106–107° C.; $^1$H NMR (300 Hz, CDCl$_3$) δ 13.6 (s, 1 H), 7.46–7.29 (m, 15 H), 6.86 (d, J=8.8 Hz, 2 H), 6.80 (d, J=8.8 Hz, 2 H), 6.35 (d, J=2.3 Hz, 1 H), 6.21 (d, J=2.3 Hz, 1 H), 5.17 (s, 2 H), 5.14 (s, 2 H), 5.07 (s, 2 H), 3.20 (t, J=7.1 Hz, 2 H), 2.73 (t, J=7.2 Hz, 2 H); EIMS m/z 544 (M$^+$).

4',6',4-tri-O-benzyl-phloretin (1.18 g, 2.2 mmol) was dissolved in N,N-dimethylacetamide (10 mL) and cooled to 0° C. Sodium hydride (95%, 70 mg, 2.75 mmol) was added in one portion, and the mixture was stirred at rt. After 1 h, the solution was recooled to 0° C., treated with carbon tetrachloride (1.05 mL, 11 mmol) and then dibenzylphosphite (90%, 0.72 mL, 3.3 mmol, dissolved in 3 mL N,N-dimethylacetamide and added over 10 min). The resulting solution was stirred for an additional 15 min, treated with pH 4 buffer and partitioned between water and 1:1 hexane:ethyl acetate (4×50 mL). The combined organic extracts were washed with brine and stored over sodium sulfate. Following filtration and removal of the volatiles, the filtrate residue was subjected to silica gel chromatography using 5% ethyl acetate: 25% dichloromethane: 70% hexanes as the eluant. The desired di-benzyl phosphate ester was obtained as an oil (880 mg, 1.1 mmol): $^1$H NMR (300 Hz, CDCl$_3$) δ 7.42–7.29 (m, 25 H), 6.93 (d, J=8.8 Hz, 2 H), 6.78 (d, J=8.8 Hz, 2 H), 6.63 (dd, J=1.2, 2.0 Hz, 1 H), 6.40 (dd, J=0.6, 2.1 Hz, 1 H), 5.06 (s, 2 H), 5.04 (s, 2 H), 4.97 (d, J=4.8 Hz, 4 H), 4.87 (s, 2 H), 3.03 (t, J=8.4 Hz, 2 H), 2.83 (t, J=8.2 Hz, 2 H); ESMS m/z 805 (M+H).

The oil was dissolved in ethyl acetate (55 mL) and added to 10% palladium on carbon (150 mg), and the resulting suspension was stirred under 1 atmosphere of hydrogen gas for 75 min. The mixture was filtered through Celite, the Celite cake washed with fresh ethyl acetate (50 mL) and the volatiles were removed from the combined filtrate in vacuo. 2'-PP was obtained as an off-white powder (369 mg): mp 170.0–170.5° C.; $^1$H NMR (300 Hz, d$_6$-DMSO) δ 13.0 (s, 1 H), 10.7 (br.s, 1 H), 9.2 (br.s, 1 H), 7.03 (d, J=8.6 Hz, 2 H), 6.64 (d, J=8.4 Hz, 2 H), 6.63 (dd, J=1.2, 2.1 Hz, 1 H), 6.04 (d, J=2.4 Hz, 1 H), 3.27 (t, J=7.2 Hz, 2 H), 2.77 (t, J=7.6 Hz, 2 H); $^{31}$P NMR δ −4.3; ESMS m/z 355 (M+H). Analysis calculated for C$_{15}$H$_{15}$O$_8$P: C, 50.86; H, 4.27; found: C, 50.67; H, 4.37.

Example 5

Synthesis of [$^3$H]2'-phosphophloretin ([$^3$H]2'-PP)

Figure 2:
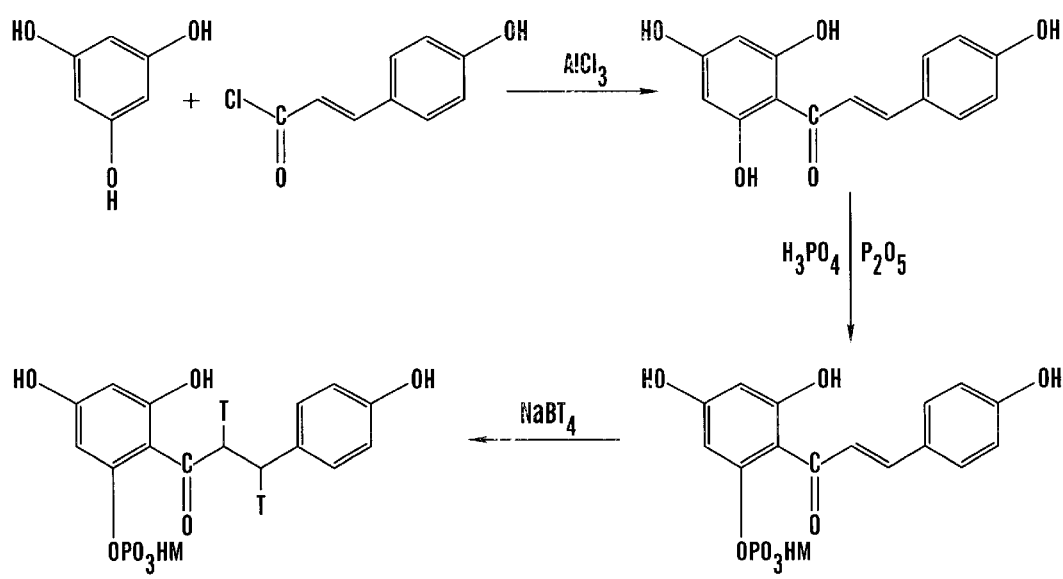
FIG. 2 shows a synthetic scheme for [$^3$H]2'-phosphophloretin ([$^3$H]2'-PP).

[$^3$H]2'-PP was synthesized using a Friedel-Crafts acylation reaction between phloroglucinol and 4-hydroxycinnamyl chloride catalyzed by AlCl$_3$ in an appropriate solvent, followed by phosphorylation with phosphoric acid, and NaB[$^3$H$_4$](NaBT$_4$) reduction in an appropriate solvent as shown in FIG. 2, and analogously to Example 9 below. Of course, any strong Lewis acid can be used in place of AlCl$_3$, as well as other reducing agents. This scheme is similar to that described for the synthesis of phlorizin described in Canter, F. W., Curd, H., and Robertson, A. (1931) *J. Chem. Soc.* (London) 1245–265; Hosang, M., Vasella, A., and Semenza, G. (1981) *Biochemistry* 20: 5844–854; and Zemplen, G. and Bognar, R. (1942) *Chem. Ber.* 75B: 1040–43, incorporated herein by reference. This synthesis differs from the scheme for synthesis of 4-azido-phlorizin as described in Hosang, M., Vasella, A and Semenza, G (1981) *Biochemistry* 20: 5844–854, in that tritiated NaBH$_4$ was used to reduce the acetopropyl side chain off benzene ring 2. The specific activity of the [$^3$H] 2'-PP produced was 5 Ci/mmole or approximately 15 times that reported for [$^3$H]4-azidophlorizin synthesized by ring reduction as described in Gibbs, E. M., Hosang, M, Reber, B. F. X., Semenza, G. and Diedrich, D. F. (1982) *Biochim. Biophys. Acta* 688: 547–556.

Example 6

Synthesis of 2'-aminophosphophloretin (NHPP)

Figure 3:
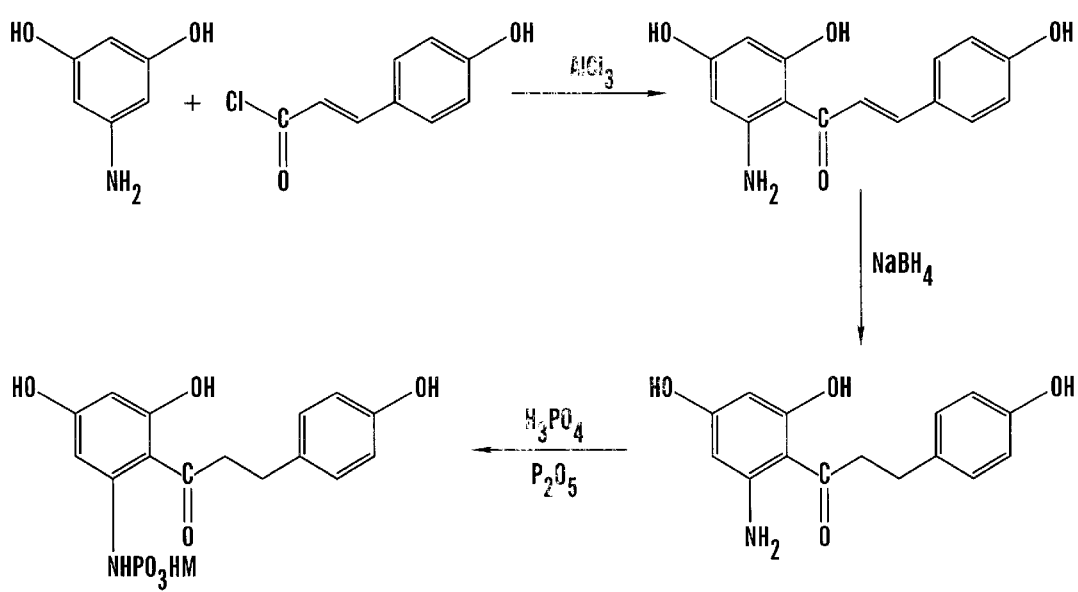
FIG. 3 shows a synthetic scheme for 2'-aminophosphophloretin (NHPP).

The synthesis of NHPP is shown schematically in FIG. 3 and involves the Friedel-Crafts acylation reaction between 3,5-dihydroxyaniline and 4-hydroxycinnamyl chloride catalyzed by AlCl$_3$ in an appropriate solvent. The unsaturation in the propyl connecting moiety is then reduced with NaBH$_4$ in an appropriate solvent. Of course, any reducing agent can be used as well provided that the reducing agent does not reduce other moieties in the process. The reduced intermediate is then reacted with anhydrous phosphoric acid over P$_2$O$_5$ under vacuum for 3 days at 23° C., in the same manner as in the synthesis of 2'-PP described above.

Example 7

Synthesis of NHPP from Dimethoxyphenol 2 g of dry 3,5-dimethoxyphenol was dissolved in 25 mL dry THF and cooled in an ice bath. To this solution was added 2.25 g of diethylazodicarboxylate (DEAD), 6 g of triphenylphosphine and 1 mL of ammonium chloride (NH$_4$Cl). The mixture was stirred for 20 minutes. The mixture was warmed to room temperature and stirred for an additional 30 minutes. Silica gel was added to remove DEAD, triphenylphosphine, and excess ammonia, yielding 3,5-dimethoxyaniline.

2 g of dry 3,5-dimethoxyaniline, 2.2 g of dry AlCl$_3$, and 2.5 g of 4-hydroxycinnamyl chloride were added to 50 mL of DMSO. The mixture was brought to a boil and maintained at reflux for 2 hours. The mixture was cooled, and yellow needles of 1-(2,4-dimethoxy-6-aminophenyl)-3-(4-hydroxyphenyl)-prop-2-en-1-one precipitated out of solution. The yield was approximately 80%. The needles were washed twice with 100 mL of methanol and recrystallized.

0.5 g of 1-(2,4-dimethoxy-6-aminophenyl)-3-(4-hydroxyphenyl)-prop-2-en-1-one, 20 mL methanol, and 1 g of palladium on carbon were mixed; and to the mixture was added 50 µL of sodium borohydride and placed under vacuum. The reaction was continued for 30 minutes or until hydrogen evolution ceased. The reaction mixture was diluted with 100 mL of water. Pale yellow to tan crystals of 1-(2,4-dimethoxy-6-aminophenyl)-3-(4-hydroxyphenyl)-propan-1-one formed. The crystals were obtained from the mixture via centrifugation at 1000×g for 10 minutes. The crystals were resuspended in water, and centrifugation was repeated.

The 1-(2,4-dimethoxy-6-aminophenyl)-3-(4-hydroxyphenyl)-propan-1-one was converted to 1-(2-phosphonamino-4,6-dimethoxyphenyl)-3-(4-hydroxyphenyl)-propan-1-one by the method of Example 1.

The use of tritiated sodium borohydride results in the preparation of tritiated NHPP.

Example 8

Synthesis of 3-azido-2'-phosphophloretin (AZPP)

Figure 4:
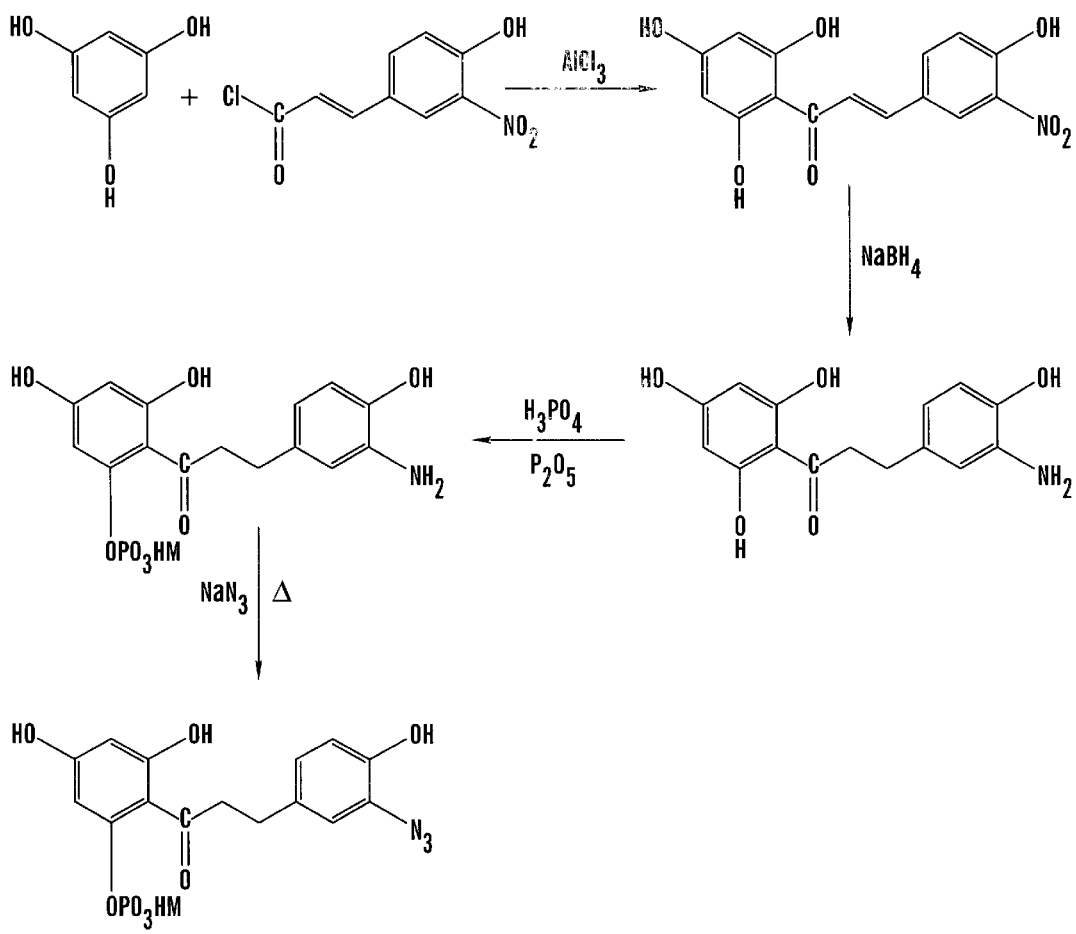
FIG. 4 shows another synthetic scheme for 2'-PP.

The synthesis of AZPP is shown schematically in FIG. 4 and involves the Friedel-Crafts acylation reaction between phloroglucinol and 4-hydroxy-3-nitrocinnamyl chloride catalyzed by AlCl$_3$ in an appropriate solvent. The unsaturation in the propyl connecting moiety and the nitro group are then reduced with $NaBH_4$ in an appropriate solvent. Of course, any reducing agent can be used as well, provided that the reducing agent does not reduce other moieties in the process. The reduced intermediate is then reacted with anhydrous phosphoric acid over $P_2O_5$ under vacuum for 3 days at 23° C., in the same manner as in the synthesis of 2'-PP described above. The 3-amino-2'-phosphophloretin was then reacted with sodium azide in an appropriate solvent with heating to form AZPP.

Example 9

Synthesis of 4-azido-2'-PP and tritiated analogs

This synthetic approach is based on the syntheses reported in Muller, A. and Robertson, A. (1933) *J. Chem. Soc.*, 1170 and Wilson, A. N. and Harris, S. A. (1951) *J. Biol. Chem.*, 73: 4693.

2 g of dry phloroglucinol, 2.2 g of dry $AlCl_3$, and 2.5 g of 4-nitrocinnamyl chloride were suspended in 50 mL of DMSO. The mixture was brought to a boil and maintained at reflux for 2 hours. The mixture was cooled, and yellow needles of 1-(2,4,6-trihydroxy)-3-(4-nitrophenyl)-prop-2-en-1-one precipitated out of solution. The yield was approximately 80%. The needles were washed twice with 100 mL of methanol and recrystallized.

0.5 g of 1-(2,4,6-trihydroxy)-3-(4-nitrophenyl)-prop-2-en-1-one, 20 mL of methanol, and 1 g of palladium on carbon were mixed; and to the mixture was added 50 μL of tritiated sodium borohydride and placed under vacuum. The reaction was continued for 30 minutes or until hydrogen evolution ceased. The reaction mixture was diluted with 100 mL of water. Pale yellow to tan crystals of [$^3$H]1-(2,4,6-trihydroxy)-3-(4-aminophenyl)-propan-1-one formed. The crystals were obtained from the mixture via centrifugation at 1000×g for 10 minutes. The crystals were resuspended in water, and centrifugation was repeated.

The [$^3$H]1-(2,4,6-trihydroxy)-3-(4-aminophenyl)-propan-1-one was converted to [$^3$H]1-(2-phosphonooxy-4,6-trihydroxy)-3-(4-aminophenyl)-propan-1-one by the method of Example 1.

0.2 g of [$^3$H]1-(2-phosphonooxy-4,6-trihydroxy)-3-(4-aminophenyl)-propan-1-one was combined with 80% acetic acid and 50 mg of sodium nitrite, and the mixture was stirred for 10 minutes. 50 mg of sodium azide in ice cold water was added to the mixture. The reaction mixture was stirred on ice for two hours. The reaction mixture was evaporated to dryness under vacuum with slight heating (setting 1 on hot plate, approximately 40° C.) to form [$^3$H]1-(2-phosphonooxy-4,6-trihydroxy)-3-(4-azidophenyl)-propan-1-one. An aliquot of the dry reaction product was redissolved in water and checked by OD between 205 nm and 320 nm which showed a shoulder of a main peak at 245–255 nm.

The use of non-tritiated sodium borohydride gives 4-azido-2'-PP.

Example 10

Inhibition of Alkaline Phosphatase by 2'-PP

The rationale for examining the effect of 2'-PP on alkaline phosphatase activity was that only compounds with phosphoether bonds are substrates for intestinal brush border membrane alkaline phosphatase. Therefore, an extremely sensitive method of verifying the O-P linkage on 2'-PP was by examining the effect of 2'-PP concentration on alkaline phosphatase hydrolysis of its preferred substrate 4-nitrophenylphosphate. The results are shown in FIG. 5.

Figure 5:
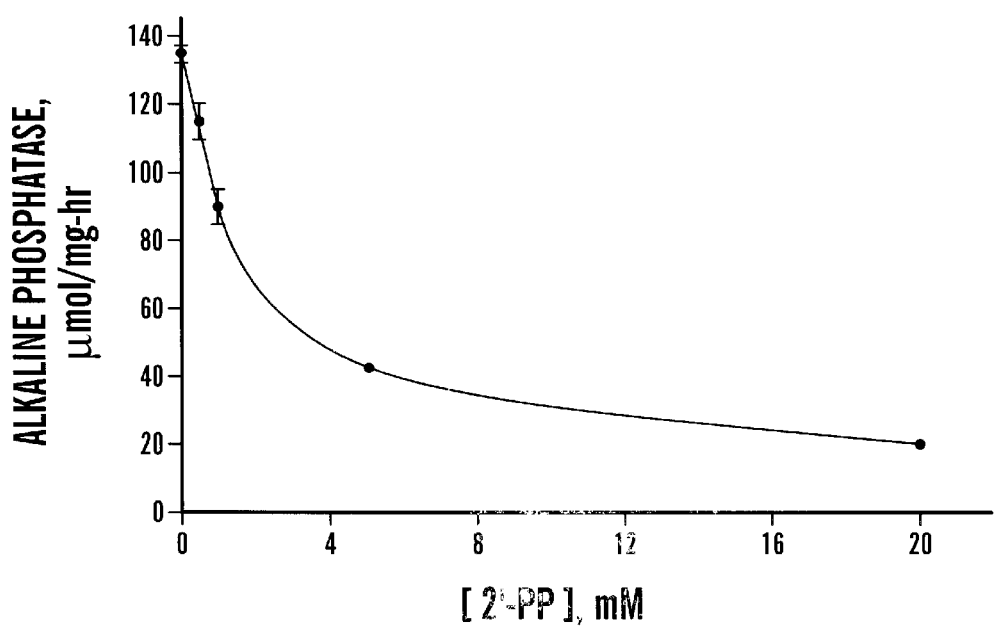
FIG. 5 shows the effect of 2'-PP on alkaline phosphatase activity.

FIG. 5 demonstrates that 2'-PP inhibited the alkaline phosphatase-mediated release of phosphate from 4-nitrophenylphosphate. Although the apparent $K_{0.5}$ (the concentration of 2'-PP resulting in 50% inhibition of alkaline phosphatase activity) was 3.2 mM±0.3 mM (n=3), or 6400 times the concentration of 2'-PP for 50% inhibition of he Na/phosphate co-transporter, the results are consistent with 2'-PP being a competitive inhibitor of alkaline phosphatase and having a phosphoether linkage. These studies were performed to verify that the phosphoether linkage was formed and viable in inhibiting co-transport.

Example 11

The Effect of 2'-PP on Na-dependent Phosphate Uptake using Rabbit Intestinal Brush Border Membrane (BBM) Vesicles Rabbit intestinal brush border membrane (BBM) vesicles were prepared by calcium precipitation as described in Peerce, B. E. and Clarke, R. D. (1990) *J. Biol. Chem.* 265: 1731–736; Peerce, B. E. and Wright, E. M. (1984) *J. Biol. Chem.* 259: 14105–112; and Stevens, B. R., Ross, H. J., and Wright, E. M. (1983) *J. Membr. Biol.* 66: 213–225. Na-dependent [$^{32}$P]phosphate uptake was measured by a rapid mixing rapid quenching vesicle filtration assay in media containing either 150 mM NaCl or 150 mM KCl as previously described in Peerce, B. E. (1988) *Progr. Clin. Biol. Res.* 252: 73–80 and Peerce, B. E. and Kiesling, C. (1990) *Miner. Electrol. Metab.* 16: 125–129. The effect of 2'-PP on the Na-dependent uptake of phosphate by BBM vesicles is shown in FIG. 6.

Figure 6:
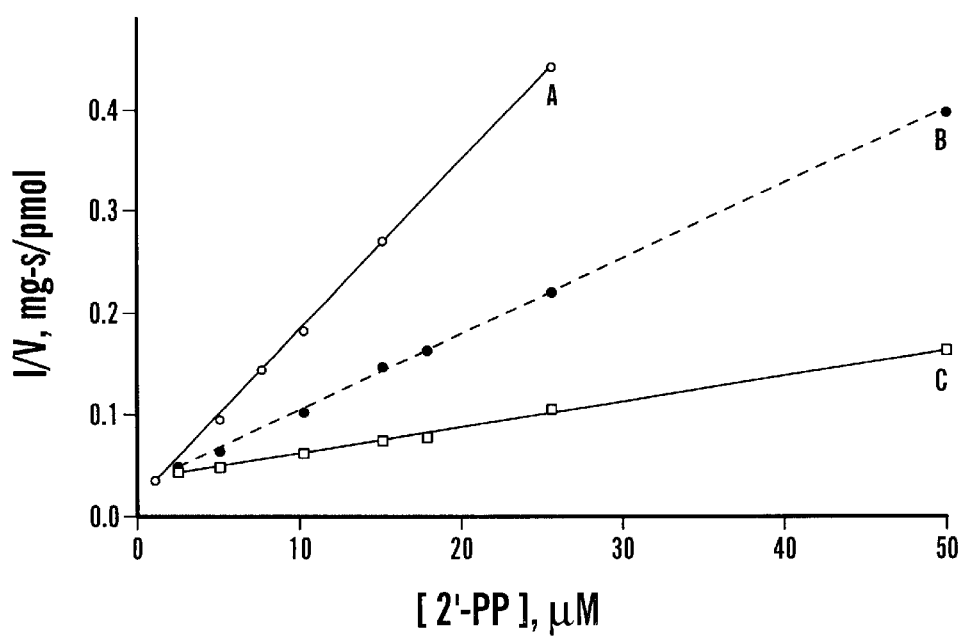
FIG. 6 is a Dixon plot showing the effect of 2'-PP on Na-dependent phosphate uptake by rabbit intestinal apical membrane vesicles at various phosphate concentrations.

Na-dependent phosphate uptake (defined as phosphate uptake in the presence of Na minus uptake in the presence of K) is shown in FIG. 6 as a function of 2'-PP concentration in the uptake media at 3 phosphate concentrations (A, [phosphate]=50 μM; B, [phosphate]=100 μM;, C [phosphate]=250 μM). The Dixon plot shown in FIG. 6 indicates that 2'-PP inhibition is competitive with respect to phosphate. The $K_1$ was determined from a replot of the slope of the Dixon plot as a function of the reciprocal of the phosphate concentration. The replot yields a slope of $K_m/V_{max}=K_I$. The $K_I$ for 2'-PP was 0.59±0.08 μM (n=3).

Figure 7:
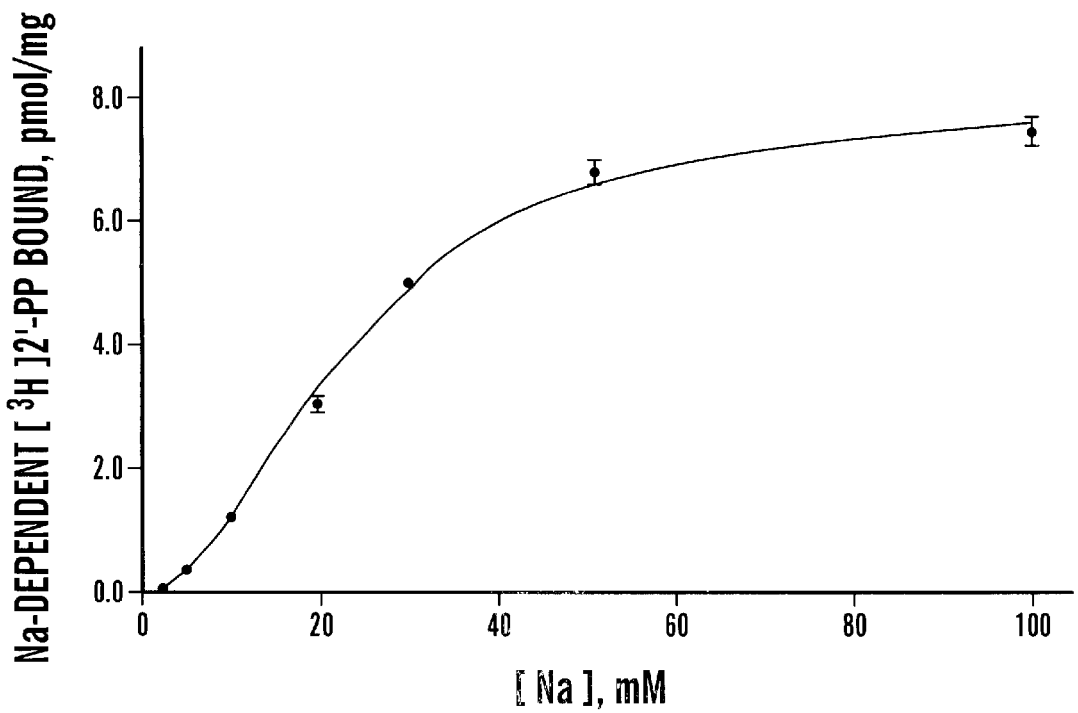
FIG. 7 shows the effect of Na concentration on 2'-PP binding to Ca-BBM protein.

[3H]2'-PP binding to a Ca-BBM protein as a function of Na concentration is shown in FIG. 7. In the absence of Na (Na replaced by K), 2'-PP binding was difficult to demonstrate (0.12±0.005 pmoles 2'-PP bound/mg protein. As a function of Na concentration, high affinity phosphate-sensitive 2'-PP binding was seen. Similar to the effect of Na concentration on Na-dependent phosphate uptake, the effect of Na on 2'-PP binding had an apparent $K_{0.5}$ for Na (Na concentration at 50% 2'-PP bound) of 23±3 mM (n=3). A Hill plot of the effect of Na concentration on 2'-PP binding suggested 2 Na bound/2'-PP ($n_H$=1.9±0.25, n=3).

Figure 8:
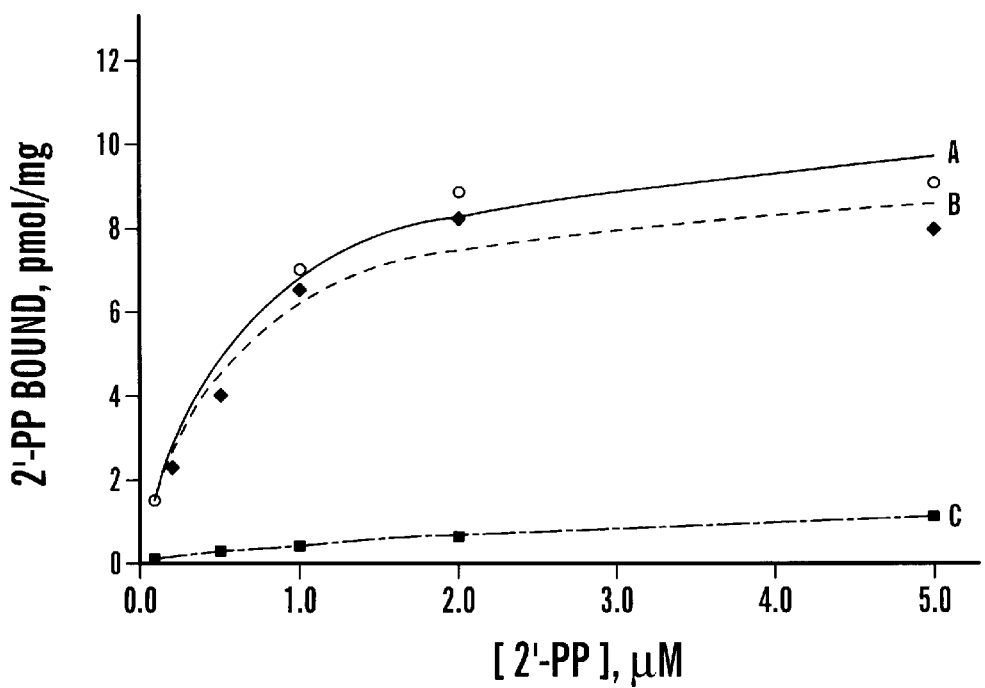
FIG. 8 shows the effect of phosphate on 2'-PP binding to Ca-BBM protein.

The effect of phosphate concentration on Na-dependent [$^3$H]2'-PP binding is shown in FIG. 8. 2'-PP bound in the absence (trace A), and presence (trace C) of 0.5 mM phosphate were examined. The difference between trace A and trace C yielded trace B. Kinetic analysis of trace B yielded a $K_d$ of 590 nM and 8.5 pmoles 2'-PP bound/mg protein. These results are similar to that seen for Na-dependent binding (FIG. 7), indicating that the high affinity binding of 2'-PP is Na-dependent and is at least 90% sensitive to phosphate. Phosphate and difluorophosphate inhibited 2'-PP binding to Ca-BBM protein with $K_{0.5}$'s similar to their $K_m$'s for Na-dependent transport. Phosphate inhibited 50% of the Na-dependent 2'-PP bound to Ca-BBM at 105±15 μM (n=3). Difluorophosphate inhibited 50% of the 2'-PP bound at 48±5 μM (n=3, results not shown). These results are in excellent agreement with previous reports for the apparent $K_m$ for phosphate as described in Peerce, B. E. (1988) *Progr. Clin. Biol. Res.* 252: 73–80; Peerce, B. E.; Cedilote, M.; Seifert, S.; Levine, R.; Kiesling, C. and Clark, R. D. (1993) *Am. J. Physiol.* 264: G609–G616 and Shirazy-Beechey, S.; Gorvel, J. -P. and Beechey, B. R. (1988) *J. Bioenerg. Biomembr.* 20: 273–288 and difluorophosphate as described in Peerce, B. E. (1997) *Biochim. Biophys. Acta.* 1323: 45–46 for Na-dependent phosphate uptake. These results are consistent with 2'-PP binding specifically to the intestinal BBM Na/phosphate co-transporter.

Figure 9:
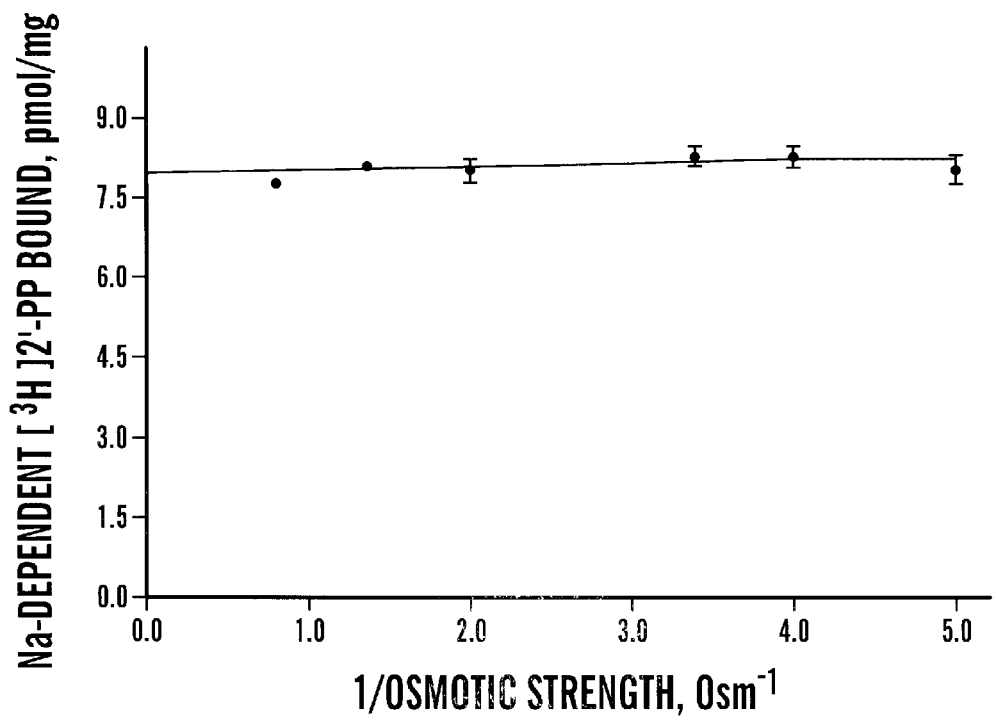
FIG. 9 shows the effect of osmotic strength on 2'-PP binding to Ca-BBM protein.

The possibility that the Na/phosphate co-transporter transported 2'-PP was examined by examining equilibrium Na-dependent [$^3$H]2'-PP bound as a function of external osmotic strength (varied with mannitol). The results are shown in FIG. 9. At infinite osmotic strength, 8±0.6 pmoles of 2'-PP bound/mg protein. External osmotic strength did not alter the amount of 2'-PP bound. These results are consistent with 2'-PP being poorly transported, or not transported by the intestinal Na/phosphate co-transporter.

The possibility that inhibition of Na-dependent phosphate uptake was at least partially due to degradation of 2'-PP with release of phosphate was examined by pre-incubation of 2'-PP with Ca-BBM for 10 minutes at 23° C. prior to examination of Na-dependent [$^{32}$P] phosphate uptake; the reason being that if BBM phosphatases (e.g., alkaline phosphatase) hydrolyzed 2'-PP, then a decrease in the apparent $k_{0.5}$ for inhibition of Na-dependent phosphate uptake would be seen since the apparent $K_{0.5}$ for phosphate is approximately 100 times that of 2'-PP. With incubations of up to 10 minutes at 23° C., there was no measurable change in the apparent $k_{0.5}$ for 2'-PP inhibition of Na-dependent [$^{32}$P] phosphate uptake. Although 2'-PP is a substrate of alkaline phosphatase (33%±5% inhibition at 50 μM 2'-PP), it is either poorly hydrolyzed or poorly released.

The preliminary results of examination of the interaction of 2'-PP with the intestinal Na/phosphate co-transporter indicate that 2'-PP is a high affinity inhibitor of the co-transporter, is competitive with respect to phosphate, and is not transported by the co-transporter at concentrations up to 50 μM. These results are consistent with 2'-PP being an excellent candidate as an inhibitor of intestinal absorption of phosphate.

Example 12

Effect of 2'-PP on Rat Survival and Serum Phosphate and Serum Calcium Levels

Ten rats with normal renal function were treated with varied amounts of [$^3$H]2'-PP by gavage for seven days. The 2'-PP was given once/day in a solution containing 270 mM sucrose and 10 mM Tris-Cl pH 7.4. Blood was withdrawn 1, 4, and 7 days from the start of the treatment and analyzed for serum phosphate and serum calcium, with the results shown in Table 1. A second, one-week trial was performed adding 2'-PP to the drinking water. Blood was withdrawn at 1, 4 and 7 days and assayed for calcium and phosphate. Dietary phosphorus was increased from 0.9% to 5% for one week, and the experiment repeated at the elevated dietary phosphorus with 2'-PP added to the drinking water for an additional two weeks. The amount of radioactivity in the urine and stool as examined. The results are shown in Table 1. After two weeks, the animals were sacrificed, and the kidney and liver were examined for radioactivity.

During the four weeks of treatment with 2'-PP, none of the rats died, nor did they suffer any measurable change in weight. Serum calcium levels (2.1 mM±0.18 mM) remained unchanged (7% fluctuation compared to 3% error in duplicate determinations) on both the normal and high phosphate diets irrespective of 2'-PP concentration. In contrast, serum phosphate was significantly reduced after seven days of treatment with 2'-PP. Serum phosphate was 2.5±0.2 mM prior to administration of 2'-PP (n=12). Table 1 shows that after seven days of treatment with 2'-PP, serum phosphate of rats on the normal (0.9% phosphorus) diet decreased in a 2'-PP concentration-dependent manner ranging from 2.2 mM at 2 μM 2'-PP to 1.4 mM at 25 μM 2'-PP. Rats on the high phosphate diet required higher 2'-PP concentrations to achieve the same results, however, similar decreases in serum phosphate were seen. Table 1 shows that rats on the 5% phosphorus diet had significantly reduced serum phosphate at 2 μM 2'-PP compared to untreated controls. At 10 μM 2'-PP, rats on the high phosphorus diet had serum phosphate levels below that seen in untreated rats on the normal phosphate diet.

Figure 10:
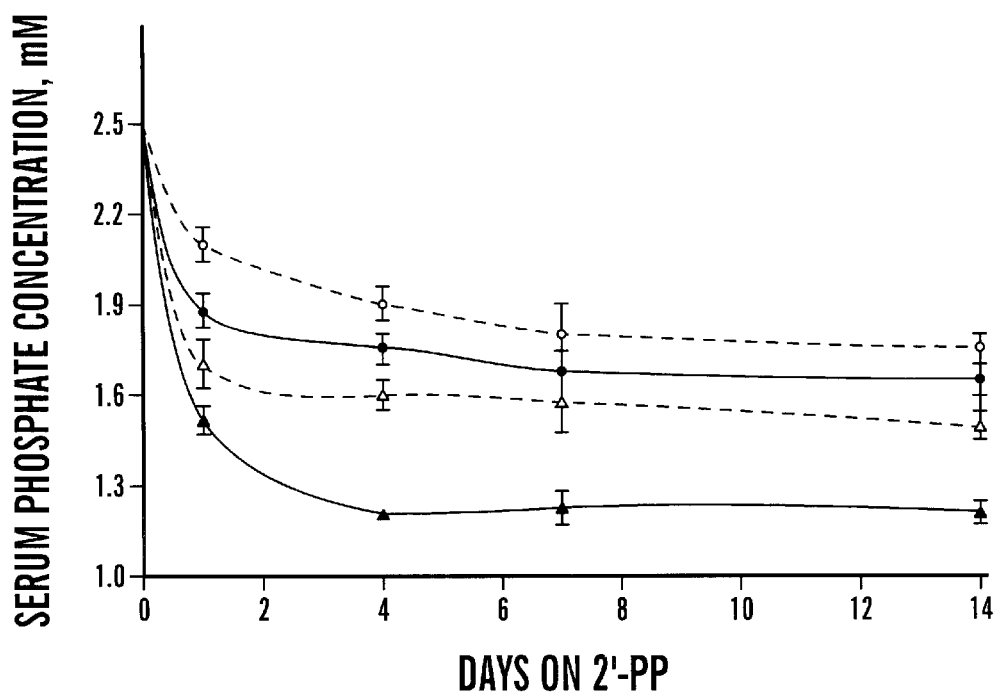
FIG. 10 shows the serum phosphate concentration in rats treated with various concentrations of 2'-PP.

FIG. 10 shows the results of a second 2-week study of ten rats with normal renal function (open circles, 1 μM 2'-PP; closed circles, 5 μM 2'-PP; open triangles, 10 μM 2'-PP; closed triangles, 25 μM 2'-PP). Serum phosphate again decreased in a 2'-PP concentration-dependent manner immediately after its addition to the rats' drinking water. After 2 weeks on 2'-PP, serum phosphate was reduced to between 1.8 mM on 1 μM 2'-PP and 1.2 mM at 25 μM 2'-PP. In contrast to the results shown in Table 1, there was a significant decrease in serum calcium (FIG. 11: open circles, 1 μM 2'-PP; closed circles, 5 μM 2'-PP; open triangles, 10 μM 2'-PP; closed triangles, 25 μM 2'-PP) at 2'-PP concentrations of 5 μM and higher. This decrease in serum calcium may be related to a slight volume expansion. The rats receiving 5 μM or higher concentrations of 2'-PP drank 2–4 times more water than normal for the first 4 days of the study. After the first 4 days, water consumption returned to normal.

After 4 weeks on 2'-PP, the rats were sacrificed and their kidneys and liver examined for radioactivity. No measurable radioactivity was found in the urine, kidney, or the liver. A crude estimate of 2'-PP turnover time was calculated from the amount of radioactivity in the stool after administration of [$^3$H]2'-PP was discontinued; and the 2'-PP half-life was estimated as 12±1 hr. The absence of measurable 2'-PP in the kidneys and urine suggests that 2'-PP is relatively impermeant across the intestinal membrane at the concentrations tested.

TABLE 1

Effect of 2'-PP on Serum Phosphate and Calcium

| | High Phosphate Diet | | Normal Phosphate Diet | |
| --- | --- | --- | --- | --- |
| [2'-PP] (μM) | Serum phosphate (mM) | Serum calcium (mM) | Serum phosphate (mM) | Serum calcium (mM) |
| 1 | 4.4 ± 0.2 | 2.1 ± 0.1 | 2.5 ± 0.1 | 2.1 ± 0.08 |
| 2 | 3.3 ± 0.2 | 2.1 ± 0.1 | 2.2 ± 0.1 | 2.1 ± 0.1 |
| 5 | 2.6 ± 0.1 | 2.1 ± 0.1 | 2.0 ± 0.07 | 2.1 ± 0.05 |
| 10 | 2.0 ± 0.04 | 2.1 ± 0.1 | 1.8 ± 0.1 | 2.0 ± 0.1 |
| 25 | 1.8 ± 0.08 | 2.0 ± 0.1 | 1.4 ± 0.1 | 2.1 ± 0.1 |

The values given are measured seven days after beginning treatment with the indicated 2'-PP concentration. Results are from duplicate rats and assayed in triplicate.

Example 13

In Vivo Half-life of 2'-PP in Rats

Figure 12:
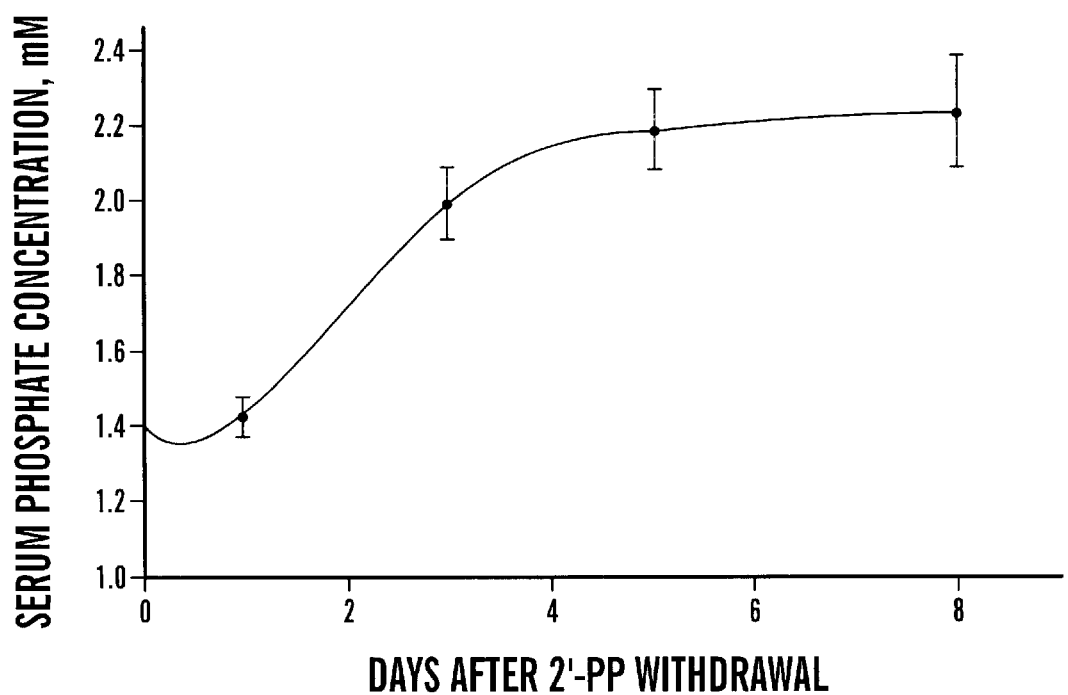
FIG. 12 shows the serum phosphate concentration in rats withdrawn from 2'-PP treatment.

Rats on a 0.9% phosphorus diet were given 10 μM [³H]2'-PP in their water for 2 weeks. Serum phosphate and calcium were determined by spectrophotometric assays. Following the experimental period, 2'-PP was removed from the water, and the stool was examined for radioactivity at days 1, 3, 5 and 8, and serum phosphate was examined. The serum phosphate levels are shown in FIG. 12.

Figure 11:
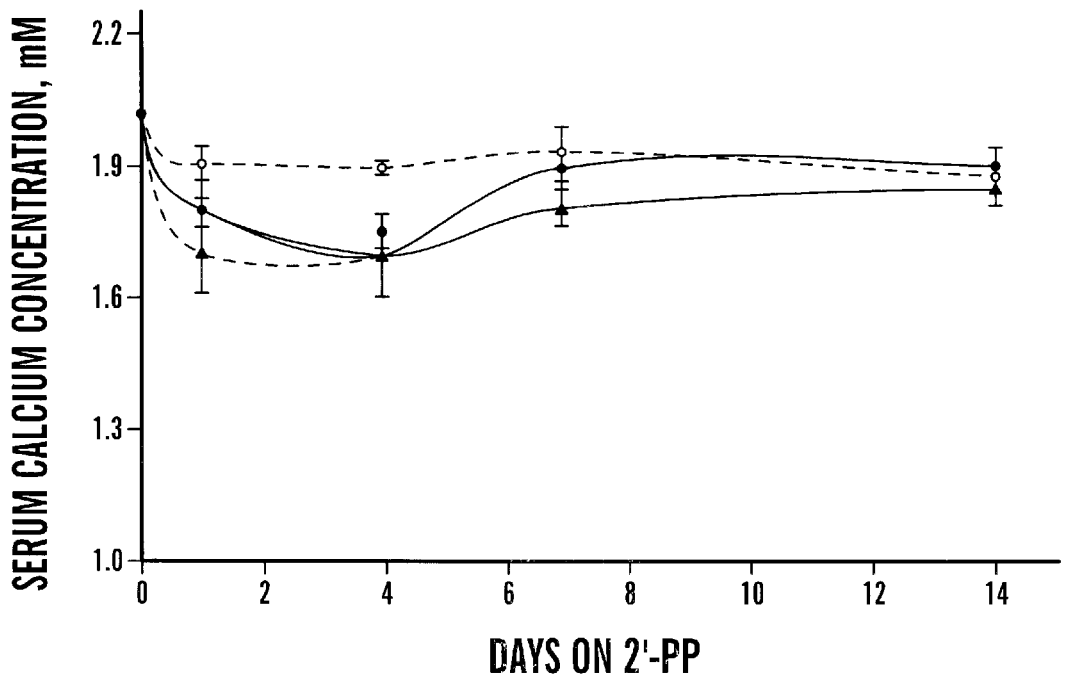
FIG. 11 shows the serum calcium concentration in rats treated with various concentrations of 2'-PP.

Following withdrawal of 2'-PP, serum phosphate returned to normal (control) level five days, as shown in FIG. 11. The apparent half-time to return to normal serum phosphate levels was approximately 3 days. This result is similar to the time required for intestinal crypt cell (salt-secreting cell) maturation into a villus tip cell (absorptive cell). During this maturation period, crypt cells express the intestinal brush border membrane Na/phosphate co-transporter. These results suggest that 10 μM 2'-PP administered daily yields effectively 100% inhibition of the Na/phosphate co-transporter. These results also suggest that recovery from 2'-PP inhibition of co-transporter activity requires adsorptive cell maturation.

Example 14

Specificity of AZPP for the Intestinal Na/phosphate Co-transporter

Ca-BBM protein (1.8 nmoles 2'-PP binding sites as determined from 9 pmoles [³H]2'-PP bound/mg protein) was labeled with [³H]AZPP (1 minute incubation with 10 μM [³H]AZPP at 4° C. in 150 mM NaCl and 10 mM sodium borate pH 7, followed by a 1 minute exposure to visible light). Following centrifugation to remove excess label, BBM protein was digested with papain as previously described in Peerce, B. E. (1995) *Biochim. Biophys. Acta.* 1239: 11–21 and Peerce, B. E.; Cedilote, M. and Clarke, R. D. (1995) *Biochim. Biophys. Acta.* 1239: 1–10, and resolved into membrane-retained and soluble peptides. 95% of the radioactivity was in the membrane-retained fraction. SDS-solubilization of the membrane-retained fraction released 85% of the radioactivity. Urea gel electrophoresis following papain digestion of SDS soluble protein revealed a single 24 kDa polypeptide labeled with [³H]AZPP.

A polyclonal antibody to the intestinal Na/phosphate co-transporter (KL9.2) developed in the laboratory was used to immunoprecipitate CHAPS-solubilized [³H]AZPP-labeled Ca-BBM protein. The complex was electrophoresed by SDS-PAGE and stained with Coomassie blue, according to the method of Laemmli, U.K 1970 *Nature (Lond.)* 227: 680–685. A track was cut into 2 mm slices, and the slices counted for tritium. A single 120-kDa polypeptide was seen labeled with [³H]AZPP. These results are consistent with 2'-PP specifically labeling the intestinal Na/phosphate co-transporter. The residual 12%±2%, n=3, of the applied label appeared to be non-specifically associated with lipid (chloroform:methanol extracted). The specificity of [¹H] AZPP labeling of the 120-kDa polypeptide in Ca-BBM protein suggests that the 24-kDa polypeptide purified from the papain digest is also derived from the Na/phosphate co-transporter.

Example 15

Effect of NHPP on Na-dependent Uptake of [³²P] Phosphate by BBM Vesicles

Figure 13:
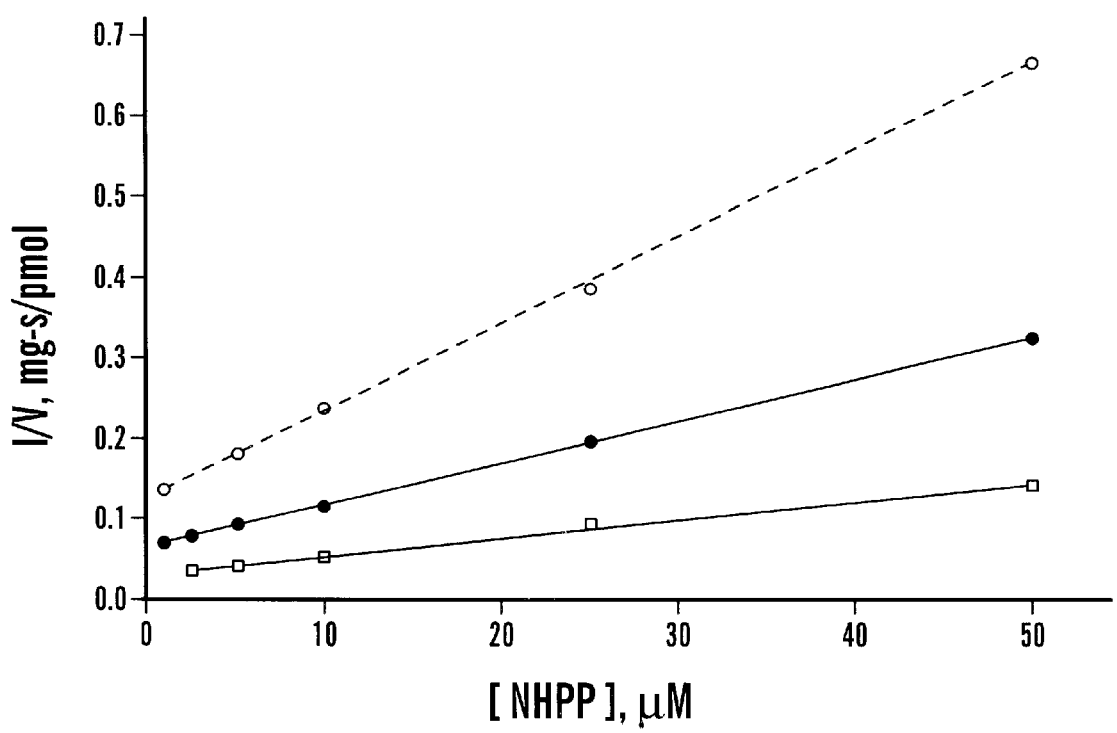
FIG. 13 is a Dixon plot of the effect of 2'-aminophosphophloretin (NHPP) on Na-dependent [$^{32}$P] phosphate uptake by BBM vesicles.

NHPP was administered to BBM in conformity with the 2'-PP protocol described above and the results are shown in FIG. 13. FIG. 13 shows that NHPP is a competitive inhibitor of Na-dependent phosphate uptake by intestinal BBM vesicles with respect to phosphate. The Dixon plot shown in FIG. 13 illustrates that increasing phosphate concentrations reduce the Na-dependent phosphate uptake. A replot of the Dixon plot, plotting the slope of the Dixon plot versus the reciprocal of the phosphate concentration is a straight line going through the origin, with a slope of $K_m/V_{max}=K_1$. The $K_1$ for NHPP was 6.9±1 μM (n=3). These results indicate that although NHPP is not a substrate of apical membrane phosphatase, NHPP does inhibit the co-transporter. The amino-phosphate linkage limits the effectiveness of NHPP inhibition of Na-dependent phosphate uptake by the intestinal Na/phosphate co-transporter. The lower efficacy of NHPP relative to 2'-PP provides greater flexibility in dosage control for patients with only marginally high phosphate blood levels. This same type of reduction in effectiveness is anticipated for thio analogs as well. However, like all other classes of drugs, there may be aminophosphate and thio-phosphate agents that are more effective than their phosphate parent compounds.

While this invention has been described in conjunction with specific embodiments and examples, it will be evident to one of ordinary skill in the art, having regard to this disclosure, that equivalents of the specifically disclosed materials and techniques will also be applicable to this invention; and such equivalents are intended to be included within the following claims.

What is claimed is:

1. A compound of formula (I):

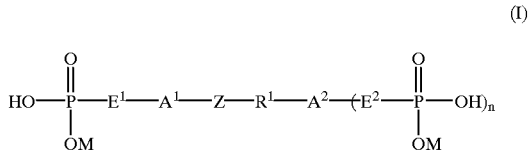

where:
- $A^1$ and $A^2$ are the same or different aryl groups collectively bearing at least one hydrophilic substituent;
- $E^1$ and $E^2$ are the same or different and are O, S, or $NR^2$ (where $R^2$ is H or a linear or branched $C_1$–$C_{20}$ carbon containing group);
- M is H or a pharmaceutically acceptable monovalent cation;
- $R^1$ is a linear or branched, saturated or unsaturated, $C_1$–$C_{20}$ carbon containing group;
- Z is a single bond, a carbonyl, $CE^3E^4$, or $CR^3E^{41}$, where $E^3$ and $E^4$ are the same or different and are $OR^4$, $SR^{41}$, and $NR^4{}_2$, where
  - $R^3$ is a linear or branched $C_1$–$C_{20}$ carbon containing group, and
  - $R^4$ is H or a linear or branched $C_1$–$C_{20}$ carbon containing group; and
- n is 0 or 1, or a pharmaceutically acceptable salt thereof, provided that, when $E^1$ is O and when Z is a carbonyl and when $A^1$ is a phenyl ring and when $E^1$ is at the 2-position of the phenyl ring $A^1$, $A^1$ is not further substituted in the 4- and 6-positions of the phenyl ring $A^1$ with $OR_5$ groups (where $R^5$ is a carbon containing group having between 1 and 4 carbon atoms); and further provided that the compound is not 4'-phosphophloretin or a pharmaceutically acceptable salt thereof.

2. The compound of claim 1 that is a compound of formula (Ia):

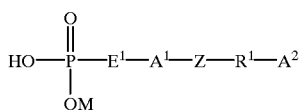

(Ia)

where:
$A^1$, $A^2$, $E^1$, M, $R^1$ and Z are as defined in claim 1, or a pharmaceutically acceptable salt thereof, provided that the compound is not 4'-phosphophloretin or a pharmaceutically acceptable salt thereof.

3. The compound of claim 1 that is a compound of formula (Ib):

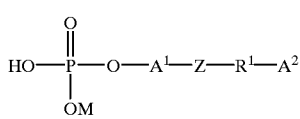

(Ib)

where:
$A^1$, $A^2$, M, $R^1$ and Z are as defined in claim 1, or a pharmaceutically acceptable salt thereof, provided that the compound is not 4'-phosphophloretin or a pharmaceutically acceptable salt thereof.

4. The compound of claim 1 that is a compound of formula (Ic):

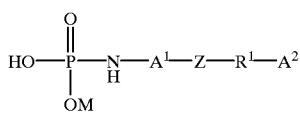

(Ic)

where:
$A^1$, $A^2$, M, $R^1$ and Z are as defined in claim 1, or a pharmaceutically acceptable salt thereof.

5. The compound of claim 1 that is a compound of formula (Id):

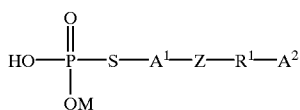

(Id)

where:
$A^1$, $A^2$, M, $R^1$ and Z are as defined in claim 1, or a pharmaceutically acceptable salt thereof.

6. The compound of claim 1 that is a compound of formula (Ie):

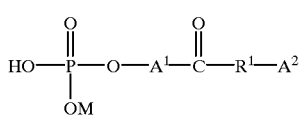

(Ie)

where:
$A^1$, $A^2$, M, and $R^1$ are as defined in claim 1, or a pharmaceutically acceptable salt thereof, provided that the compound is not 4'-phosphophloretin or a pharmaceutically acceptable salt thereof.

7. The compound of claim 1 that is a compound of formula (If):

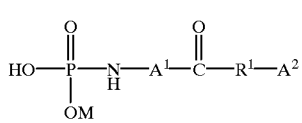

(If)

where:
$A^1$, $A^2$, M, and $R^1$ are as defined in claim 1, or a pharmaceutically acceptable salt thereof.

8. The compound of claim 1 that is a compound of formula (Ig):

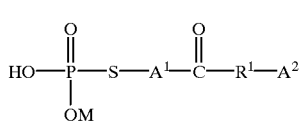

(Ig)

where:
$A^1$, $A^2$, M, and $R^1$ are as defined in claim 1, or a pharmaceutically acceptable salt thereof.

9. The compound of claim 1 that is 2'-phosphophloretin, 2'-thiophosphophloretin, 2'-aminophosphophloretin, 3-azido-2'-phosphophloretin, or 4-azido-2'-phosphophloretin or a pharmaceutically acceptable salt thereof.

10. A medication comprising a carrier and a therapeutically effective amount of a compound of formula (I):

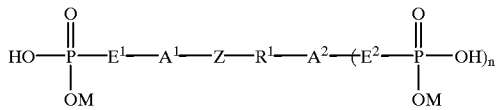

(I)

where:
$A^1$ and $A^2$ are the same or different aryl groups collectively bearing at least one hydrophilic substituent;
$E^1$ and $E^2$ are the same or different and are O, S, or $NR^2$ (where $R^2$ is H or a linear or branched $C_1$–$C_{20}$ carbon containing group);
M is H or a pharmaceutically acceptable monovalent cation;
$R^1$ is a linear or branched, saturated or unsaturated, $C_1$–$C_{20}$ carbon containing group;
Z is a single bond, a carbonyl, $CE^3E^4$, or $CR^3E^4$, where $E^3$ and $E^4$ are the same or different and are $OR^4$, $SR^4$, and $NR^4_2$, where
$R^3$ is a linear or branched $C_1$–$C_{20}$ carbon containing group, and
$R^4$ is H or a linear or branched $C_1$–$C_{20}$ carbon containing group; and
n is 0 or 1, or a pharmaceutically acceptable salt thereof, provided that, when $E^1$ is O and when Z is a carbonyl and when $A^1$ is a phenyl ring and when $E^1$ is at the 2-position of the phenyl ring $A^1$, $A^1$ is not further substituted in the 4- and 6-positions of the phenyl ring $A^1$ with $OR^5$ groups (where $R^5$ is a carbon containing group having between 1 and 4 carbon atoms).

11. The medication of claim 10 where the compound is a compound of formula (Ia):

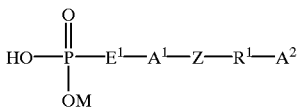
(Ia)

where:
$A^1$, $A^2$, $E^1$, M, $R^1$ and Z are as defined in claim 10, or a pharmaceutically acceptable salt thereof.

12. The medication of claim 10 where the compound is a compound of formula (Ib):

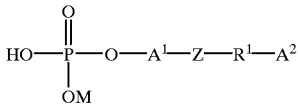
(Ib)

where:
$A^1$, $A^2$, M, $R^1$ and Z are as defined in claim 10, or a pharmaceutically acceptable salt thereof.

13. The medication of claim 10 where the compound is a compound of formula (Ic):

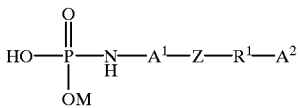
(Ic)

where:
$A^1$, $A^2$, M, $R^1$ and Z are as defined in claim 10, or a pharmaceutically acceptable salt thereof.

14. The medication of claim 10 where the compound is a compound of formula (Id):

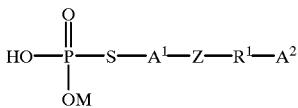
(Id)

where:
$A^1$, $A^2$, M, $R^1$ and Z are as defined in claim 10, or a pharmaceutically acceptable salt thereof.

15. The medication of claim 10 where the compound is a compound of formula (Ie):

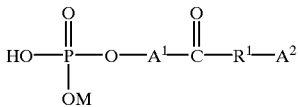
(Ie)

where:
$A^1$, $A^2$, M, and $R^1$ are as defined in claim 10, or a pharmaceutically acceptable salt thereof.

16. The medication of claim 10, where the compound is a compound of formula (If):

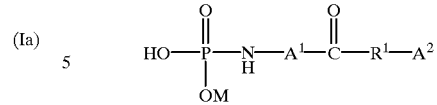
(If)

where:
$A^1$, $A^2$, M, and $R^1$ are as defined in claim 10, or a pharmaceutically acceptable salt thereof.

17. The medication of claim 10, where the compound is a compound of formula (Ig):

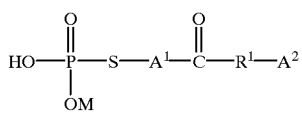
(Ig)

where:
$A^1$, $A^2$, M, and $R^1$ are as defined in claim 10, or a pharmaceutically acceptable salt thereof.

18. The medication of claim 10 where the compound is 2'-phosphophloretin, 2'-thiophosphophloretin, 2'-aminophosphophloretin, 3-azido-2'-phosphophloretin, or 4-azido-2'-phosphophloretin or a pharmaceutically acceptable salt thereof.

19. A method of inhibiting sodium-mediated phosphate uptake, reducing serum PTH, calcium, calcitriol, or phosphate, or treating renal disease, said method comprising administration of a compound of formula (I):

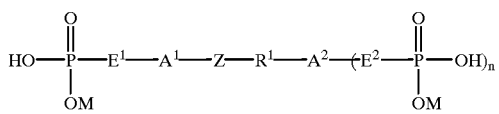
(I)

where:
$A^1$ and $A^2$ are the same or different aryl groups collectively bearing at least one hydrophilic substituent;

$E^1$ and $E^2$ are the same or different and are O, S, or $NR^2$ (where $R^2$ is H or a linear or branched $C_1$–$C_{20}$ carbon containing group);

M is H or a pharmaceutically acceptable monovalent cation;

$R^1$ is a linear or branched, saturated or unsaturated, $C_1$–$C_{20}$ carbon containing group;

Z is a single bond, a carbonyl, $CE^3E^4$, or $CR^3E^4$, where $E^3$ and $E^4$ are the same or different and are $OR^4$, $SR^4$, and $NR^4_2$, where
$R^3$ is a linear or branched $C_1$–$C_{20}$ carbon containing group, and
$R^4$ is H or a linear or branched $C_1$–$C_{20}$ carbon containing group; and n is 0 or 1, or a pharmaceutically acceptable salt thereof.

20. The method of claim 19 where the compound is a compound of formula (Ia):

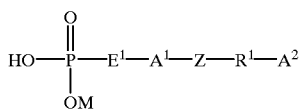

(Ia)

where:

A¹, A², E¹, M, R¹ and Z are as defined in claim 19, or a pharmaceutically acceptable salt thereof.

21. The method of claim 19 where the compound is a compound of formula (Ib):

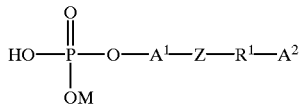

(Ib)

where:

A¹, A², M, R¹ and Z are as defined in claim 19, or a pharmaceutically acceptable salt thereof.

22. The method of claim 19 where the compound is a compound of formula (Ic):

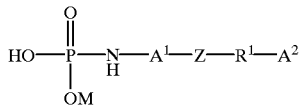

(Ic)

where:

A¹, A², M, R¹ and Z are as defined in claim 19, or a pharmaceutically acceptable salt thereof.

23. The method of claim 19 where the compound is a compound of formula (Id):

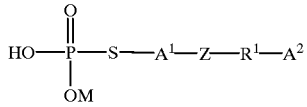

(Id)

where:

A¹, A², M, R¹ and Z are as defined in claim 19, or a pharmaceutically acceptable salt thereof.

24. The method of claim 19 where the compound is a compound of formula (Ie):

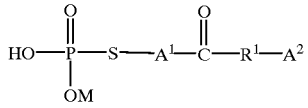

(Ie)

where:

A¹, A², M, and R¹ are as defined in claim 19, or a pharmaceutically acceptable salt thereof.

25. The method of claim 19 where the compound is a compound of formula (If):

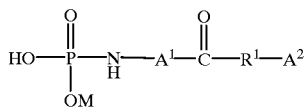

(If)

where:

A¹, A², M, and R¹ are as defined in claim 19, or a pharmaceutically acceptable salt thereof.

26. The method of claim 19 where the compound is a compound of formula (Ig):

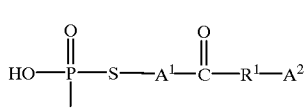

(Ig)

where:

A¹, A², M, and R¹ are as defined in claim 19, or a pharmaceutically acceptable salt thereof.

27. The method of claim 19 where the compound is 2'-phosphophloretin, 2'-thiophosphophloretin, 2'-aminophosphophloretin, 3-azido-2'-phosphophloretin, or 4-azido-2'-phosphophloretin or a pharmaceutically acceptable salt thereof.

28. The method of claim 19 where the administration is intermittent.

29. The method of claim 19 where the administration is oral.

30. The method of claim 19 where the administration is parenteral.

31. A process for preparing a compound of Formula I:

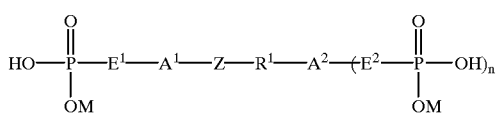

(I)

where:

A¹ and A² are the same or different aryl groups collectively bearing at least one hydrophilic substituent;

E¹ and E² are the same or different and are O, S, or NR² (where R² is H or a linear or branched $C_1$–$C_{20}$ carbon containing group);

M is H or a pharmaceutically acceptable monovalent cation;

R¹ is a linear or branched, saturated or unsaturated, $C_1$–$C_{20}$ carbon containing group;

Z is a single bond, a carbonyl, $CE^3E^4$, or $CR^3E^4$, where $E^3$ and $E^4$ are the same or different and are $OR^4$, $SR^4$, and $NR^4_2$, where R³ is a linear or branched $C_1$–$C_{20}$ carbon containing group, and R⁴ is H or a linear or branched $C_1$–$C_{20}$ carbon containing group; and n is 0 or 1, or a pharmaceutically acceptable salt thereof, provided that the compound is not 4'-phosphophloretin or a pharmaceutically acceptable salt thereof, said process comprising:

(a) phosphorylating a compound of the formula $E^1$—$A^1$—Z-$R^1$—$A^2$—$(E)_n$ and which either contains or does not contain one or more protecting groups to yield any one of the compounds (I) through (Ig); or (b) if $R^1$ is an unsaturated group, hydrogenating it; or (c) cleaving any protecting groups in a compound of Formula I to liberate free hydroxyl or phosphate groups; or (d) converting a compound of Formula I to a pharmaceutically acceptable salt; or (e) converting a salt of a compound of Formula I to a compound of Formula I; or (f) converting a salt of a compound of Formula I to a pharmaceutically acceptable salt of a compound of Formula I; or (g) converting a substituent in $A^1$ or $A^2$ to another substituent.

32. The compound of claim 1, wherein $E^1$ is O and wherein $A^2$ is a phenyl ring bearing an OH group in the 4-position thereof.

33. The compound of claim 1, wherein $E^1$ is O; wherein $A^1$ is a phenyl ring; wherein $E^1$ is at the 2-position of the phenyl ring $A^1$; and wherein the phenyl ring $A^1$ is further substituted with an OH group in the 4-position thereof.

34. The compound of claim 1, wherein $E^1$ is O and wherein $A^1$ is a phenyl ring; wherein $E^1$ is at the 2-position of the phenyl ring $A^1$; and wherein the phenyl ring $A^1$ is further substituted with an OH group in the 6-position thereof.

35. The compound of claim 1, wherein $E^1$ is O and wherein $A^1$ is a phenyl ring; wherein $E^1$ is at the 2-position of the phenyl ring $A^1$; and wherein the phenyl ring $A^1$ is further substituted with OH groups in the 4- and 6-positions thereof.

36. The compound of claim 1, wherein $E^1$ is O; wherein $A^2$ is a phenyl ring bearing an OH group in the 4-position thereof; wherein $A^1$ is a phenyl ring; wherein $E^1$ is at the 2-position of the phenyl ring $A^1$; and wherein the phenyl ring $A^1$ is further substituted with OH groups in the 4- and 6-positions thereof.

37. The compound of claim 1, wherein $A^1$ is a phenyl ring and $E^1$ is at the 2-position of the phenyl ring $A^1$.

38. The medication of claim 10, wherein the compound is not 4'-phosphophloretin or a pharmaceutically acceptable salt thereof.

39. The medication of claim 10, wherein $E^1$ is O and wherein $A^2$ is a phenyl ring bearing an OH group in the 4-position thereof.

40. The medication of claim 10, wherein $E^1$ is O; wherein $A^1$ is a phenyl ring; wherein $E^1$ is at the 2-position of the phenyl ring $A^1$; and wherein the phenyl ring $A^1$ is further substituted with an OH group in the 4-position thereof.

41. The medication of claim 10, wherein $E^1$ is O and wherein $A^1$ is a phenyl ring; wherein $E^1$ is at the 2-position of the phenyl ring $A^1$; and wherein the phenyl ring $A^1$ is further substituted with an OH group in the 6-position thereof.

42. The medication of claim 10, wherein $E^1$ is O and wherein $A^1$ is a phenyl ring; wherein $E^1$ is at the 2-position of the phenyl ring $A^1$; and wherein the phenyl ring $A^1$ is further substituted with OH groups in the 4- and 6-positions thereof.

43. The medication of claim 10, wherein $E^1$ is O; wherein $A^2$ is a phenyl ring bearing an OH group in the 4-position thereof; wherein $A^1$ is a phenyl ring; wherein $E^1$ is at the 2-position of the phenyl ring $A^1$; and wherein the phenyl ring $A^1$ is further substituted with OH groups in the 4- and 6-positions thereof.

44. The medication of claim 10, wherein $A^1$ is a phenyl ring and $E^1$ is at the 2-position of the phenyl ring $A^1$.

45. The method of claim 19, wherein the compound is not 4'-phosphophloretin or a pharmaceutically acceptable salt thereof.

46. The method of claim 19, wherein, when $E^1$ is O and when Z is a carbonyl and when $A^1$ is a phenyl ring and when $E^1$ is at the 2-position of the phenyl ring $A^1$ and when the phenyl ring $A^1$ is further substituted in the 4- and 6-positions thereof with $OR^5$ groups (where $R^5$ is a carbon containing group having between 1 and 4 carbon atoms), $A^2$ is not a phenyl ring substituted in the 4-position thereof with an $OR^{5'}$ group (where $R^{5'}$ is a carbon containing group having between 1 and 4 carbon atoms).

47. The method of claim 46, wherein, when $E^1$ is O and when Z is a carbonyl and when $A^1$ is a phenyl ring and when $E^1$ is at the 2-position of the phenyl ring $A^1$, $A^1$ is not further substituted in the 4- and 6-positions of the phenyl ring $A^1$ with $OR^5$ groups (where $R^5$ is a carbon containing group having between 1 and 4 carbon atoms).

48. The method of claim 19, wherein $E^1$ is O and wherein $A^2$ is a phenyl ring bearing an OH group in the 4-position thereof.

49. The method of claim 19, wherein $E^1$ is O; wherein $A^1$ is a phenyl ring; wherein $E^1$ is at the 2-position of the phenyl ring $A^1$; and wherein the phenyl ring $A^1$ is further substituted with an OH group in the 4-position thereof.

50. The method of claim 19, wherein $E^1$ is O and wherein $A^1$ is a phenyl ring; wherein $E^1$ is at the 2-position of the phenyl ring $A^1$; and wherein the phenyl ring $A^1$ is further substituted with an OH group in the 6-position thereof.

51. The method of claim 19, wherein $E^1$ is O and wherein $A^1$ is a phenyl ring; wherein $E^1$ is at the 2-position of the phenyl ring $A^1$; and wherein the phenyl ring $A^1$ is further substituted with OH groups in the 4- and 6-positions thereof.

52. The method of claim 19, wherein $E^1$ is O; wherein $A^2$ is a phenyl ring bearing an OH group in the 4-position thereof; wherein $A^1$ is a phenyl ring; wherein $E^1$ is at the 2-position of the phenyl ring $A^1$; and wherein the phenyl ring $A^1$ is further substituted with OH groups in the 4- and 6-positions thereof.

53. The method of claim 19, wherein $A^1$ is a phenyl ring and $E^1$ is at the 2-position of the phenyl ring $A^1$.

54. The process of claim 31, wherein, when $E^1$ is O and when Z is a carbonyl and when $A^1$ is a phenyl ring and when $E^1$ is at the 2-position of the phenyl ring $A^1$ and when the phenyl ring $A^1$ is further substituted in the 4- and 6-positions thereof with $OR^5$ groups (where $R^5$ is a carbon containing group having between 1 and 4 carbon atoms), $A^2$ is not a phenyl ring substituted in the 4-position thereof with an $OR^{5'}$ group (where $R^{5'}$ is a carbon containing group having between 1 and 4 carbon atoms).

55. The process of claim 54, wherein, when $E^1$ is O and when Z is a carbonyl and when $A^1$ is a phenyl ring and when $E^1$ is at the 2-position of the phenyl ring $A^1$, $A^1$ is not further substituted in the 4- and 6-positions of the phenyl ring $A^1$ with $OR^5$ groups (where $R^5$ is a carbon containing group having between 1 and 4 carbon atoms).

56. The process of claim 31, wherein $A^1$ is a phenyl ring and $E^1$ is at the 2-position of the phenyl ring $A^1$.

57. The process of claim 31, wherein the compound of Formula I is 2'-phosphophloretin, 2'-thiophosphophloretin, 2'-aminophosphophloretin, 3-azido-2'-phosphophloretin, or 4-azido-2'-phosphophloretin or a pharmaceutically acceptable salt thereof.

* * * * *

UNITED STATES PATENT AND TRADEMARK OFFICE
CERTIFICATE OF CORRECTION

PATENT NO.    : 6,355,823 B1
DATED         : March 12, 2002
INVENTOR(S)   : Peerce It is certified that error appears in the above-identified patent and that said Letters Patent is hereby corrected as shown below:

Column 5,
Lines 48-61, delete the paragraph and replace the deleted paragraph with the following replacement paragraph:
-- Particularly preferred examples of compounds of formulas (I) and (Ia) through (Ig) include, without limitation, 2'-phosphophloretin (2'-PP), 3-azido-2'-phosphophloretin (AZPP), 4-azido-2'-phosphophloretin, 2'-thiophosphophloretin, 2'-aminophosphophloretin (NHPP), and the pharmaceutically acceptable salts thereof, especially the potassium salts. --

Signed and Sealed this

Twenty-fourth Day of September, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.    : 6,355,823 B1
DATED         : March 12, 2002
INVENTOR(S)   : Peerce It is certified that error appears in the above-identified patent and that said Letters Patent is hereby corrected as shown below:

Column 5,
Lines 48-61, delete the paragraph and replace the deleted paragraph with the following replacement paragraph:
-- Particularly preferred examples of compounds of formulas (I) and (Ia) through (Ig) include, without limitation, 2'-phosphophloretin (2'-PP), 3-azido-2'-phosphophloretin (AZPP), 4-azido-2'-phosphophloretin, 2'-thiophosphophloretin, 2'-aminophosphophloretin (NHPP), and the pharmaceutically acceptable salts thereof, especially the potassium salts. --

Signed and Sealed this

Fifteenth Day of October, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,355,823 B1
DATED         : March 12, 2002
INVENTOR(S)   : Peerce It is certified that error appears in the above-identified patent and that said Letters Patent is hereby corrected as shown below:

Column 3,
Line 51, replace "—$SR^1$" with -- —$SR^8$ --.
Line 53, immediately before "—$NR^9R^{10}$", delete the apostrophe.
Line 53, replace "$R^0$" with -- $R^{10}$ --.

Column 6,
Lines 9-10, replace "1-(2-phosphonothio-5-dihydroxyphenyl)-2-(3-hydroxphenyl)ethane," with -- 1-(2-phosphonothio-5-hydroxyphenyl)-2-(3-hydroxyphenyl)ethane, --.
Lines 29-30, replace "1-(2-phosphonothio-4-dihydroxyphenyl)-2-(4-hydroxphenyl)ethane," with -- 1-(2-phosphonothio-4-hydroxyphenyl)-2-(4-hydroxyphenyl)ethane, --.
Lines 35-36, replace "1-(2-phosphonothio-5-dihydroxyphenyl)-2-(4-hydroxphenyl)ethane," with -- 1-(2-phosphonothio-5-hydroxyphenyl)-2-(4-hydroxyphenyl)ethane, --.

Column 7,
Lines 14-15, replace "1-(2-phosphonothio-4-dihydroxyphenyl)-2-(4-hydroxyphenyl)-1-hydroxyethane," with -- 1-(2-phosphonothio-4-hydroxyphenyl)-2-(4-hydroxyphenyl)-1-hydroxyethane, --.
Lines 66-67, replace 1-(2-phosphonothio-4-dihydroxyphenyl)-2-(4-hydroxyphenyl)-1,1-dihydroxyethane," with -- 1-(2-phosphonothio-4-hydroxyphenyl)"-2-(4-hydroxyphenyl)-1,1dihydroxyethane, --.

Column 8,
Lines 5-6, replace "1-(2-phosphonothio-5-dihydroxyphenyl)-2-(4-hydroxyphenyl)-1,1-dihydroxyethane," with -- 1-(2-phosphonothio-5-hydroxyphenyl)-2-(4-hydroxyphenyl)-1,1dihydroxyethane, --.
Lines 50-51, replace "1-(2-phosphonothio-4-dihydroxyphenyl)-2-(4-hydroxyphenyl)ethane-l-one," with -- 1-(2-phosphonothio-4-hydroxyphenyl)-2-(4-hydroxyphenyl)ethane-l-one,--.

Column 10,
Lines 1-2, replace "1-(2-phosphonothio-5-dihydroxyphenyl)-2-(3-hydroxyphenyl)propane," with -- 1-(2-phosphonothio-5-hydroxyphenyl)-2-(3-hydroxyphenyl)propane, --.
Lines 20-21, replace "1-(2-phosphonothio-4-dihydroxyphenyl)-2-(4-hydroxyphenyl)propane," with -- 1-(2-phosphonothio-4-hydroxyphenyl)-2-(4-hydroxyphenyl)propane, --.
Lines 27-28, replace "1-(2-phosphonothio-5-dihydroxyphenyl)-2-(4-hydroxyphenyl)propane," with -- 1-(2-phosphonothio-5-hydroxyphenyl)-2-(4-hydroxyphenyl)propane, --.

UNITED STATES PATENT AND TRADEMARK OFFICE
CERTIFICATE OF CORRECTION

PATENT NO.   : 6,355,823 B1
DATED        : March 12, 2002
INVENTOR(S)  : Peerce

It is certified that error appears in the above-identified patent and that said Letters Patent is hereby corrected as shown below:

Column 11,
Lines 5-6, replace "1-(2-phosphonothio-4-dihydroxyphenyl)-2-(4-hydroxyphenyl)-1-hydroxypropane," with -- 1-(2-phosphonothio-4-hydroxyphenyl)-2-(4-hydroxyphenyl)-1-hydroxypropane, --.
Lines 57-58, replace "1-(2-phosphonothio-4-dihydroxyphenyl)-2-(4-hydroxyphenyl)-1,1-dihydroxypropane," with -- 1-(2-phosphonothio-4-hydroxyphenyl)-2-(4-hydroxyphenyl)-1,1dihydroxypropane, --.
Lines 64-65, replace "1-(2-phosphonothio-5-dihydroxyphenyl)-2-(4-hydroxyphenyl)-1,1-dihydroxypropane," with -- 1-(2-phosphonothio-5-hydroxyphenyl)-2-(4-hydroxyphenyl)-1,1dihydroxypropane, --.

Column 12,
Lines 42-43, replace "1-(2-phosphonothio-4-dihydroxyphenyl)-2-(4-hydroxyphenyl) propan-l-one," with -- 1-(2-phosphonothio-4-hydroxyphenyl)-2-(4-hydroxyphenyl) propan-l-one, --.

Column 13,
Lines 7-8, replace "1-(2-phosphonothio-5-dihydroxyphenyl)-3-(3-hydroxyphenyl)propane," with -- 1-(2-phosphonothio-5-hydroxyphenyl)-3-(3-hydroxyphenyl)propane, --.
Lines 27-28, replace "1-(2-phosphonothio-4-dihydroxyphenyl)-3-(4-hydroxyphenyl) propane," with -- 1-(2-phosphonothio-4-hydroxyphenyl)-3-(4-hydroxyphenyl)propane, --.
Lines 33-34, replace "1-(2-phosphonothio-5-dihydroxyphenyl)-3-(4-hydroxyphenyl) propane," with -- 1-(2-phosphonothio-5-hydroxyphenyl)-3-(4-hydroxyphenyl)propane, --.

Column 14,
Lines 11-12, replace "1-(2-phosphonothio-4-dibydroxyphenyl)-3-(4-hydroxyphenyl)-1-hydroxypropane," with -- 1-(2-phosphonothio-4-hydroxyphenyl)-3-(4-hydroxyphenyl)-1-hydroxypropane, --.
Lines 64-65, replace 1-(2-phosphonothio-4-dihydroxyphenyl)-3-(4-hydroxyphenyl)-1,1-dihydroxypropane," with -- 1-(2-phosphonothio-4-hydroxyphenyl)-3-(4-hydroxyphenyl)-1,1dihydroxypropane, --.

Column 15,
Lines 3-4, replace "1-(2-phosphonothio-5-dihydroxyphenyl)-3-(4-hydroxyphenyl)-1,1 dihydroxypropane," with -- 1-(2-phosphonothio-5-hydroxyphenyl)-3-(4-hydroxyphenyl)-1,1dihydroxypropane, --.
Lines 49-50, replace "1-(2-phosphonothio-4-dihydroxyphenyl)-3-(4-hydroxyphenyl) propan-l-one," with -- 1-(2-phosphonothio-4-hydroxyphenyl)-3-(4-hydroxyphenyl) propan-l-one, --.

UNITED STATES PATENT AND TRADEMARK OFFICE
CERTIFICATE OF CORRECTION

PATENT NO. : 6,355,823 B1
DATED : March 12, 2002
INVENTOR(S) : Peerce

It is certified that error appears in the above-identified patent and that said Letters Patent is hereby corrected as shown below:

Column 16,
Lines 20-21, replace "1-(2-phosphonothio-5-dihydroxyphenyl)-2-(3-hydroxyphenyl) butane," with -- 1-(2-phosphonothio-5-hydroxyphenyl)-2-(3-hydroxyphenyl)butane, --.
Lines 46-47, replace "1-(2-phosphonothio-5-dihydroxyphenyl)-2-(4-hydroxyphenyl) butane," with -- 1-(2-phosphonothio-5-hydroxyphenyl)-2-(4-hydroxyphenyl)butane, --.

Column 17,
Lines 25-26, replace "1-(2-phosphonothio-4-dihydroxyphenyl)-2-(4-hydroxyphenyl)-1-hydroxybutane," with -- 1-(2-phosphonothio-4-hydroxyphenyl)-2-(4-hydroxyphenyl)-1-hydroxybutane, --.

Column 18,
Lines 10-11, replace "1-(2-phosphonothio-4-dihydroxyphenyl)-2-(4-hydroxyphenyl)-1,1-dihydroxybutane," with --
1-(2-phosphonothio-4-hydroxyphenyl)-2-(4-hydroxyphenyl)-1,1 dihydroxybutane, --.
Lines 16-17, replace "1-(2-phosphonothio-5-dihydroxyphenyl)-2-(4-hydroxyphenyl)-1,1-dihydroxybutane," with -- 1-(2-phosphonothio-5-hydroxyphenyl)-2-(4-hydroxyphenyl)-1,1-dihydroxybutane, --.
Lines 61-62, replace "1-(2-phosphonothio-4-dihydroxyphenyl)-2-(4-hydroxyphenyl) butan-l-one," with -- 1-(2-phosphonothio-4-hydroxyphenyl)-2-(4-hydroxyphenyl) butan-l-one, --.

Column 19,
Lines 27-28, replace "1-(2-phosphonothio-5-dihydroxyphenyl)-3-(3-hydroxyphenyl) butane," with -- 1-(2-phosphonothio-5-hydroxyphenyl)-3-(3-hydroxyphenyl)butane, --.
Lines 47-48, replace "1-(2-phosphonothio-4-dihydroxyphenyl)-3-(4-hydroxyphenyl) butane," with -- 1-(2-phosphonothio-4-hydroxyphenyl)-3-(4-hydroxyphenyl)butane, --.
Lines 53-54, replace "1-(2-phosphonothio-5-dihydroxyphenyl)-3-(4-hydroxyphenyl) butane," with -- 1-(2-phosphonothio-5-hydroxyphenyl)-3-(4-hydroxyphenyl)butane, --.

Column 20,
Lines 29-30, replace "1-(2-phosphonoimino-4-dihydroxyphenyl)-3-(4-hydroxyphenyl)-1-hydroaybutane," with -- 1-(2-phosphonoimino-4-hydroxyphenyl)-3-(4-hydroxyphenyl)-1-hydroxybutane, --.
Lines 31-32, replace "1-(2-phosphonothio-4-dihydroxyphenyl)-3-(4-hydroxyphenyl)-1-hydroxybutane," with -- 1-(2-phosphonothio-4-hydroxyphenyl)-3-(4-hydroxyphenyl)-1-hydroxybutane, --.

UNITED STATES PATENT AND TRADEMARK OFFICE
CERTIFICATE OF CORRECTION

PATENT NO. : 6,355,823 B1
DATED : March 12, 2002
INVENTOR(S) : Peerce

It is certified that error appears in the above-identified patent and that said Letters Patent is hereby corrected as shown below:

Column 21,
Lines 16-17, replace "1-(2-phosphonothio-4-dihydroxyphenyl)-3-(4-hydroxyphenyl)-1,1-dihydroxybutane," with -- 1-(2-phosphonothio-4-hydroxyphenyl)-3-(4-hydroxyphenyl)-1,1-dihydroxybutane, --.
Lines 22-23, replace "1-(2-phosphonothio-5-dihydroxyphenyl)-3-(4-hydroxyphenyl)-1,1-dihydroxybutane," with -- 1-(2-phosphonothio-5-hydroxyphenyl)-3-(4-hydroxyphenyl)-1,1-dihydroxybutane, --.

Column 22,
Lines 1-2, replace "1-(2-phosphonothio-4-dihydroxyphenyl)-3-(4-hydroxyphenyl)butan-l-one," with -- 1-(2-phosphonothio-4-hydroxyphenyl)-3-(4-hydroxyphenyl)butan-l-one, --.
Lines 33-34, replace "1-(2-phosphonothio-5-dihydroxyphenyl)-4-(3-hydroxyphenyl)butane," with -- 1-(2-phosphonothio-5-hydroxyphenyl)-4-(3-hydroxyphenyl)butane, --.
Lines 53-54, replace "1-(2-phosphonothio-4-dihydroxyphenyl)-4-(4-hydroxyphenyl)butane," with -- 1-(2-phosphonothio-4-hydroxyphenyl)-4-(4-hydroxyphenyl)butane, --.
Lines 59-60, replace "1-(2-phosphonothio-5-dihydroxyphenyl)-4-(4-hydroxyphenyl)butane," with -- 1-(2-phosphonothio-5-hydroxyphenyl)-4-(4-hydroxyphenyl)butane, --.

Column 23,
Lines 38-39, replace "1-(2-phosphonothio-4-dihydroxyphenyl)-4-(4-hydroxyphenyl)-1-hydroxybutane," with -- 1-(2-phosphonothio-4-hydroxyphenyl)-4-(4-hydroxyphenyl)-1-hydroxybutane, --.

Column 24,
Lines 23-24, replace "1-(2-phosphonothio-4-dihydroxyphenyl)-4-(4-hydroxyphenyl)-1,1-dihydroxybutane," with -- 1-(2-phosphonothio-4-hydroxyphenyl)-4-(4-hydroxyphenyl)-1,1-dihydroxybutane, --.
Lines 29-30, replace "1-(2-phosphonothio-5-dihydroxyphenyl)-4-(4-hydroxyphenyl)-1,1-dihydroxybutane," with -- 1-(2-phosphonothio-5-hydroxyphenyl)-4-(4-hydroxyphenyl)-1,1-dihydroxybutane, --.

Column 25,
Lines 7-8, replace "1-(2-phosphonothio-4-dihydroxyphenyl)-4-(4-hydroxyphenyl)butan-l-one," with -- 1-(2-phosphonothio-4-hydroxyphenyl)-4-(4-hydroxyphenyl)butan-l-one, --.
Line 38, replace "on" with -- one --.
Line 38, replace "the the" with -- the --.

UNITED STATES PATENT AND TRADEMARK OFFICE
CERTIFICATE OF CORRECTION

PATENT NO. : 6,355,823 B1
DATED : March 12, 2002
INVENTOR(S) : Peerce

It is certified that error appears in the above-identified patent and that said Letters Patent is hereby corrected as shown below:

Column 26,
Line 9, replace "they" with -- then --.
Line 49, replace "and" with -- as --.
Line 52, between "then" and "deprotected", insert -- be --.

Column 35,
Line 32, replace "$k_{0.5}$" with -- $K_{0.5}$ --.
Line 36, replace "$k_{0.5}$" with -- $K_{0.5}$ --.

Column 37,
Line 56, replace "[$^1$H]" with -- [$^3$H] --.

Column 38,
Line 50, replace "$CR^3E^{41}$" with -- $CR^3E^3$ --.
Line 51, replace "$SR^{41}$" with -- $SR^4$ --.

Column 40,
Line 53, replace "$CR^3E^4$" with -- $CR^3E^3$ --.

Column 42,
Line 57, replace "$CR^3E^4$" with -- $CR^3E^3$ --.

Column 44,
Line 54, replace "$CR^3E^4$" with -- $CR^3E^3$ --.

This certificate supersedes Certificate of Correction issued October 15, 2002, which was a duplicate of certificate that issued September 24, 2002.

Signed and Sealed this

Fifteenth Day of April, 2003

JAMES E. ROGAN
*Director of the United States Patent and Trademark Office*